(12) United States Patent
Davidson et al.

(10) Patent No.: US 9,067,033 B2
(45) Date of Patent: Jun. 30, 2015

(54) COMPACT ORONASAL PATIENT INTERFACE

(75) Inventors: Aaron Samuel Davidson, Mona Vale (AU); Michael Kassipillai Gunaratnam, Marsfield (AU); Susan Robyn Lynch, Bella Vista (AU); Milind Chandrakant Raje, Wentworthville (AU); Gary Christopher Robinson, East Killara (AU); Steven John Lubke, Stanmore (AU); Gregory Scott Smart, Randwick (AU); Philip Rodney Kwok, Chatswood (AU); Rupert Christian Scheiner, Davidson (AU)

(73) Assignee: ResMed Limited, Bella Vista (AU)

( * ) Notice: Subject to any disclaimer, the term of this patent is extended or adjusted under 35 U.S.C. 154(b) by 1041 days.

(21) Appl. No.: 13/103,491

(22) Filed: May 9, 2011

(65) Prior Publication Data

US 2011/0209709 A1    Sep. 1, 2011

Related U.S. Application Data

(63) Continuation of application No. 10/584,711, filed as application No. PCT/AU2004/001832 on Dec. 24, 2004, now Pat. No. 7,942,148.

(60) Provisional application No. 60/533,214, filed on Dec. 31, 2003.

(51) Int. Cl.
    *A61M 11/00* (2006.01)
    *A61M 16/06* (2006.01)
    *A62B 18/08* (2006.01)

(52) U.S. Cl.
    CPC ........... *A61M 16/06* (2013.01); *A61M 16/0666* (2013.01); *A61M 16/0683* (2013.01); *A62B 18/084* (2013.01); *A61M 16/0611* (2014.02); *A61M 16/0616* (2014.02)

(58) Field of Classification Search
    CPC ................. A61M 16/0666; A61M 2210/0618; A61M 2210/0625; A61M 16/06; A61M 15/08
    USPC ............ 128/206.21, 206.24, 206.28, 206.29, 128/207.11
    See application file for complete search history.

(56) References Cited

U.S. PATENT DOCUMENTS

| 443,191 A | 12/1890 | Illing |
|---|---|---|
| 781,516 A | 1/1905 | Guthrie, Jr. |

(Continued)

FOREIGN PATENT DOCUMENTS

| AU | 51130/96 | 10/1996 |
|---|---|---|
| AU | 2005100738 | 11/2005 |

(Continued)

OTHER PUBLICATIONS

Final Office Action issued in a related U.S. Appl. No. 12/700,878, dated Mar. 7, 2014, including PTO-892 listing US 443,191, US 2,625,155, US 5,005,571, US 6,082,360, US 2002/0096178, US 2006/0207597, and US 2009/0032026.

(Continued)

*Primary Examiner* — Steven Douglas
(74) *Attorney, Agent, or Firm* — Nixon & Vanderhye P.C.

(57) ABSTRACT

A breathing arrangement includes a patient interface, at least one inlet conduit, and a headgear assembly. The patient interface includes a mouth covering assembly including a cushion structured to sealingly engage around exterior of a patient's mouth in use, a nozzle assembly including a pair of nozzles structured to sealingly engage within nasal passages of a patient's nose in use, and a flexible element connecting the mouth covering assembly and the nozzle assembly. The at least one inlet conduit is structured to deliver breathable gas into at least one of the mouth covering assembly and the nozzle assembly for breathing by the patient. The headgear assembly is removably connected to at least one of the mouth covering assembly and the nozzle assembly so as to maintain the mouth covering assembly and the nozzle assembly in a desired position on the patient's face.

41 Claims, 58 Drawing Sheets

(56) References Cited

U.S. PATENT DOCUMENTS

| | | |
|---|---|---|
| 838,434 A | 12/1906 | Morgan |
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,439,855 A | 4/1948 | Mortensen |
| 2,625,155 A | 1/1953 | Engelder |
| 2,706,983 A | 4/1955 | Matheson et al. |
| 2,931,356 A | 4/1960 | Schwarz |
| 3,013,556 A | 12/1961 | Galleher |
| 3,670,726 A | 6/1972 | Mahon et al. |
| 3,682,171 A | 8/1972 | Dali et al. |
| 3,739,774 A | 6/1973 | Gregory |
| 3,754,552 A | 8/1973 | King |
| 3,861,385 A | 1/1975 | Carden |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Teip |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 10/1985 | Chien |
| 4,572,323 A | 2/1986 | Randall |
| 4,587,967 A | 5/1986 | Chu et al. |
| 4,601,465 A | 7/1986 | Roy |
| 4,617,637 A | 10/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,753,233 A | 6/1988 | Grimes |
| 4,767,411 A | 8/1988 | Edmunds |
| 4,774,946 A | 10/1988 | Ackerman et al. |
| 4,782,832 A | 11/1988 | Trimble et al. |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | Amrhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,299,599 A | 4/1994 | Farmer et al. |
| 5,304,146 A | 4/1994 | Johnson et al. |
| 5,335,656 A | 8/1994 | Bowe et al. |
| 5,349,949 A | 9/1994 | Schegerin |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,560,354 A | 10/1996 | Berthon-Jones et al. |
| 5,570,684 A | 11/1996 | Behr |
| 5,592,938 A | 1/1997 | Scarberry et al. |
| 5,623,923 A | 4/1997 | Bertheau et al. |
| 5,647,357 A | 7/1997 | Barnett et al. |
| 5,653,228 A | 8/1997 | Byrd |

(56) References Cited

U.S. PATENT DOCUMENTS

| | | |
|---|---|---|
| 5,655,527 A | 8/1997 | Scarberry et al. |
| 5,662,101 A | 9/1997 | Ogden et al. |
| 5,682,881 A | 11/1997 | Winthrop et al. |
| 5,704,345 A | 1/1998 | Berthon-Jones et al. |
| 5,707,342 A | 1/1998 | Tanaka |
| 5,724,965 A | 3/1998 | Handke et al. |
| 5,735,272 A | 4/1998 | Dillon et al. |
| 5,740,799 A | 4/1998 | Nielsen |
| 5,752,511 A | 5/1998 | Simmons et al. |
| 5,794,619 A | 8/1998 | Edeiman et al. |
| 5,807,341 A | 9/1998 | Heim |
| 5,842,469 A | 12/1998 | Rapp et al. |
| 5,906,203 A | 5/1999 | Klockseth et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,017,315 A | 1/2000 | Starr et al. |
| 6,019,101 A | 2/2000 | Cotner et al. |
| 6,026,811 A | 2/2000 | Settle |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,193,914 B1 | 2/2001 | Harrison |
| 6,196,223 B1 | 3/2001 | Belfer et al. |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,418,928 B1 | 7/2002 | Bordewick et al. |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,594 B1 | 6/2003 | Drew et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |
| 6,805,117 B1 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,860,270 B2 | 3/2005 | Sniadach |
| 6,895,965 B2 | 5/2005 | Scarberry et al. |
| 6,907,882 B2 | 6/2005 | Ging et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam et al. |
| 7,448,386 B2 | 11/2008 | Ho et al. |
| 7,523,754 B2 | 4/2009 | Lithgow |
| 7,658,189 B2 | 2/2010 | Davidson |
| 2001/0020474 A1 | 9/2001 | Hecker et al. |
| 2002/0005198 A1 | 1/2002 | Kwok et al. |
| 2002/0029780 A1 | 3/2002 | Frater et al. |
| 2002/0046755 A1 | 4/2002 | DeVoss |
| 2002/0053347 A1 | 5/2002 | Ziaee |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1 | 12/2002 | Bishop |
| 2003/0000526 A1 | 1/2003 | Goebel |

(56) References Cited

U.S. PATENT DOCUMENTS

| | | | |
|---|---|---|---|
| 2003/0019495 A1 | 1/2003 | Palkon et al. | |
| 2003/0024530 A1 | 2/2003 | Sniadach | |
| 2003/0079749 A1 | 5/2003 | Strickland et al. | |
| 2003/0079751 A1 | 5/2003 | Kwok | |
| 2003/0089373 A1 | 5/2003 | Gradon et al. | |
| 2003/0111080 A1 | 6/2003 | Olsen et al. | |
| 2003/0154980 A1 | 8/2003 | Berthon-Jones et al. | |
| 2003/0168063 A1 | 9/2003 | Gambone et al. | |
| 2003/0196656 A1 | 10/2003 | Moore et al. | |
| 2003/0196658 A1 | 10/2003 | Ging et al. | |
| 2004/0025882 A1 | 2/2004 | Madaus et al. | |
| 2004/0025885 A1 | 2/2004 | Payne, Jr. | |
| 2004/0045551 A1 | 3/2004 | Eaton et al. | |
| 2004/0065328 A1 | 4/2004 | Amarasinghe et al. | |
| 2004/0106891 A1 | 6/2004 | Langan et al. | |
| 2004/0111104 A1 | 6/2004 | Schein et al. | |
| 2004/0112384 A1 | 6/2004 | Lithgow et al. | |
| 2004/0118406 A1 | 6/2004 | Lithgow et al. | |
| 2004/0127856 A1 | 7/2004 | Johnson | |
| 2004/0211428 A1 | 10/2004 | Jones | |
| 2004/0226564 A1 | 11/2004 | Persson | |
| 2004/0226566 A1 | 11/2004 | Gunaratnam et al. | |
| 2005/0011523 A1 | 1/2005 | Aylsworth et al. | |
| 2005/0028822 A1 | 2/2005 | Sleeper et al. | |
| 2005/0033247 A1 | 2/2005 | Thompson | |
| 2005/0039757 A1 | 2/2005 | Wood | |
| 2005/0051171 A1 | 3/2005 | Booth | |
| 2005/0051176 A1 | 3/2005 | Riggins | |
| 2005/0056286 A1 | 3/2005 | Huddart et al. | |
| 2005/0061326 A1 | 3/2005 | Payne, Jr. | |
| 2005/0101933 A1 | 5/2005 | Marrs et al. | |
| 2005/0150495 A1 | 7/2005 | Rittner et al. | |
| 2005/0155604 A1 | 7/2005 | Ging et al. | |
| 2005/0211252 A1 | 9/2005 | Lang et al. | |
| 2005/0241644 A1 | 11/2005 | Gunaratnam et al. | |
| 2005/0284481 A1 | 12/2005 | Meyer | |
| 2006/0060200 A1 | 3/2006 | Ho et al. | |
| 2006/0081250 A1 | 4/2006 | Bordewick et al. | |
| 2006/0090760 A1 | 5/2006 | Gradon et al. | |
| 2006/0095008 A1 | 5/2006 | Lampropoulos et al. | |
| 2006/0095009 A1 | 5/2006 | Lampropoulos et al. | |
| 2006/0118117 A1 | 6/2006 | Berthon-Jones | |
| 2006/0124131 A1 | 6/2006 | Chandran et al. | |
| 2006/0137690 A1 | 6/2006 | Gunaratnam et al. | |
| 2006/0174887 A1 | 8/2006 | Chandran et al. | |
| 2006/0207597 A1 | 9/2006 | Wright | |
| 2006/0237017 A1 | 10/2006 | Davidson et al. | |
| 2006/0283461 A1 | 12/2006 | Lubke et al. | |
| 2007/0023044 A1 | 2/2007 | Kwok et al. | |
| 2007/0125387 A1 | 6/2007 | Zollinger et al. | |
| 2007/0144525 A1 | 6/2007 | Davidson et al. | |
| 2007/0186930 A1 | 8/2007 | Davidson et al. | |
| 2007/0272249 A1 | 11/2007 | Chandran et al. | |
| 2007/0282272 A1 | 12/2007 | Bannon et al. | |
| 2008/0004573 A1 | 1/2008 | Kaufmann et al. | |
| 2008/0006277 A1 | 1/2008 | Worboys et al. | |
| 2008/0047560 A1 | 2/2008 | Veliss et al. | |
| 2008/0060649 A1 | 3/2008 | Veliss et al. | |
| 2008/0065022 A1 | 3/2008 | Kyvik et al. | |
| 2008/0110469 A1 | 5/2008 | Weinberg | |
| 2008/0200880 A1 | 8/2008 | Kyvik et al. | |
| 2008/0257354 A1 | 10/2008 | Davidson et al. | |
| 2009/0032026 A1 | 2/2009 | Price et al. | |
| 2009/0044808 A1 | 2/2009 | Guney et al. | |
| 2010/0000534 A1 | 1/2010 | Kooij et al. | |
| 2010/0018534 A1 | 1/2010 | Veliss et al. | |

FOREIGN PATENT DOCUMENTS

| | | |
|---|---|---|
| DE | 185017 | 5/1907 |
| DE | 30 11 900 | 10/1980 |
| DE | 146688 | 2/1981 |
| DE | 3719009 | 12/1988 |
| DE | 39 27 038 | 2/1991 |
| DE | 297 23 101 | 7/1998 |
| DE | 197 03 526 | 8/1998 |
| DE | 19944242 | 3/2001 |
| DE | 100 02 571 | 7/2001 |
| DE | 102 13 905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 0 303 090 | 4/1992 |
| EP | 0 634 186 | 1/1995 |
| EP | 0658356 | 6/1995 |
| EP | 0 776 679 | 6/1997 |
| EP | 1 099 452 | 5/2001 |
| EP | 1 258 266 | 11/2002 |
| EP | 1481702 | 12/2004 |
| FR | 2 720 280 | 12/1995 |
| GB | 0532214 | 1/1941 |
| GB | 2 176 404 | 12/1986 |
| GB | 2368533 | 5/2002 |
| GB | 2385533 | 8/2003 |
| WO | WO 82/03548 | 10/1982 |
| WO | WO 01/97892 | 4/1987 |
| WO | WO 87/01950 | 4/1987 |
| WO | WO 92/20392 A1 | 11/1992 |
| WO | WO 92/20395 | 11/1992 |
| WO | WO 96/28207 | 9/1996 |
| WO | WO 98/04310 | 2/1998 |
| WO | WO 98/12965 | 4/1998 |
| WO | WO 98/23305 | 6/1998 |
| WO | WO 99/16327 | 4/1999 |
| WO | WO 99/25410 | 5/1999 |
| WO | WO 99/43375 | 9/1999 |
| WO | WO 99/61088 | 12/1999 |
| WO | WO 00/20072 | 4/2000 |
| WO | WO 00/38772 | 7/2000 |
| WO | WO 00/50121 | 8/2000 |
| WO | WO 00/69521 | 11/2000 |
| WO | WO 00/72905 A1 | 12/2000 |
| WO | WO 00/74758 | 12/2000 |
| WO | WO 00/76568 | 12/2000 |
| WO | WO 00/78384 | 12/2000 |
| WO | WO 01/62326 | 8/2001 |
| WO | WO 01/95965 | 12/2001 |
| WO | WO 01/97893 | 12/2001 |
| WO | WO 02/38221 | 5/2002 |
| WO | WO 02/45784 | 6/2002 |
| WO | WO 03/076020 | 9/2003 |
| WO | WO 03/090827 | 11/2003 |
| WO | WO 03/105921 | 12/2003 |
| WO | WO 2004/022146 | 3/2004 |
| WO | WO 2004/041342 | 5/2004 |
| WO | WO 2004/052438 A1 | 6/2004 |
| WO | WO 2004/073778 | 9/2004 |
| WO | WO 2004/078230 | 9/2004 |
| WO | WO 2005/053781 | 6/2005 |
| WO | WO 2005/063328 | 7/2005 |
| WO | WO 2005/063328 A1 | 7/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU06/000031 | 1/2006 |
| WO | PCT/AU06/000770 | 6/2006 |
| WO | PCT/AU2006/00077 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | PCT/AU2007/00193 | 12/2007 |
| WO | WO 2007/139531 A1 | 12/2007 |
| WO | WO 2007/143772 | 12/2007 |
| WO | WO 2007/145534 | 12/2007 |

(56) References Cited

FOREIGN PATENT DOCUMENTS

| WO | WO 2008/007985 A1 | 1/2008 |
|---|---|---|
| WO | WO 2008/011682 | 1/2008 |
| WO | WO 2008/011683 | 1/2008 |
| WO | WO 2008/040050 | 4/2008 |
| WO | WO 2008/040050 A1 | 4/2008 |
| WO | WO 2008/070929 | 6/2008 |
| WO | PCT/AU06/000417 | 3/2009 |
| WO | WO 2009/108994 | 9/2009 |
| WO | WO 2009/109004 | 9/2009 |
| WO | WO 2010/028425 | 3/2010 |

OTHER PUBLICATIONS

Communication issued in corresponding European Appln. No. 11 195 610.8 dated Mar. 31, 2014.
Communication issued in a corresponding European Appln. No. 04 802 133.1, dated May 13, 2013.
Communication issued in a corresponding European Appln. No. 11 195 610.8, dated May 22, 2013.
Office Action issued in a corresponding Chinese Appln. No. 200910166118.0, dated May 27, 2013, with English translation thereof.
Communication issued in a related European Application No. 04 802 133.1, dated Jul. 19, 2012.
Examination Report mailed Oct. 6, 2011 in New Zealand Application No. 595521 (2 pages).
Notification of First Office Action issued Sep. 30, 2011 in Chinese Appln. No. 200910166118.0, with English translation (10 pages).
Examination Report mailed Oct. 5, 2011 in European Appln. No. 04 802 133.1 (4 pages).
Office Action issued in related Chinese Appl. No. 200710000902.5 with English translation (Mar. 31, 2012).
Examination Report mailed May 12, 2010 in New Zealand Application No. 585133 (2 pages).
Examination Report mailed Oct. 6, 2011 in New Zealand Appln. No. 595521 (2 pages).
Office Action issued in a corresponding Chinese Application No. 200710000902.5 (Jan. 31, 2013) with English translation thereof.
"Ear Loop Face Mask".
Adam J. Singer MD et al. "The Cyanoacrylate Topical Skin Adhesives," American Journal of Emergency Medicine, vol. 26, 2008, pp. 490-496.
Webster's Third New International Dictionary, 1993, Dictionary definition for adjustable, bendable, and mild steel.
ComfortLite™, Respironics, http://comfortlite.respironics.com.
ComfortLite™ 2, Respironics, http://comfortlite2.respironics.com.
Webster's New World Dictionary, Third College Edition 1988, definition for engaged and flexible.
EP Supplementary Search Report issued in EP Application 03793493, dated Dec. 2, 2009.
European Search Report filed on Jul. 27, 2009 in EP Application No. 07784697.0.
European Search Report issued in EP 07845378.4, mailed Dec. 1, 2009.
Examiner's Report No. 3 mailed Nov. 18, 2009 in New Zealand Application No. 2003275762.
Examination Report filed in New Zealand Application 539836, dated Aug. 25, 2005.
Extended European Search Report dated Mar. 19, 2009 in European Application No. EP 08161249.
Extended European Search Report Mailed Sep. 3, 2009 in corresponding EP Application No. 09161984.1.
Extended European Search Report. Application No. EP 08154854, dated Nov. 27, 2008.
International Search Report for PCT/AU2005/000803, dated Jun. 30, 2005.
International Search Report for PCT/AU2007/001052, dated Oct. 9, 2007.
International Search Report for PCT/AU2007/001051, dated Nov. 5, 2007.

International Search Report for PCT/AU2007/001936, dated Mar. 4, 2008.
International Search Report PCT/AU2009/001144, dated Dec. 18, 2009.
International Search Report PCT/AU2009/000240, dated May 21, 2009.
International Search Report PCT/AU2009/000262, dated Jun. 9, 2009.
International Search Report PCT/AU2003/001471, dated Feb. 12, 2004.
International Search Report PCT/AU2003/001163, dated Nov. 4, 2003.
Joel W. Beam, "Tissue Adhesives for Simple Traumatic Lacerations," Journal of Athletic Training, 2008, vol. 43, No. 2, pp. 222-224.
Merriam-Webster Online Dictionary definition of moveable from the 14th century.
Subbu Venkatraman et al., "Review Skin Adhesives and Skin Adhesion 1. Transdermal Drug Delivery Systems," Biomaterials, vol. 19, 1998, pp. 1119-1136.
Supplementary Search Report issued in European Appln. 05746824. 1, dated Dec. 17, 2009.
Supplementary European Search Report mailed Dec. 18, 2009 in European Application No. 03810331.3.
Unsolicited email from Elson Silva, PhD, dated Mar. 28, 2008, "Requesting IDS of US 6,766,817 for patents on fluids moving on porosity by Unsaturated Hydraulic Flow," (email provided in both HTML and plain text format).
International Preliminary Report on Patentability for PCT/AU2004/001832 dated Jul. 3, 2006.
International Search Report for PCT/AU2004/001832, mailed Mar. 24, 2005.
International Search Report filed in PCT/AU2006/000770, mailed Aug. 3, 2006.
"If You Hate CPAP! You Need CPAP Pro®," www.cpappro.com.
U.S. Appl. No. 10/385,701, filed Aug. 2003, Berthon-Jones et al.
U.S. Appl. No. 10/533,928, filed Jul. 2005, Berthon-Jones.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/491,016, filed Feb. 2007, Kwok et al.
U.S. Appl. No. 11/597,909, filed Jul. 2007, Worboys.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/461,448, filed Aug. 2009, Berthon-Jones.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
Notice of Reasons for Rejection mailed Jun. 8, 2010 in Japanese Application No. 2006-545847, together with an English translation.
Notification of First Office Action issued Apr. 2, 2010 in Chinese Application No. 200710000902.5 with English translation.
U.S. Appl. No. 60/424,686, filed Nov. 2002, Lithgow.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.

(56) References Cited

OTHER PUBLICATIONS

U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
Supplementary European Search Report mailed Sep. 8, 2009 in European Appln. No. 04802133.1 (7 pages).
Office Action mailed Dec. 22, 2009 in European Appln. No. 04802133.1 (7 pages).
European Patent Office Communication Mailed Sep. 21, 2010 in European Application 04 802 133.1 (6 pages).
Respironics Co.—Mask Family—http://masksfamily.respironics.com/ viewed on Jul. 24, 2006.
ResMed Co.—Mask Products—http://resmed.com/portal/site/ResMedUS/index.jsp? . . . viewed on Jul. 24, 2006.
Fisher and Paykel Co.—Product Family—http://www.fphcare.com/osa/products.asp/ viewed on Jul. 24, 2006.
Hans Rudolph, Inc.—Mask Products—http://www.rudolphkc.com/products.php?category=MASKS viewed on Jul. 24, 2006.
Snapp Nasal Interface, Tiara Medical Systems, Inc.—http://www.tiaramed.com/asp_shops/shopdisplayproducts.asp?id=109 &cat=SNAPP%2A+Nasal+Interface viewed on Jul. 24, 2006.
U.S. Appl. No. 60/634,802, filed Dec. 10, 2004.
U.S. Appl. No. 60/645,672, filed Jan. 21, 2005.
International Search Report for PCT/AU2004/001832 dated Mar. 24, 2005.
U.S. Appl. No. 60/483,622, filed Jul. 2003, Kwok et al.
U.S. Appl. No. 60/795,615, filed Apr. 2006, Judson et al.
U.S. Appl. No. 11/474,415, filed Jun. 2006, Davidson et al.
U.S. Appl. No. 11/447,295, filed Jun. 2006, Lubke et al.
Office Action issued in related U.S. Appl. No. 12/700,878, dated Jul. 11, 2013, including PTO-892 listing US 4,263,908, US 4,782,832, US 6,017,315, US 6,123,071, US 2002/0053347, US 6,412,487, US 6,431,172, US 6,532,961, US 6,584,975, US 2003/0196656 and US 2006/0090760.
First Examination Report issued in corresponding New Zealand Appln. No. 626585 dated Jun. 27, 2014.
Office Action issued in a corresponding U.S. Appl. No. 12/700,878 dated Aug. 8, 2014, including PTO-892 listing US 838,434; US 1,229,050; US 2,439,855; and US 4,782,832.
Office Action issued in a corresponding Chinese Application No. 200710000902.5 (Sep. 7, 2012) with English translation thereof.
Extended European Search Report issued in a corresponding EP Application No. 11195610.8 (Sep. 17, 2012).
First Examination Report issued in a corresponding New Zealand Appln. No. 606024, dated Jan. 25, 2013.
Office Action issued in a corresponding Chinese Application No. 200910166118.0 (Nov. 7, 2012) with English translation thereof.
Communication issued in corresponding European Appln. No. 11 195 610.8 dated Feb. 6, 2015.
Final Office Action issued in a related U.S. Appl. No. 12/700,878 dated Mar. 26, 2015, including PTO-892 listing US 6,119,694.

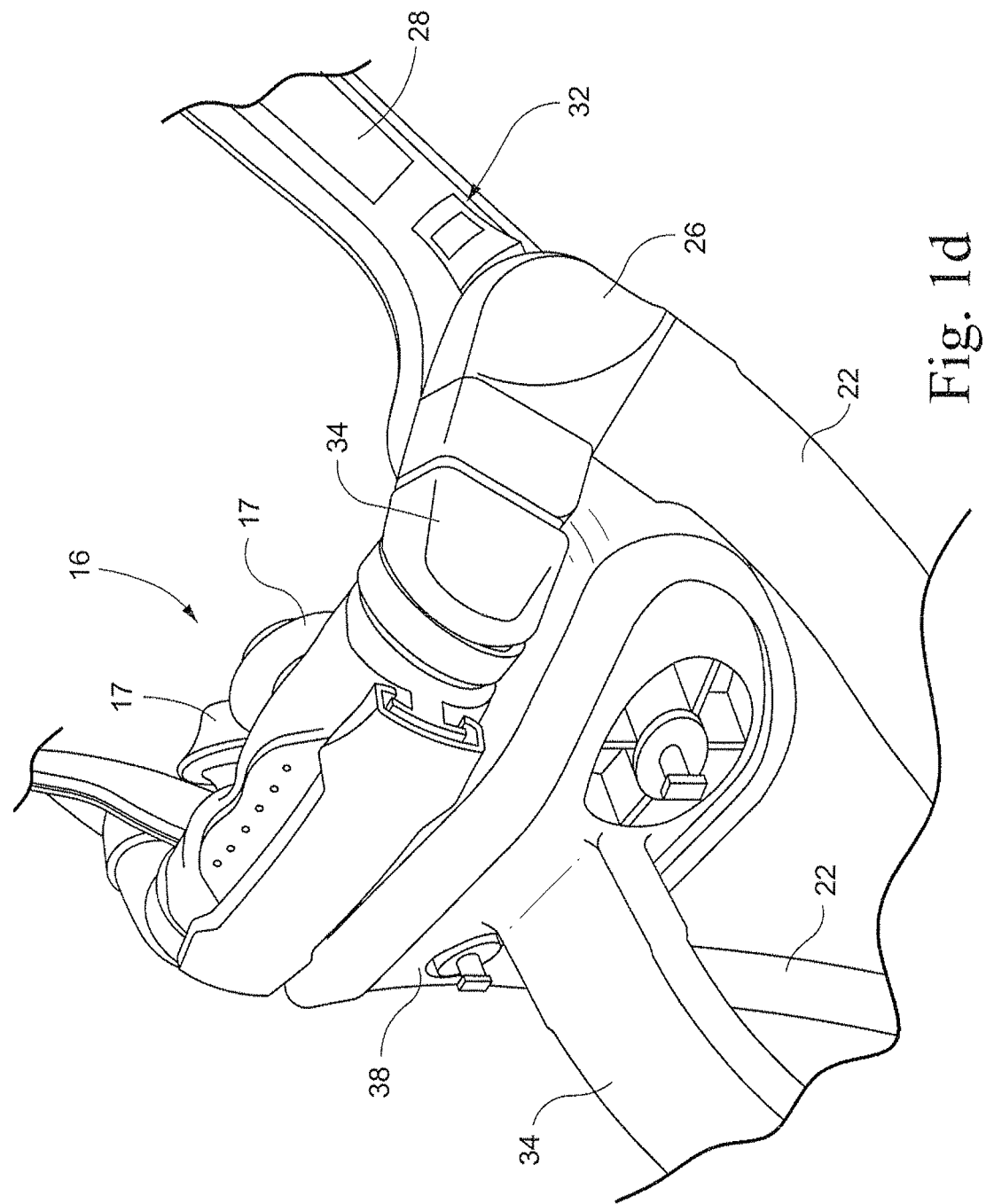

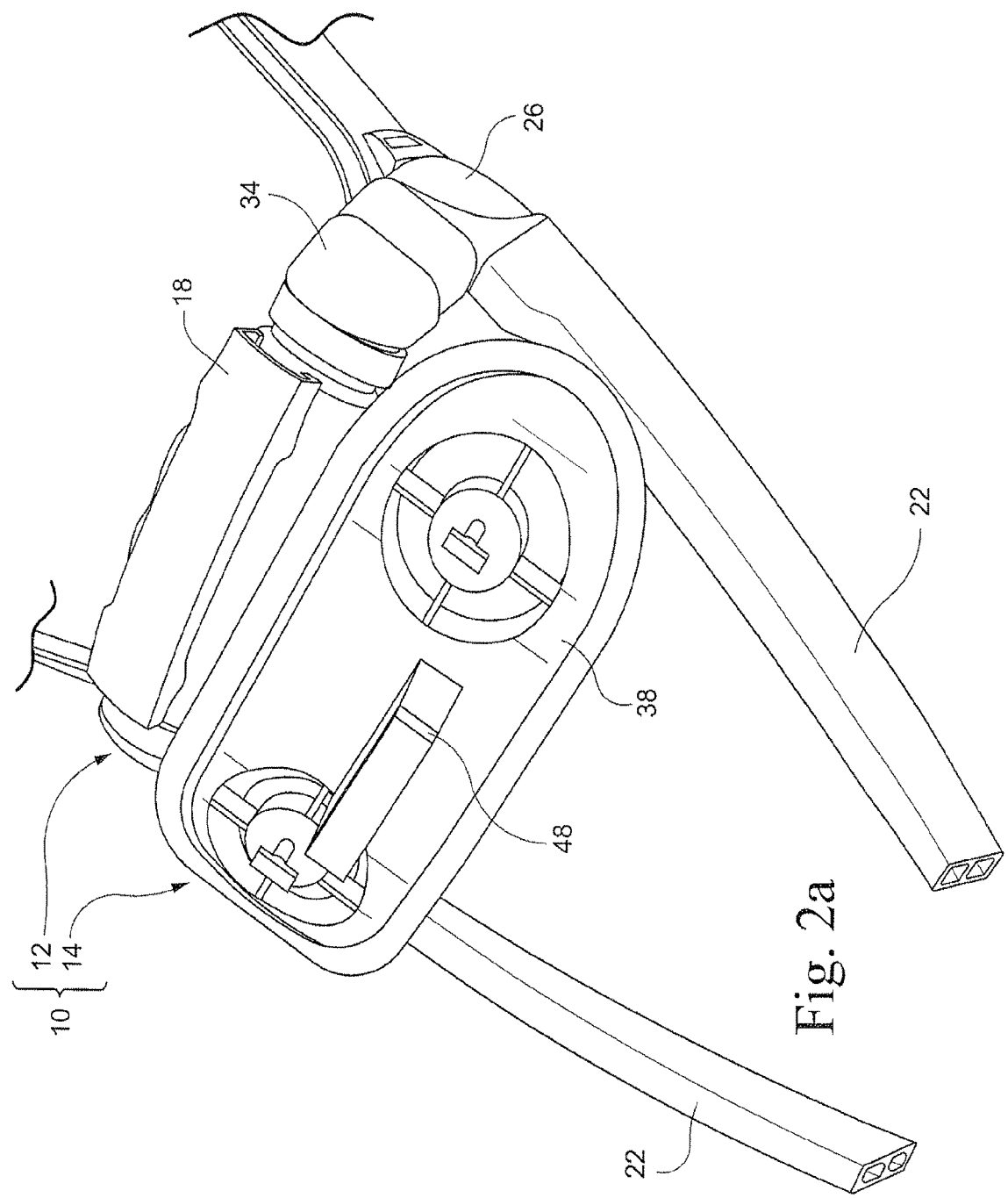

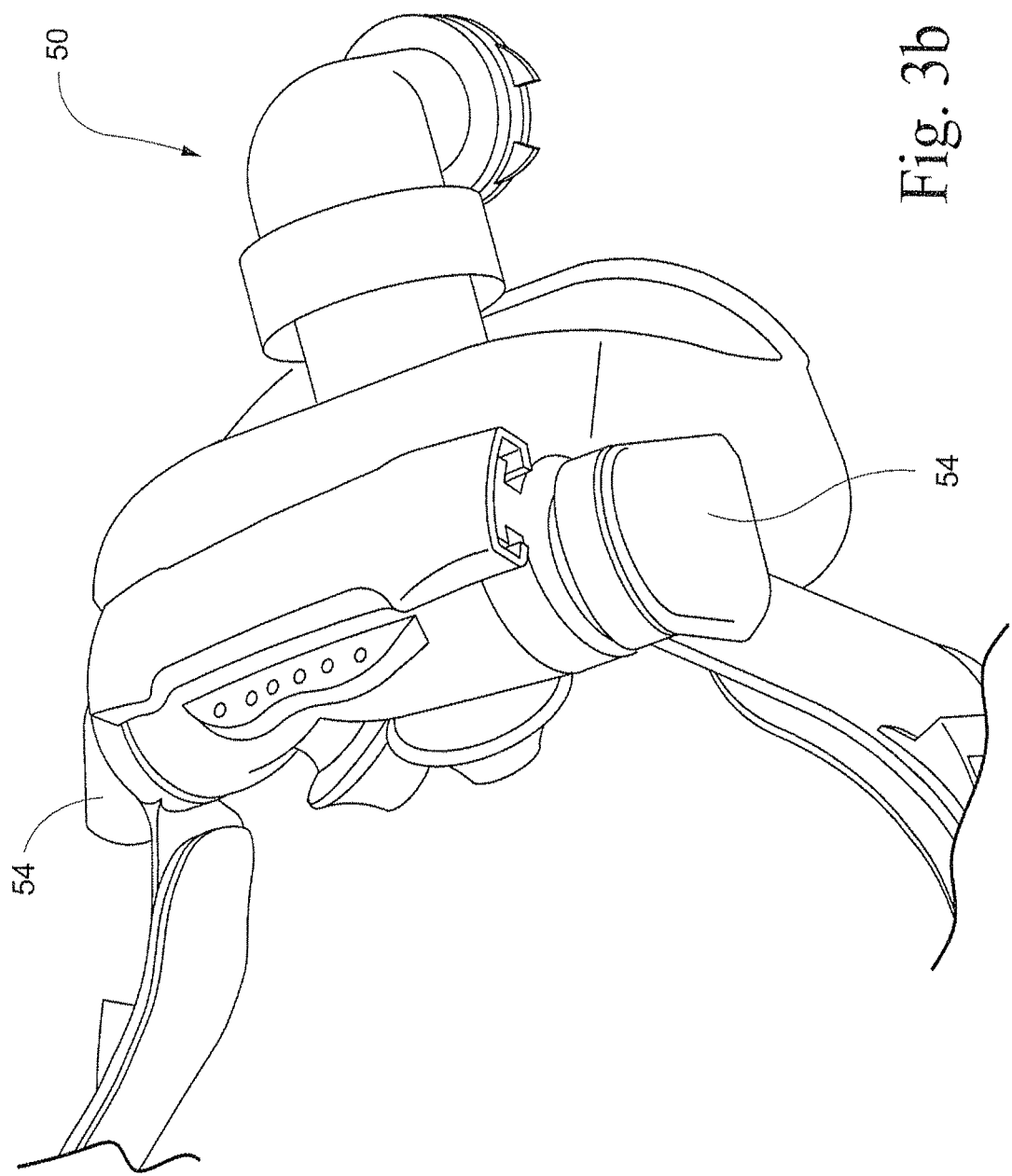

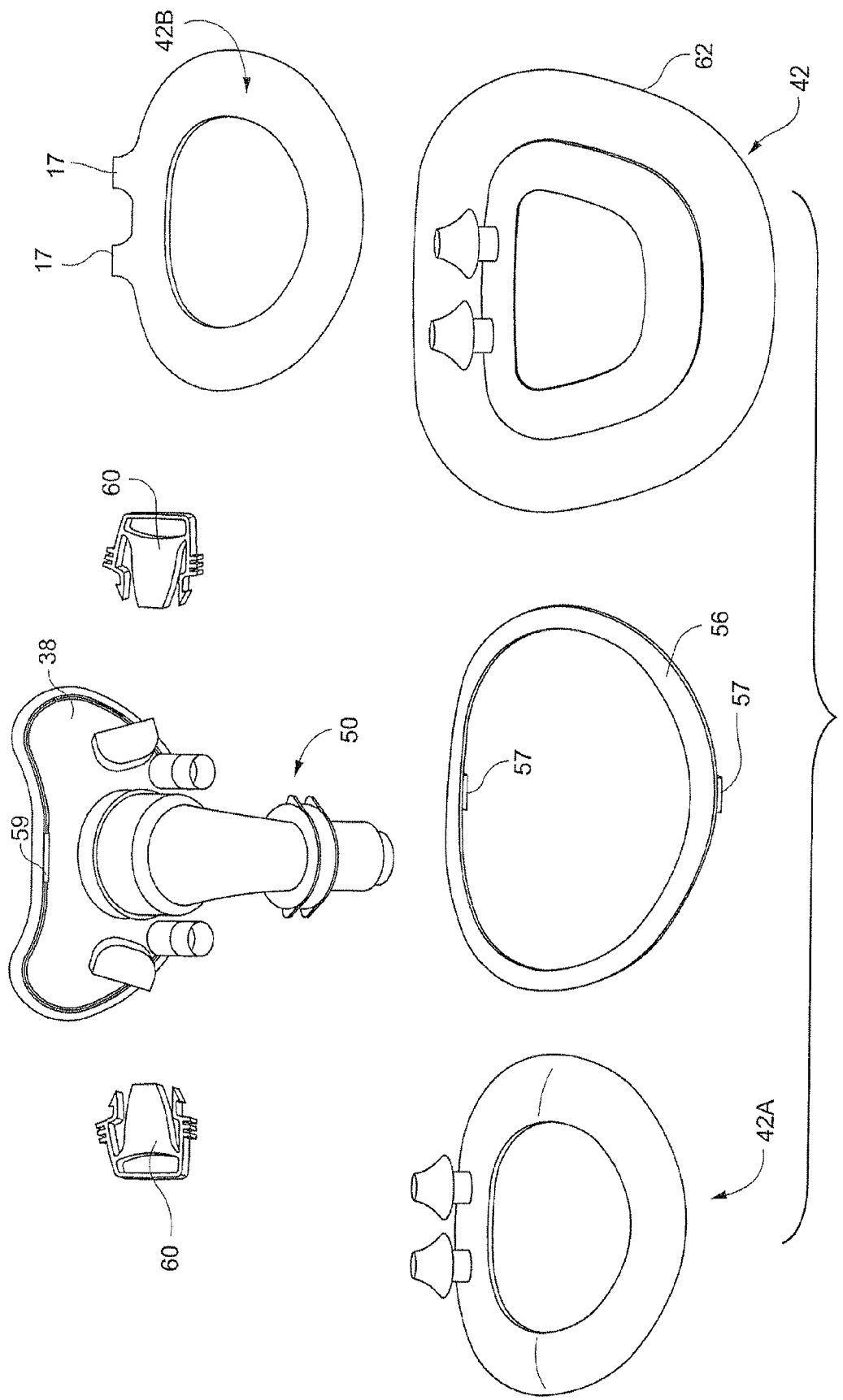

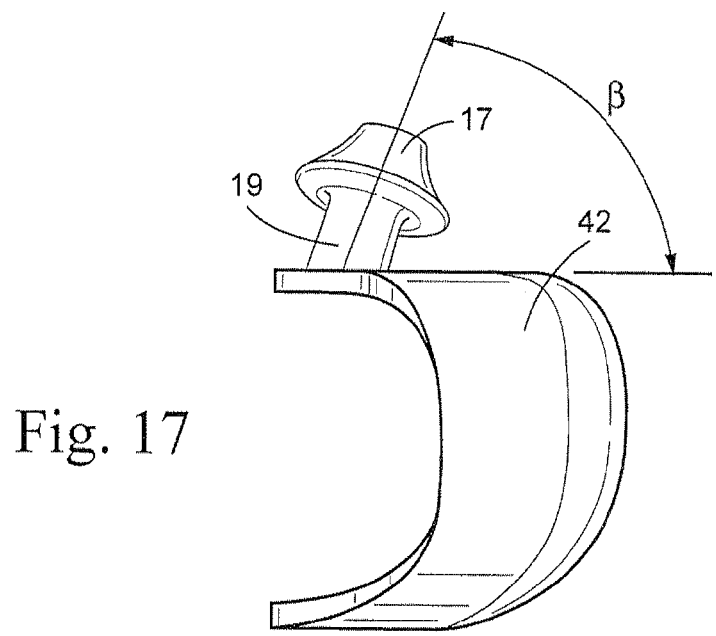
Fig. 17
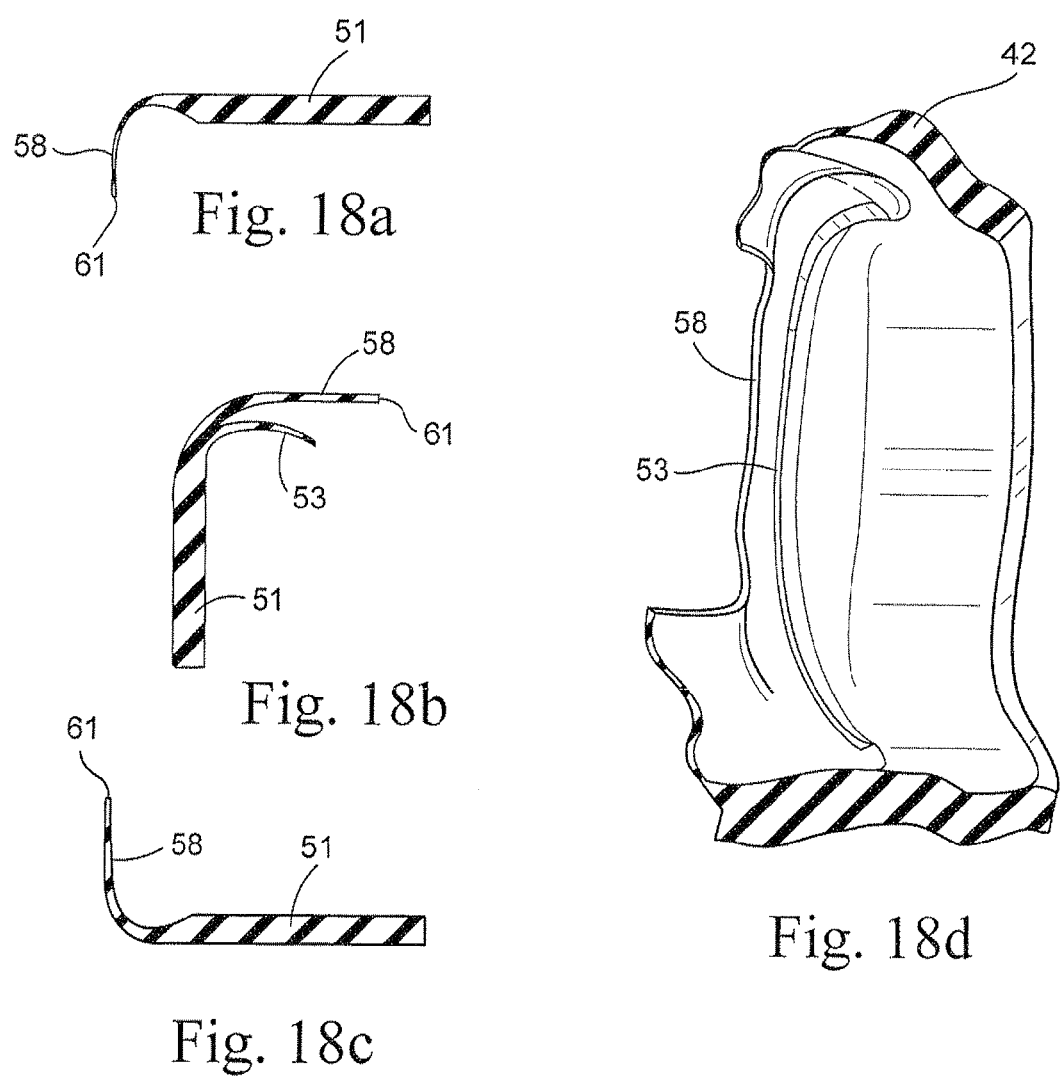
Fig. 18a
Fig. 18b
Fig. 18c
Fig. 18d

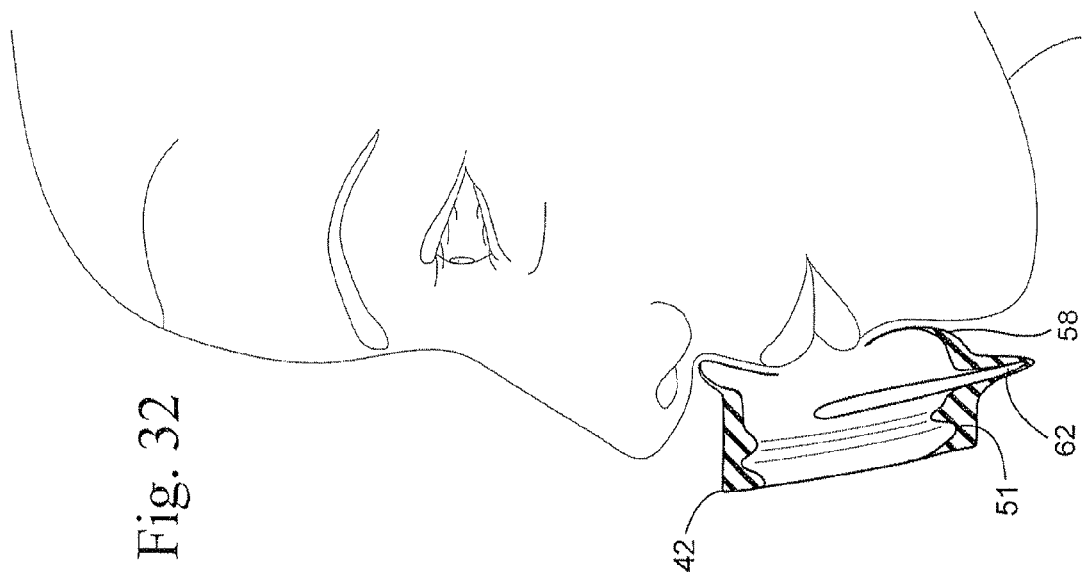
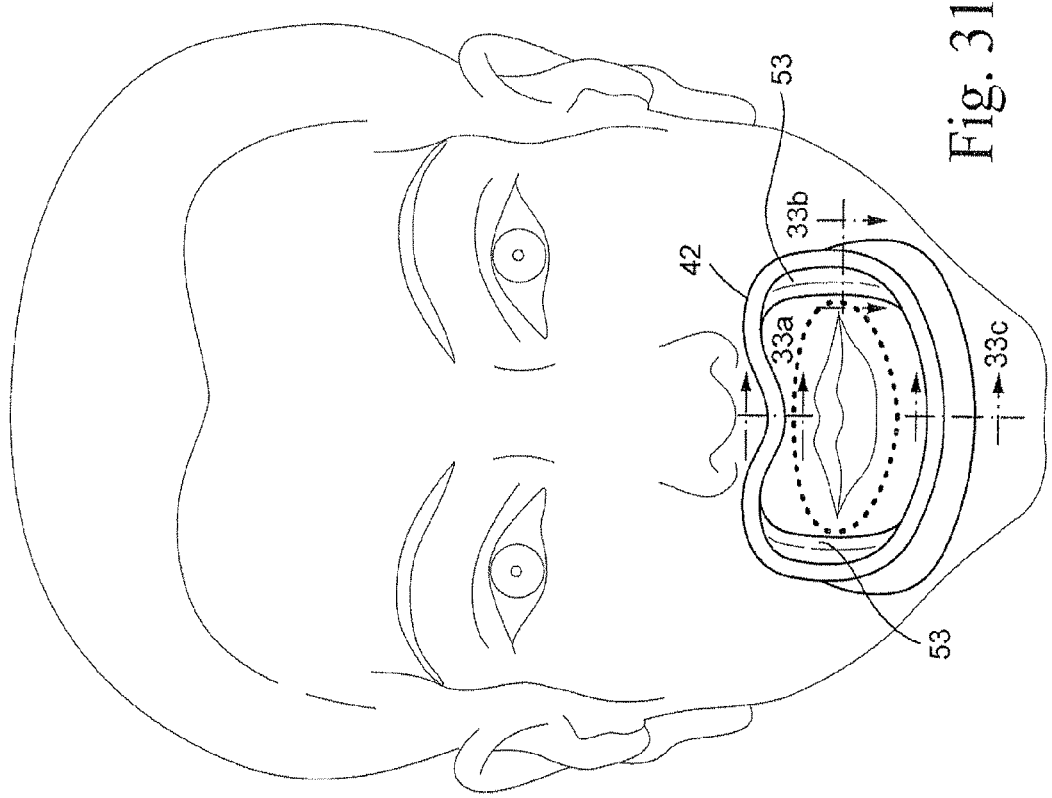

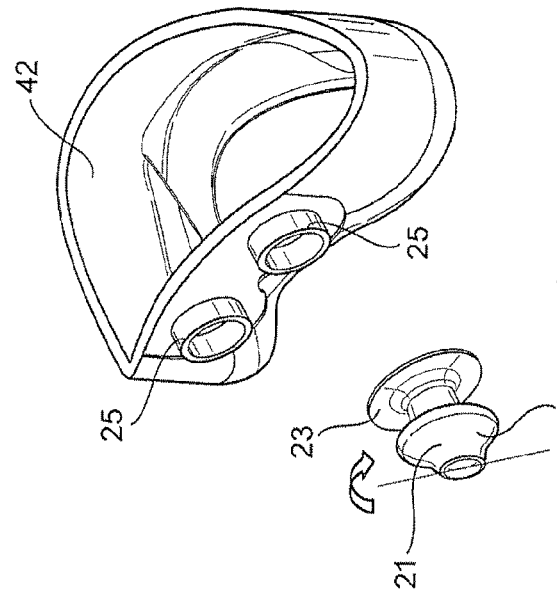
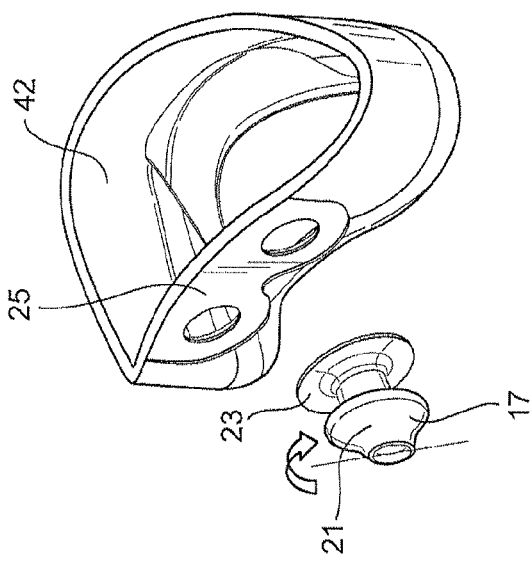
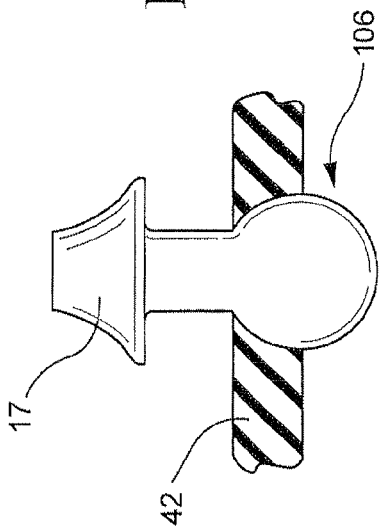
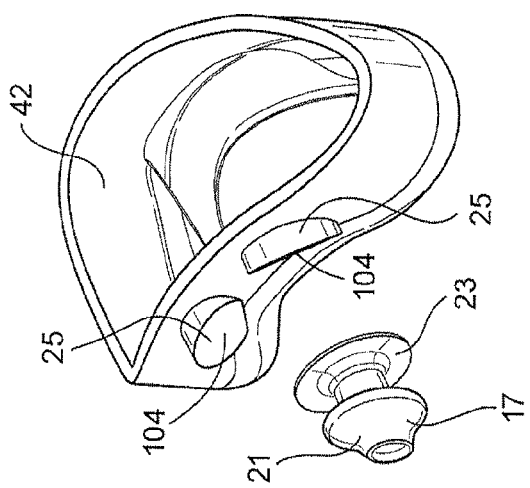

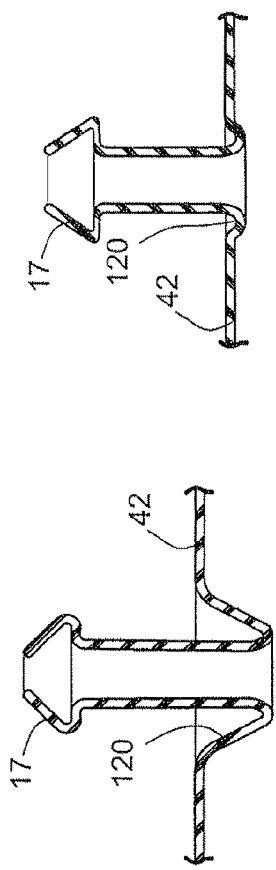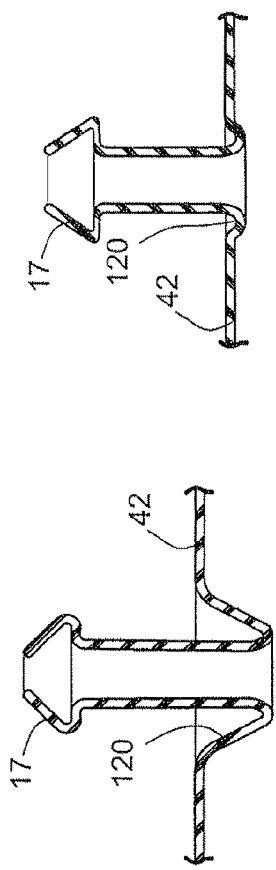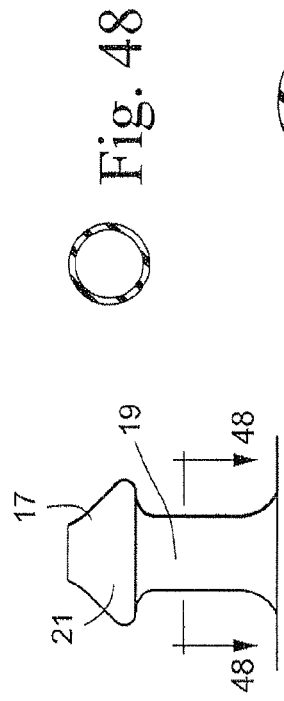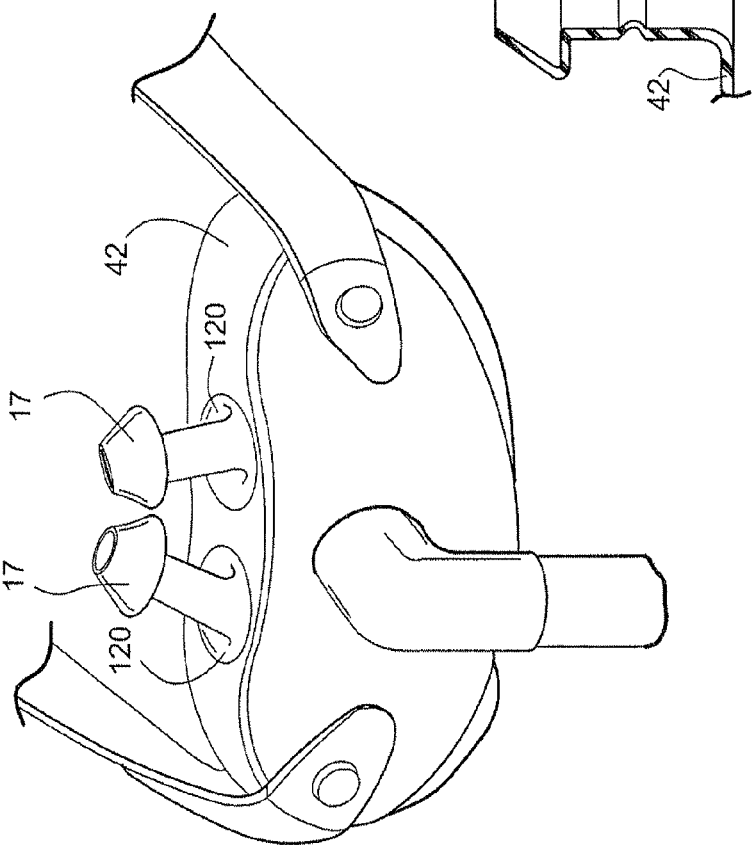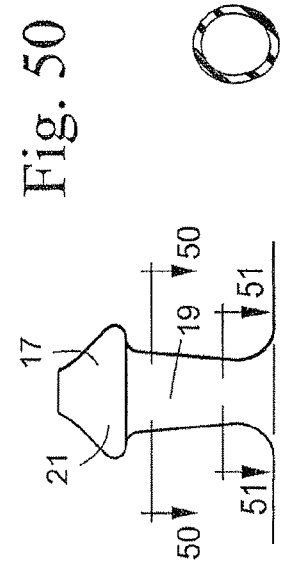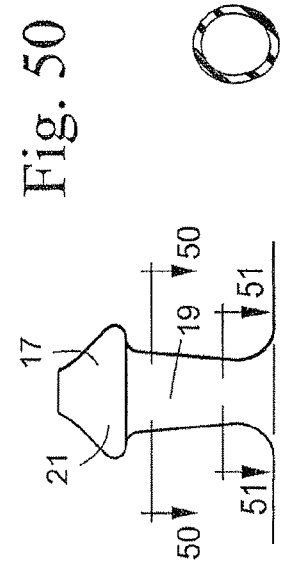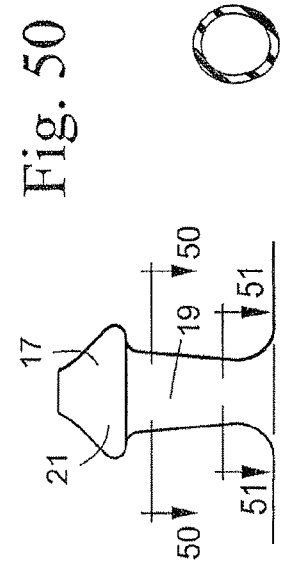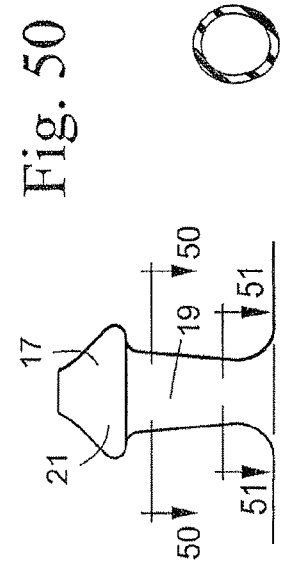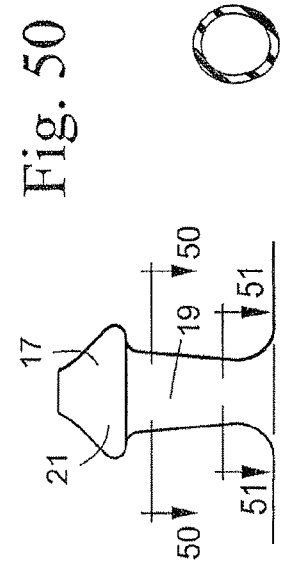

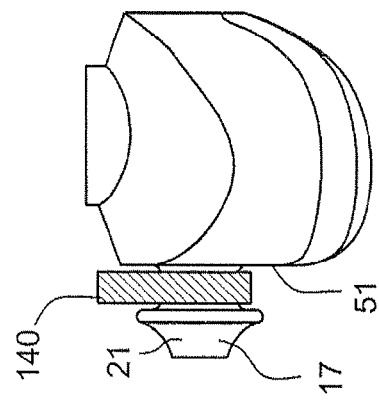
Fig. 61
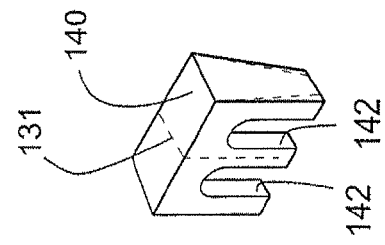
Fig. 62
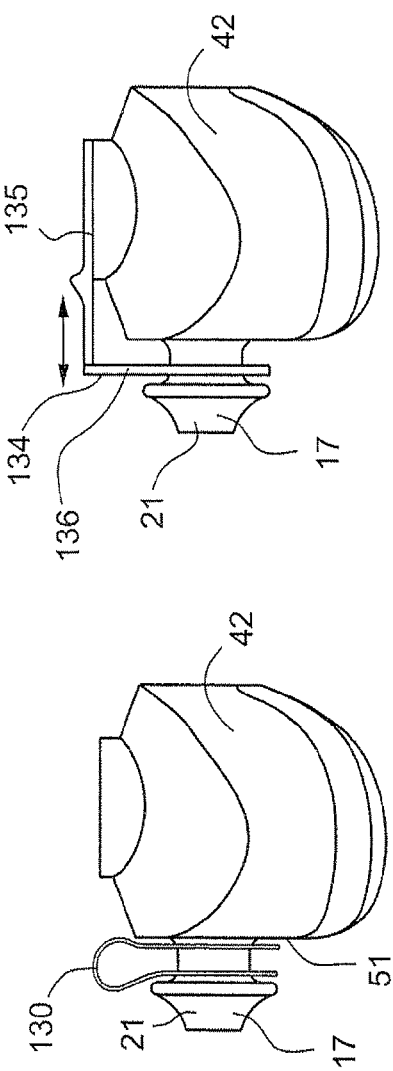
Fig. 59
Fig. 60
Fig. 57
Fig. 58

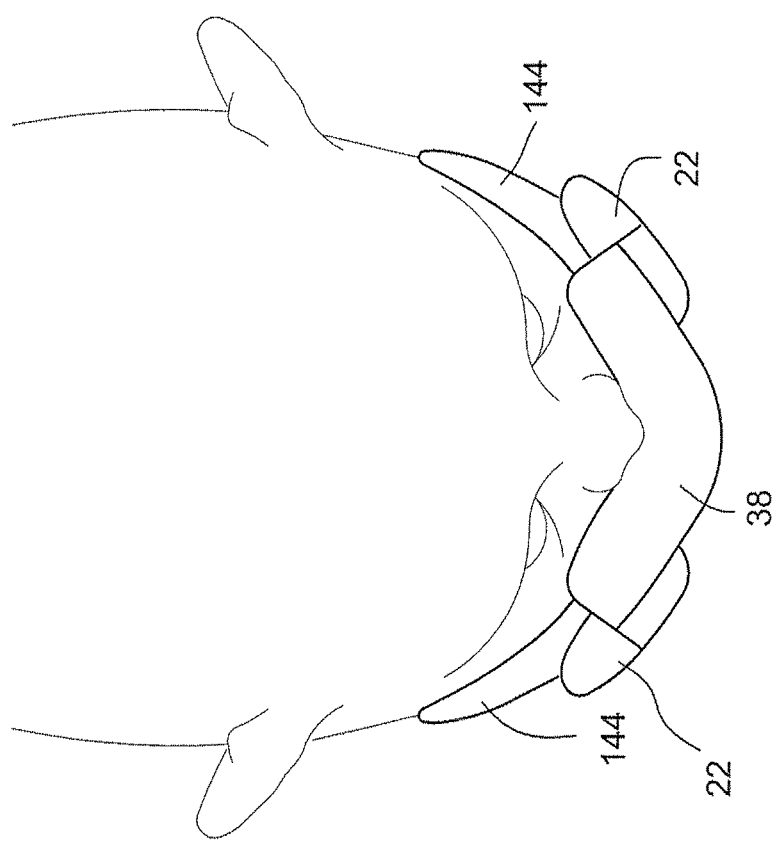

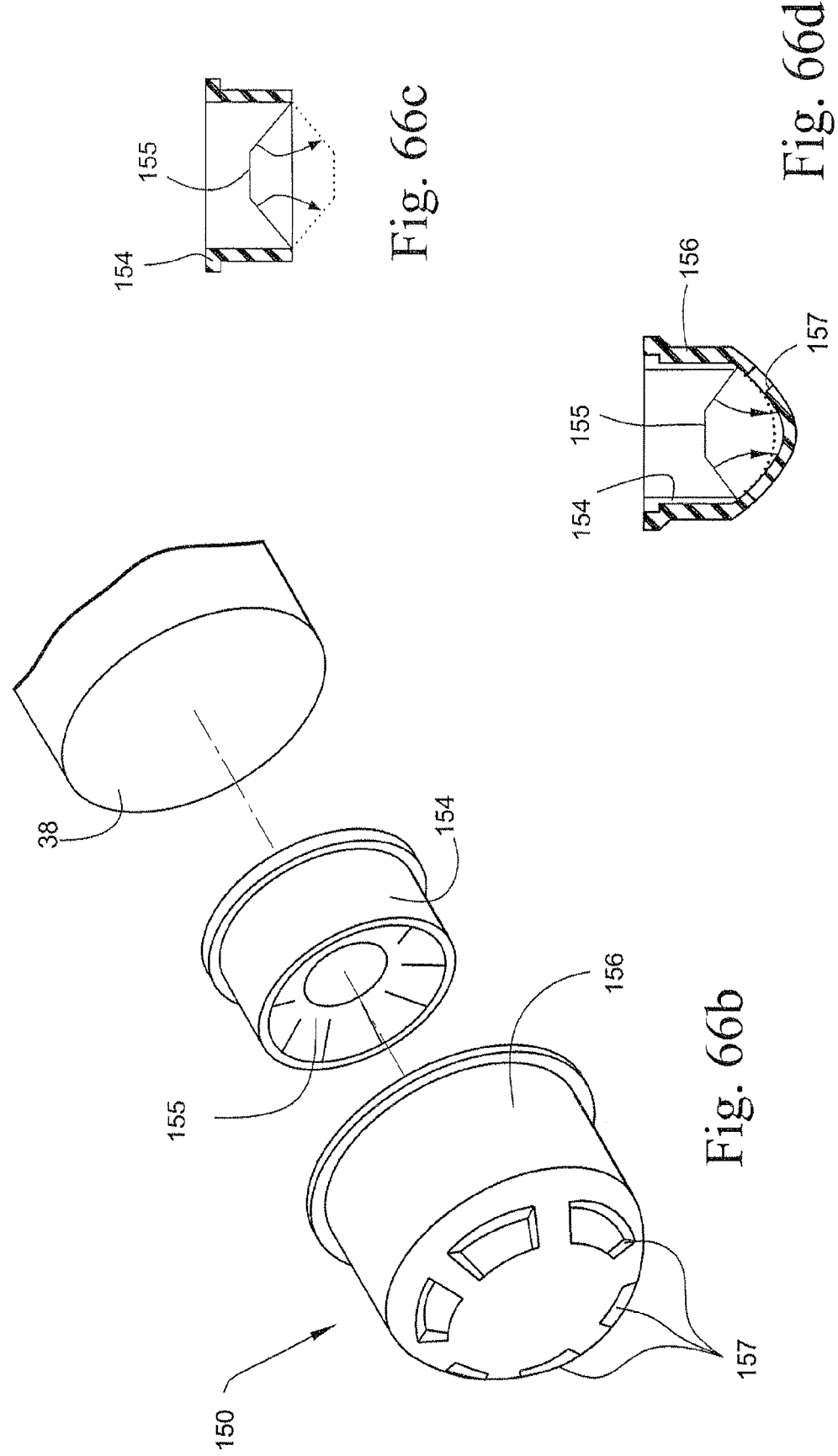

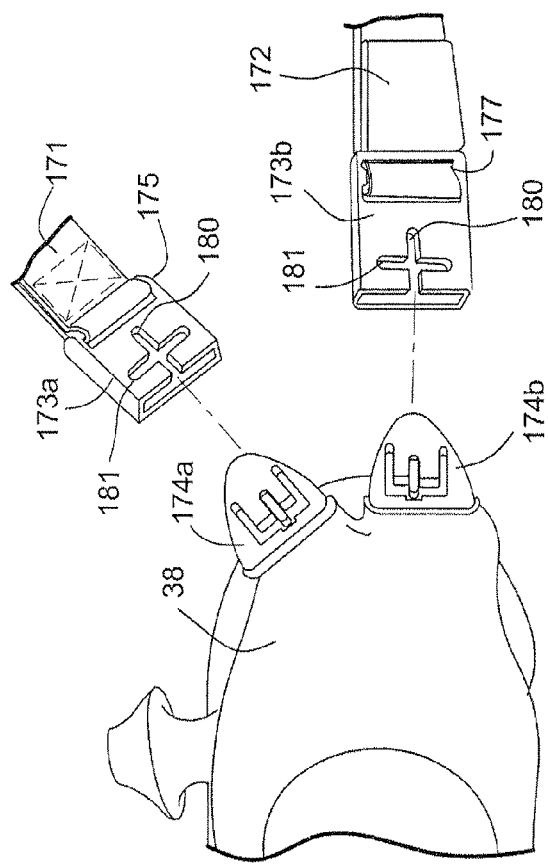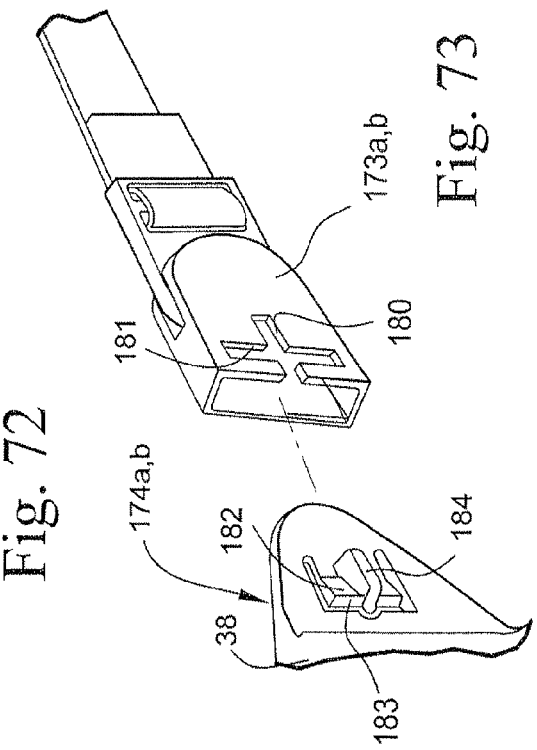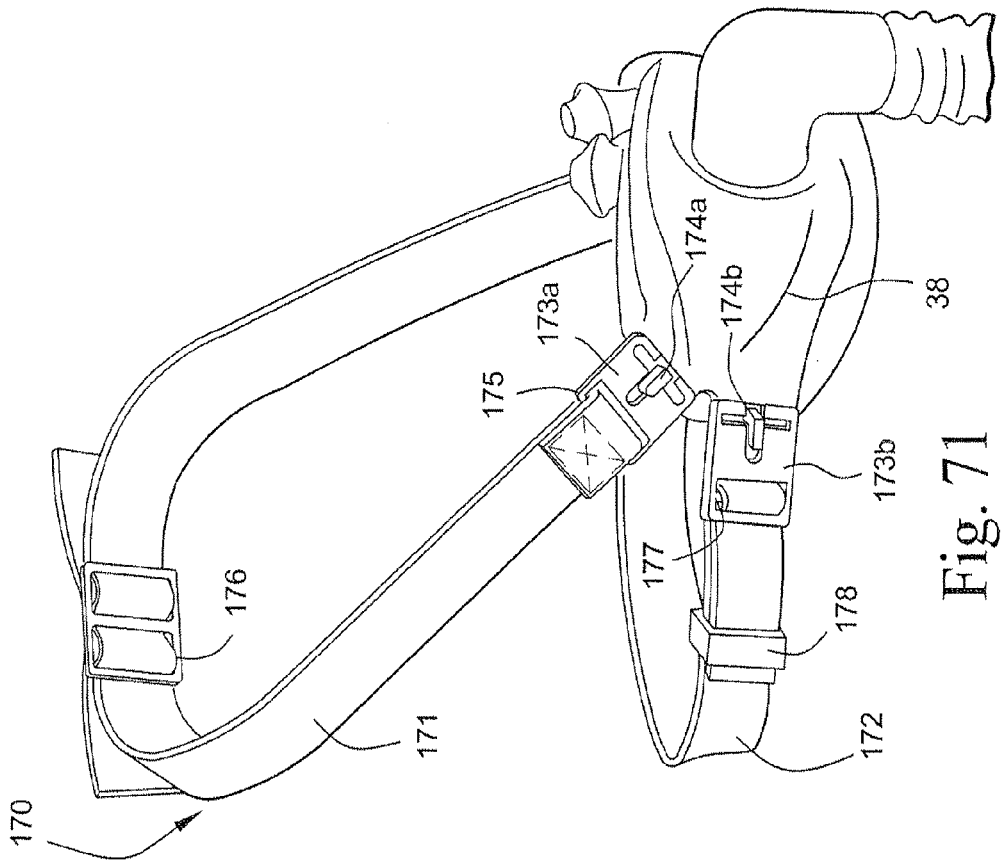

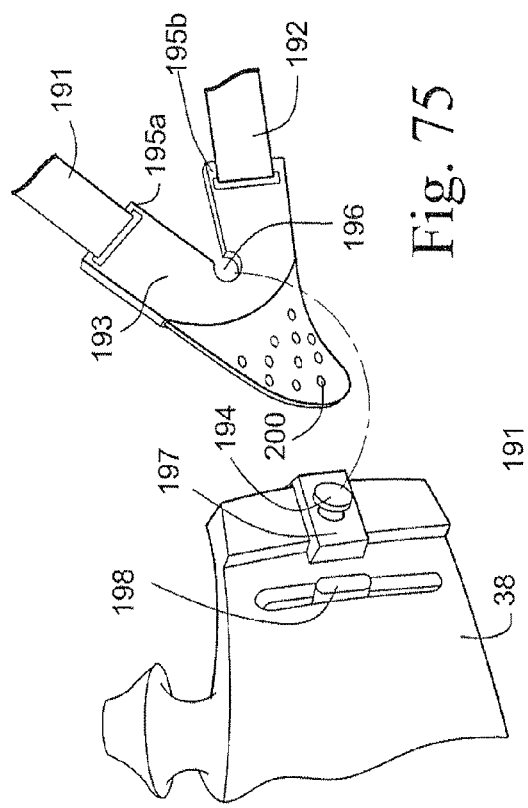
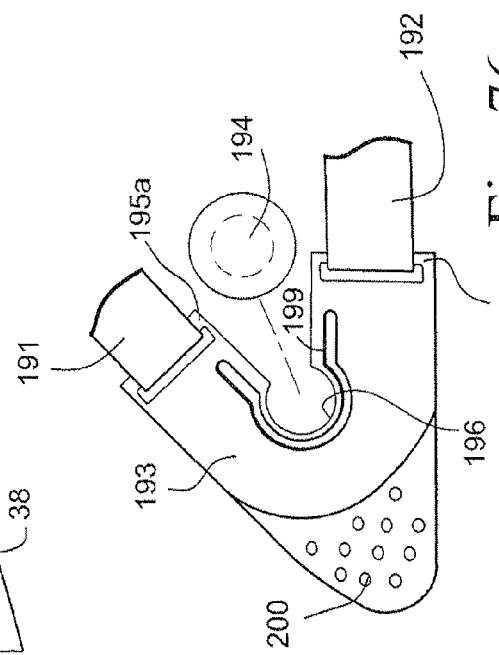
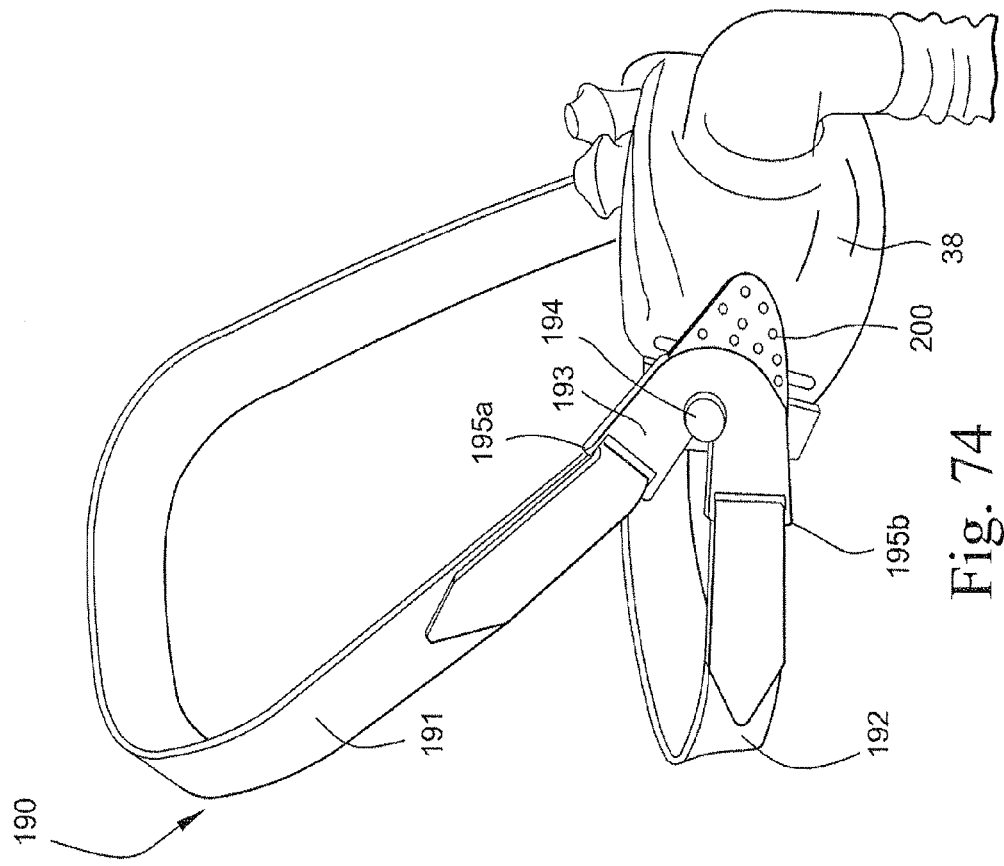

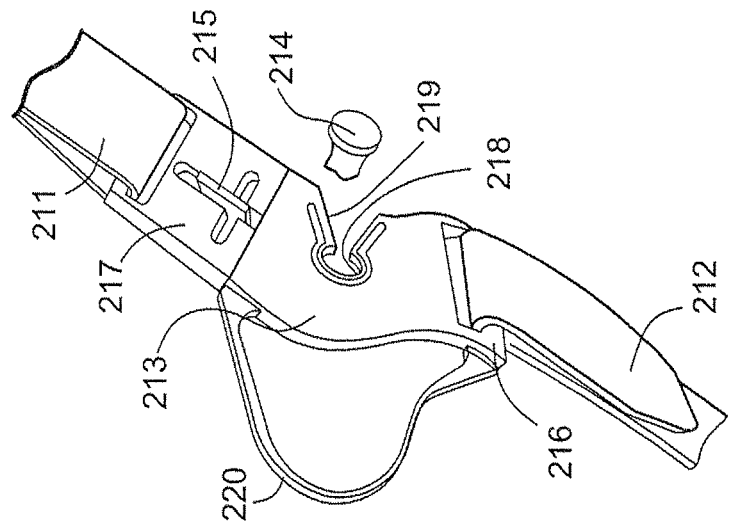
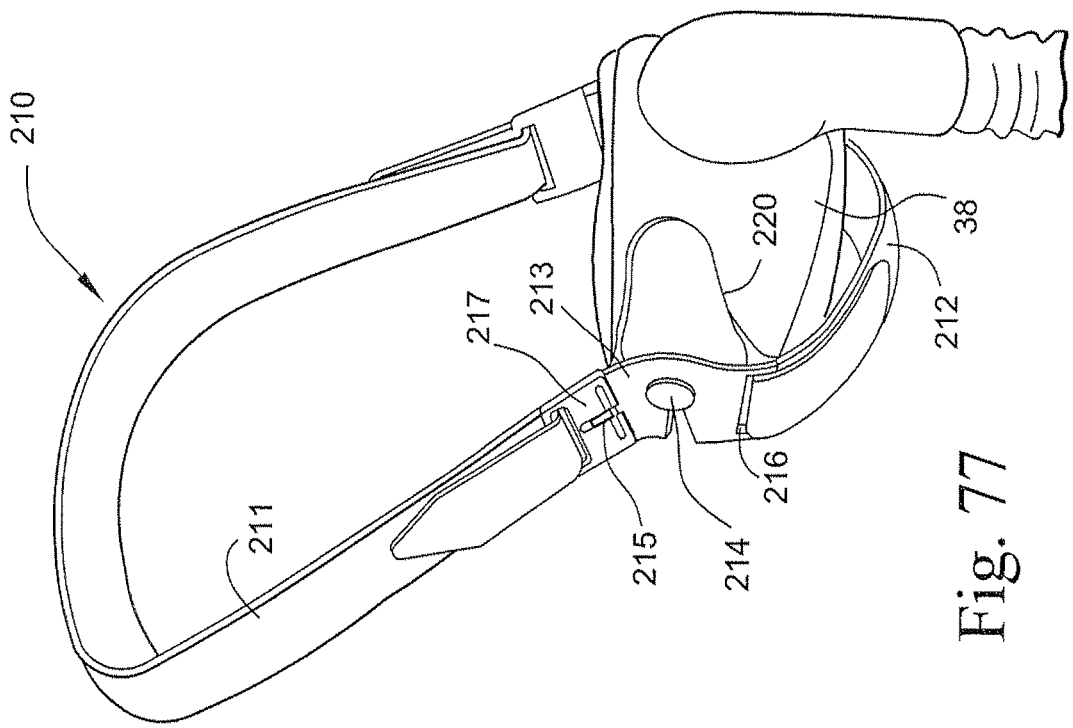

COMPACT ORONASAL PATIENT INTERFACE

CROSS-REFERENCE TO RELATED APPLICATIONS

This application is a continuation of U.S. application Ser. No. 10/584,711, filed Jun. 26, 2006, which is the U.S. national phase of International Application No. PCT/AU2004/001832, filed Dec. 24, 2004, which designated the U.S. and claims priority to U.S. Provisional Application No. 60/533,214 filed Dec. 31, 2003, each of which is incorporated herein in its entirety.

FIELD OF THE INVENTION

The present invention relates to a patient interface for use between a patient and a structure to deliver a breathable gas to the patient, such as is used in gas delivery systems for respiratory therapy. Examples of such therapy are Continuous Positive Airway Pressure (CPAP) treatment, assisted respiration or Non-Invasive Positive Pressure Ventilation (NIPPV).

BACKGROUND OF THE INVENTION

Comfort and effectiveness remain a continuing challenge for engineers and designers of the interface between a mechanical ventilator and a patient. Such patient interfaces are currently employed for a variety of purposes including the delivery of non-invasive ventilation or for the delivery of pressurized air to persons who suffer from sleep disordered breathing conditions such as Obstructive Sleep Apnea (OSA). In non-invasive positive pressure ventilation, a supply of air at positive pressure is provided by a blower to a patient interface through an air delivery conduit. The patient interface may take the form of a nasal mask, nose & mouth mask, full face mask or nasal prongs.

A mask may comprise (i) a rigid or semi-rigid portion which attaches directly to the air delivery conduit and (ii) a soft patient contacting portion. The rigid or semi-rigid portion, known as a shell or frame, may define a nose-receiving cavity, or a mouth covering chamber. Other forms of patient interface, such as nasal cannulae, comprise a pair of nasal prongs, nasal inserts or nozzles.

The soft patient contacting portion is typically known as a cushion or membrane and is generally shaped during manufacture to match the facial contours of a patient in order to provide the optimum seal.

An inherent characteristic of patient interfaces such as nasal masks or nozzle assemblies is that they do not seal the mouth region. A number of patients thus find that during sleep when muscles relax, mouth leak may occur. Alternatively some patients are naturally mouth breathers and thus find a nasal patient interface ineffective. Mouth leak is undesirable as among other difficulties, it may result in noise, increased treatment pressure to compensate for the leak or an increased load on the nasal passages and potentially nasal obstruction or a runny nose.

Patient interfaces such as full face masks or nose and mouth masks address this issue by sealing around both the nose and the mouth. Since nasal bridge anthropometry varies greatly between patients, the soft patient contacting portion or cushion must adapt to the shapes of individual patients. Typically this is not achieved for the entire range of patients and some form of leak occurs. The problem is heightened during sleep when the jaw moves and the head position changes. This action can often serve to dislodge the mask and cause leak. Since leak can be noisy and results in less-effective treatment, users often compensate by tightening the headgear more than is required. This is detrimental for patient comfort and can cause skin breakdown.

A further problem encountered by patients who are using full face, nasal or nose and mouth masks is that the portion of the patient interface that seals around the nasal bridge prevents the patient from wearing spectacles. Additionally it may give the sensation of being closed in, leading to a feeling of claustrophobia, particularly when combined with a mouth-sealing portion. A further disadvantage is that any leaks that may occur can affect the sensitive area surrounding the eyes.

One form of nasal assembly known as a nasal puff is described in U.S. Pat. No. 4,782,832 (Trimble et al.). This device has a pair of nasal puffs together with a plenum chamber held in place with a harness assembly adapted to be worn over the head of the patient. The device does not provide a mouth seal.

Another form of known nozzle assembly is described in U.S. Pat. No. 6,431,172 (Bordewick et al.). The patent discloses a device with nares elements mounted on an inflatable plenum chamber. Again this does not provide any structure for sealing the mouth.

One typical example of a known nasal mask is described in U.S. Pat. No. 5,243,971 (Sullivan et al.). This has a ballooning seal in order to fit the patient's nose and facial contours but does not provide a mouth seal. The contents of this patent are hereby incorporated by cross-reference.

International publication number WO 01/97893 A1 (Frater et al.), the content of which is hereby incorporated by cross-reference, describes a mask system for delivering air to a user including a suspension mechanism. This suspension mechanism allows relative movement between a face-contacting portion and a mask shell.

A known example of a full face mask is described in U.S. Pat. No. 6,513,526 B2 (Kwok et al.), incorporated herein by reference in its entirety. Whilst providing a facial contour and sealing mechanism that incorporates both the nasal and mouth, this mask cannot flex to adapt to changes in jaw movement and head position throughout the night.

A known example of a nose and mouth mask is described in U.S. Pat. No. 5,560,354 (Berthon-Jones et al.), the content of which is hereby incorporated by cross-reference.

U.S. Patent Publication No. 2002/0069872 A1 (Gradon et al.) describes a mouthpiece which seals the oral cavity against 'mouth leak'. This mouthpiece includes both intra-oral and extra-oral sealing means and can be kept in place without the need for straps. International patent WO 01/95965 (Gradon et al.) describes a similar mouthpiece for supplying humidified gases to a user.

U.S. Pat. No. 6,571,798 B1 (Thornton) describes an oral device for improving a patient's breathing together with a connecting post that provides a standard interface to a CPAP patient interface. The oral device is said to extend the lower jaw of the patient and thus open the breathing passage. The oral device is clenched between the teeth which may lead to discomfort and if mask pressures are high can lead to the slow creep of gums around the teeth due to the sustained load.

U.S. Pat. No. 1,873,160 (Sturtevant) describes a cylindrical air chamber held in position by a mouth portion that extends between the lips and teeth. The mouth portion may prove irritating and lead to discomfort when used for long periods.

A problem with patient interfaces which incorporate oral appliances is that they can be uncomfortable for patients. Therefore, a need has developed in the art to address the problems of the prior art.

SUMMARY OF THE INVENTION

In accordance with a first aspect of the invention there is provided a comfortable, effective patient interface which provides a supply of air or breathable gas to a patient's nasal passages and which prevents or reduces mouth leak.

In accordance with a second aspect of the invention there is provided a patient interface which can accommodate movement of the jaw of the patient.

In accordance with another aspect of the invention there is provided a patient interface that provides an effective seal with both the patient's mouth and the patient's nasal passages.

In one form the invention comprises a mouth covering chamber, a nozzle assembly and a structure to provide flexibility therebetween.

Another aspect of the invention relates to reducing contact area when compared to most known full face masks. This allows a far reduced headgear tension to be applied, significantly improving patient comfort. Patient comfort is further enhanced since the patient is less likely to feel claustrophobic, particularly with the removal of any mass that is close to the eyes.

In accordance with another aspect of the invention there is provided a patient interface adapted to connect to an air delivery conduit.

In accordance with another aspect of the invention there is provided a patient interface comprising a first chamber which incorporates a mouth covering chamber, a second chamber which incorporates a nozzle assembly and a flexible element connecting the first and second chambers.

In accordance with another aspect of the invention there is provided a patient interface comprising a mouth covering chamber, a pair of nozzles and a flexible attachment member therebetween.

In accordance with yet another aspect of the invention there is provided a patient interface comprising a mouth covering chamber and a pair of nozzles flexibly attached thereto. The mouth covering chamber incorporates a rigid portion defining the mouth covering chamber and a resilient or compliant patient-contacting portion. The pair of nozzles are mounted upon the patient-contacting portion.

In accordance with yet another aspect of the invention there is provided a patient interface comprising a mouth receiving assembly and a pair of nozzles flexibly attached thereto. The mouth receiving assembly incorporates a rigid portion defining a mouth covering chamber, a gusset portion and a patient-contacting portion. The pair of nozzles are mounted upon a flexible component of the patient-contacting portion.

In accordance with yet another aspect of the invention there is provided a patient interface with a strap routed around the top of the ears.

These and other aspects of the invention will be described in or apparent from the following detailed description of preferred embodiments, in which like elements designate like parts.

BRIEF DESCRIPTION OF THE DRAWINGS

FIGS. 1a-d show a dual chamber patient interface in accordance with a first embodiment of the invention;

FIGS. 2a-c show a dual chamber patient interface in accordance with a second embodiment of the invention;

FIGS. 3a-c show a dual chamber patient interface in accordance with a third embodiment of the invention;

FIGS. 7a-b show views of a single chamber patient interface with mouth gusset portion in accordance with a further embodiment of the invention;

FIGS. 13-18d illustrate another embodiment of a single chamber patient interface;

FIGS. 31-33c illustrate another embodiment of a single chamber patient interface with a gusset portion;

FIGS. 34-38 illustrate embodiments of a single chamber patient interface with insertable nozzles;

FIGS. 43-56b illustrate embodiments of nozzle arrangements;

FIGS. 57-62 illustrate embodiments of support members for nozzles;

FIG. 65a-65c illustrates an embodiment of a patient interface with an extended frame;

FIGS. 66a-67 illustrate an embodiment of a patient interface with an insertable anti-asphyxia valve; and FIGS. 68-80 illustrate embodiments of headgear assemblies.

DETAILED DESCRIPTION OF PREFERRED EMBODIMENTS

Figure 1A:
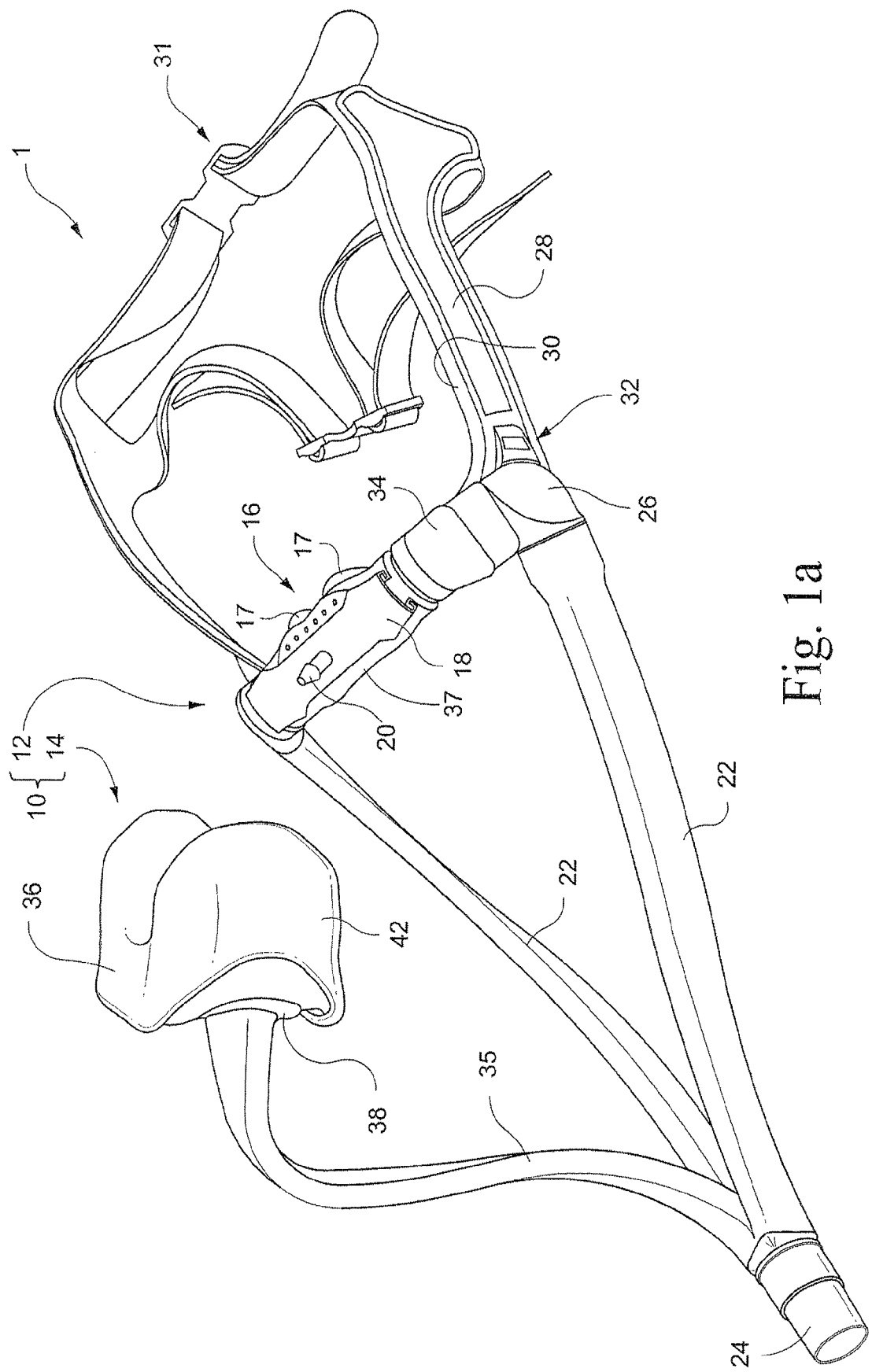
Figure 1B:
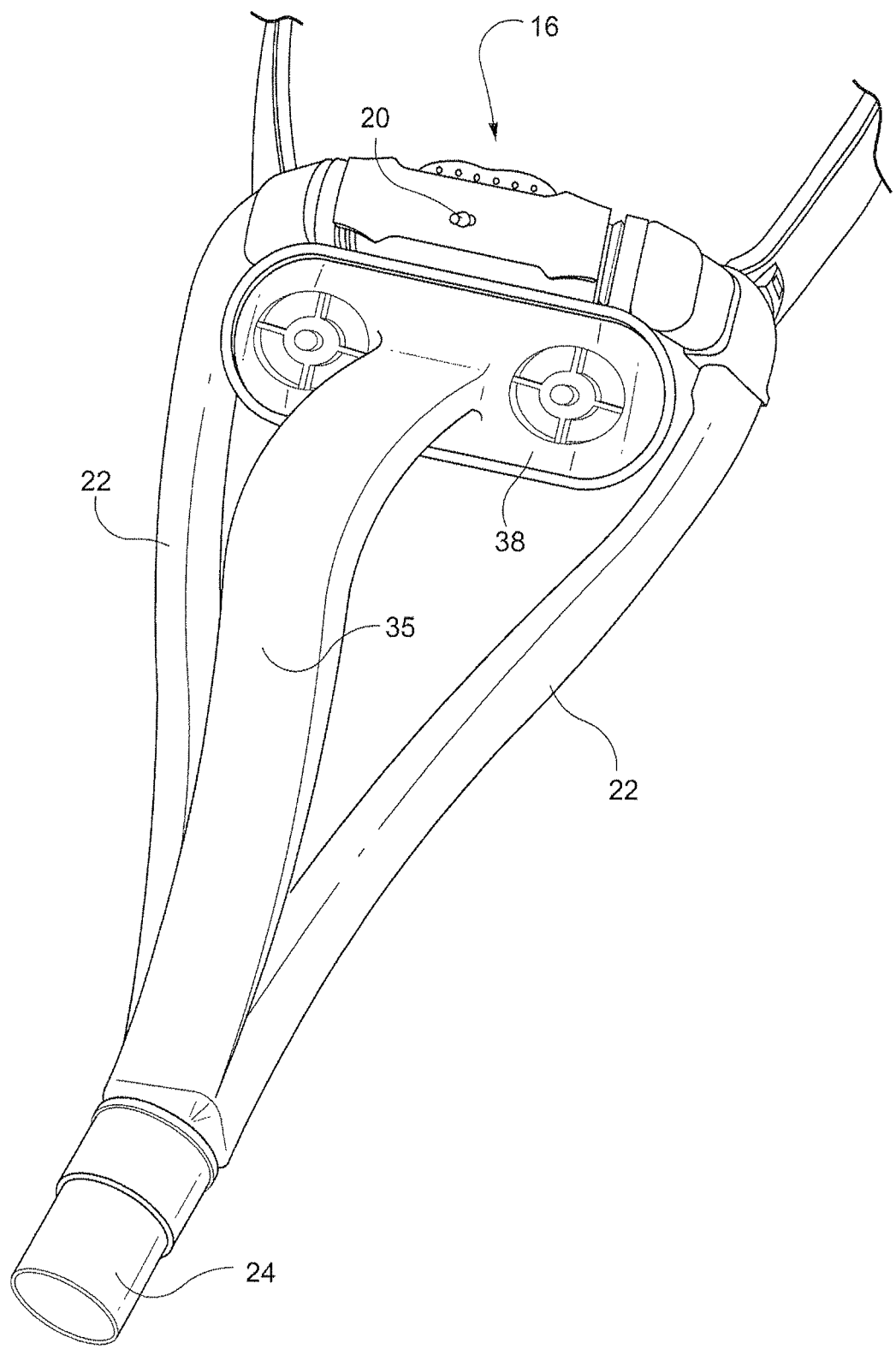
Figure 1C:
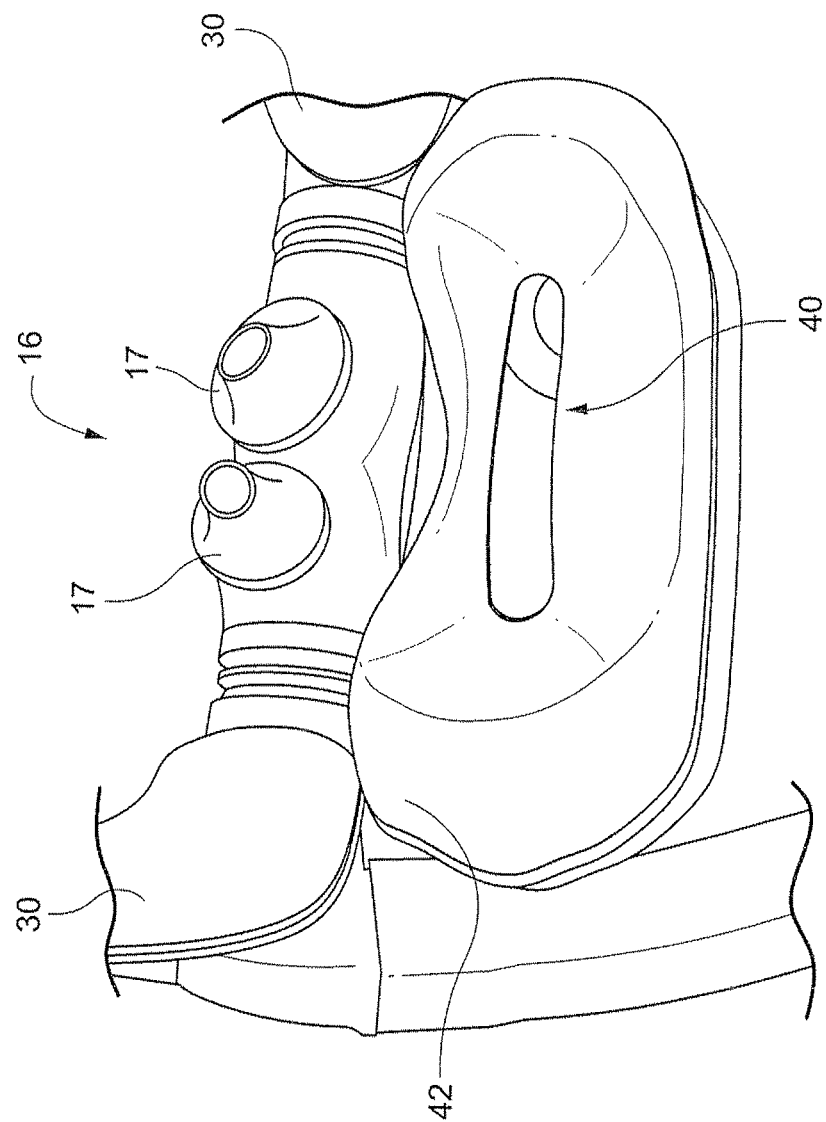

FIGS. 1a-1d illustrate a first embodiment of the present invention. As shown in FIG. 1a, a headgear assembly 1 includes a patient interface having a dual chamber assembly 10 including an upper chamber 12 and a lower chamber 14. As shown in FIG. 1a, the lower chamber 14 is in a disconnected position, while FIGS. 1b-1d shown the upper and lower chambers in a connected position.

Referring to FIG. 1a, the upper chamber 12 includes a nozzle assembly 16 supported by a frame including a first connector on each lateral end thereof, as described in U.S. Pat. No. 7,318,437 and incorporated herein by reference in its entirety. The nozzle assembly 16 is secured to the frame via a clip 18 which in this embodiment supports a pressure measurement port 20. The nozzle assembly 16 may include a pair of nozzles 17 (see FIGS. 1c and 1d).

One or more inlet conduits 22 is supplied with breathable gas under pressure via a joint 24 coupled to an air delivery tube, which in turn is communicated with a blower or air delivery device. The lower chamber 14 is connected to the joint 24 via an inlet conduit 35. The joint 24 may include three branches (see FIG. 1b) for connection to the inlet conduits 22 and 35.

Each inlet conduit 22 is connected to an elbow connector 26, which is preferably connected to yoke 28 of strap 30 of headgear assembly 31 via a locking portion 32. Each elbow connector 26 is coupled to a second connector 34. Each respective first connector of the frame may be selectively rotated with respect to the second connectors 34 to allow the nozzle assembly 16 to be adjusted according to patient requirements, to achieve the best fit.

Figure 1E:
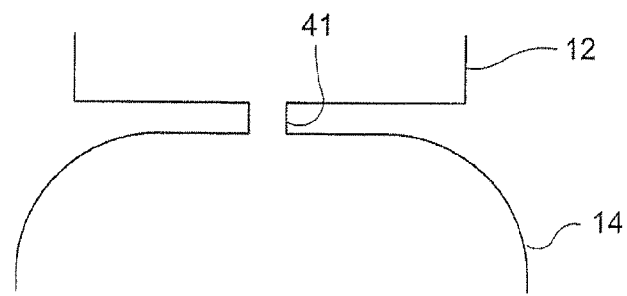
FIGS. 1e-1h illustrate various embodiments as to connection between the upper and lower chambers.
Figure 1F:
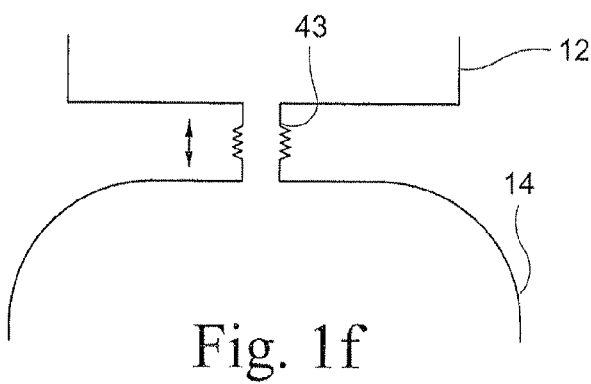
Figure 1G:
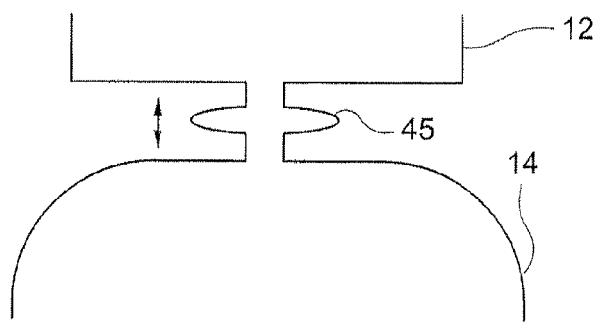
Figure 1H:
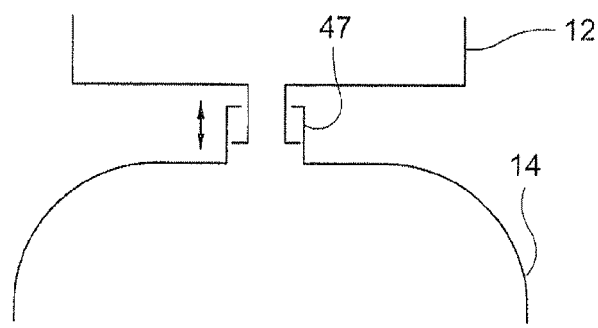

As best shown in FIG. 1a, where the upper and lower chambers are disassembled, a first portion 36 of the lower chamber 14 may be connected to a second portion 37 of the upper chamber 12. Connection may be achieved via a conduit 41 (See FIG. 1e), or preferably a flexible element that connects the upper chamber 12 to the lower chamber 14. The flexible element may comprise one or more thin silicone conduits through which air can pass. It may take the form of any other flexible element through which air can pass however, examples including a spring 43 (FIG. 1f), bellows 45 (FIG. 1g) or piston mechanism 47 (FIG. 1h). The flexible element provides a range of adjustment to adapt to the different geometry of a wide range of patients and in addition allow for any movement of their jaw and head position during sleep. The conduit need not be flexible if adjustment can occur via flexibility of the cushions of the upper and lower chambers.

Connection between the upper and lower chambers may take several forms, keeping in mind that one main purpose is to maintain the position of the upper chamber 14 relative to the patient's mouth. To that end, the connection may take the form of a mechanical fastener, such as VELCRO®, snaps, connectors, etc. For example, the top or second portion 37 of the upper chamber 14 may include a hook portion of VELCRO®, while the bottom or first portion 36 of the upper chamber 12 may include the loop portion of VELCRO®. In other forms, the connection may be provided via metal or plastic rivets and/or by use of adhesives. In the case of rivets, flexibility could be provided by virtue of the compliant and flexible portions of the cushions of the respective upper and lower chambers that are fastened together. In other forms, the lower chamber 14 may be connected to a portion of the headgear or to the inlet tubes 22. Moreover, it is not necessary that air can pass between the upper and lower chambers 12, 14, as each has an independent source of pressurized air.

As shown in FIGS. 1a-1d, the lower chamber 14 includes a rigid polycarbonate frame 38 which defines a mouth covering chamber 40 (see FIG. 1c) and a soft (e.g., compliant, resilient) silicone cushion 42 which contacts the patient and forms a seal. The lower chamber 14 closely resembles the mouth chamber and mouth cushion described in U.S. Pat. No. 5,560,354, the contents of which are hereby incorporated by cross-reference. However it may take a variety of forms, such as described in U.S. Provisional Patent application No. 60/483,622 filed 1 Jul. 2003. The cushion 42 may be attached to the frame 38 by connecting a base edge of the cushion 42 to the frame 38, e.g., via adhesives and/or a tongue and groove arrangement. In another form, connection may be achieved by stretching the cushion 42 over the outer edge of the frame 38.

The inlet conduit 35 is structured to deliver breathable gas into the lower chamber 14. The inlet conduit 35 may be inserted into an aperture of the frame 38, in which case the tube 35 may be held in place by friction alone, as best shown in FIGS. 1b and 1d. Alternatively, the inlet conduit 35 may be connected to a swivel assembly (not shown) which in turn is connected to the frame 38. In another alternative, one or more suitable headgear straps (not shown) can be used to support the lower chamber 14 such that it can move or pivot relative to the upper chamber without the need for connection thereto or a flexible element.

Figure 2B:
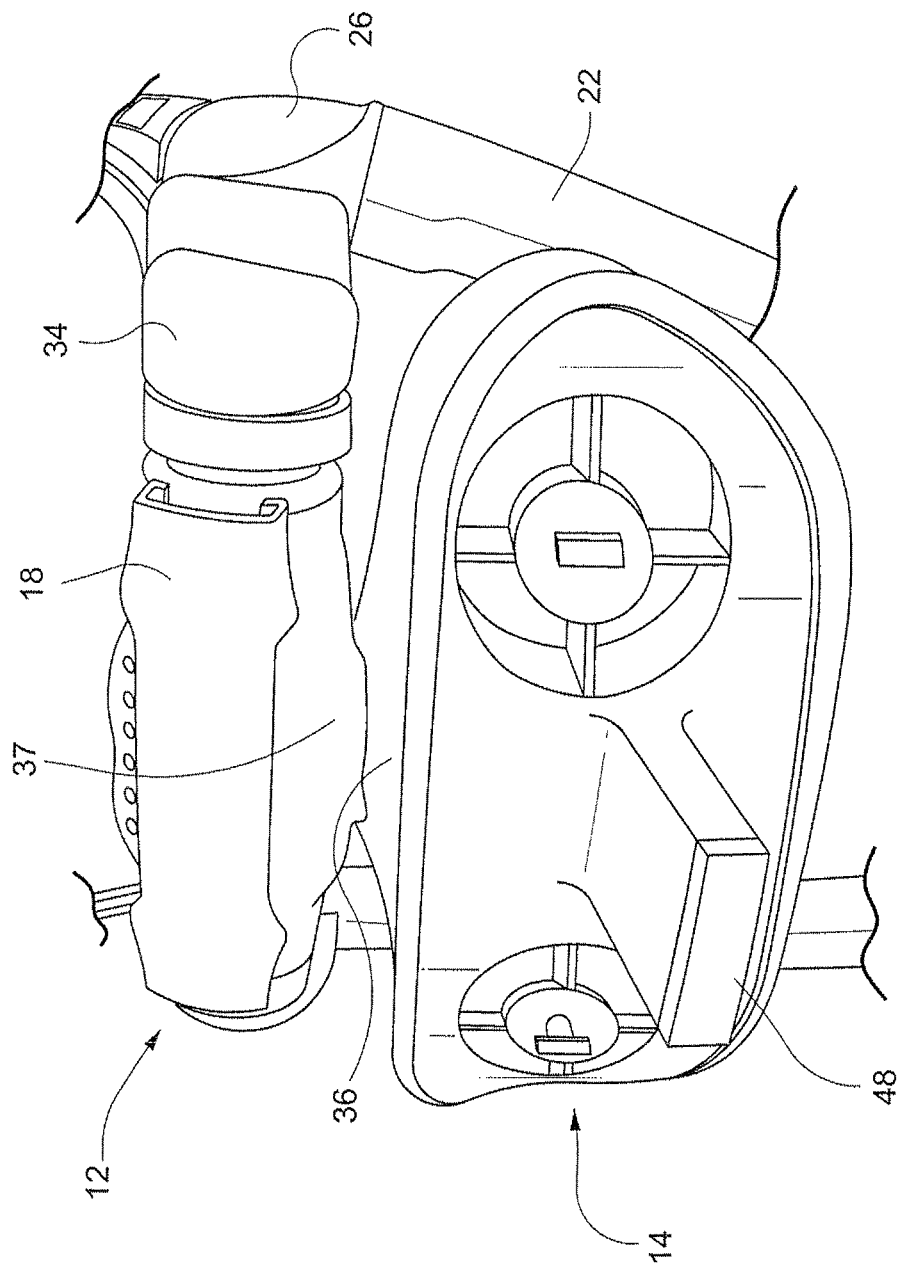

FIGS. 2a and 2b show a second embodiment of the invention. In this embodiment, the lower chamber 14 does not have a direct inlet conduit, like the inlet conduit 35 in FIG. 1a, but instead the air is directed to the upper chamber 12 via the inlet conduits 22 only. Air travels through the flexible element, i.e., through first and second surfaces 36 and 37, from the upper chamber 12 to the lower chamber 14, for example, thus allowing both nose and mouth breathing. FIG. 2b best showed the position where the flexible element would be located between the first and second surfaces 36, 37.

Figure 2C:
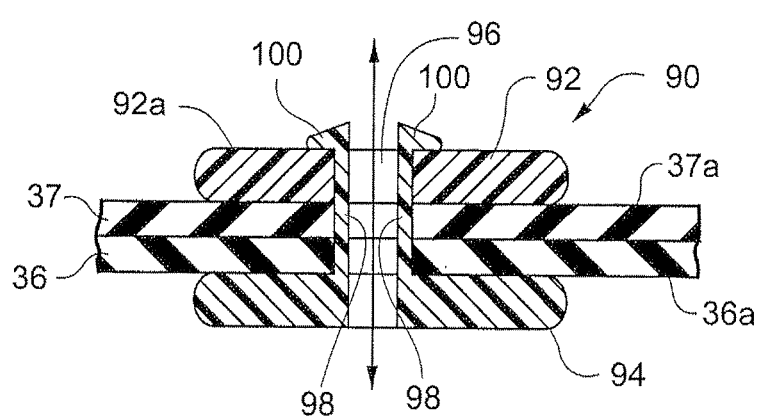

FIG. 2c shows one example of how the upper and lower chambers 12, 14 may communicate with one another. A mechanical fastener 90 includes first and second parts 92 and 94. The first part 92 may take the form of a thin plate attached to an inside surface 37a of the second part 37 formed on the upper chamber 12. The first part includes an aperture 96. The second part 94 may include a thin plate positioned on the inside surface 36a of the first part 36 formed on the lower chamber 14. The second part 94 includes one and preferably a plurality of arms 98 extending through the upper and lower chambers 12, 14. The arms 98 are resiliently flexible so that shoulder 100 on each arm 98 may be secured against a top surface 92a of the first part, thereby locking the entire assembly together while allowing gas to flow between the upper and lower chambers 12, 14. The arms 98 may be formed so as to cut through the upper and lower chambers 12, 14 upon assembly, thereby creating the through hole. The assembly may provide for multiple holes if desired.

In FIGS. 2a and 2b, a plug 48 covers an aperture of the frame 38 where an inlet conduit could be placed. Therefore, the joint 24 in FIG. 1a need not include a separate branch for the conduit 35, or the branch could be plugged.

Figure 3A:
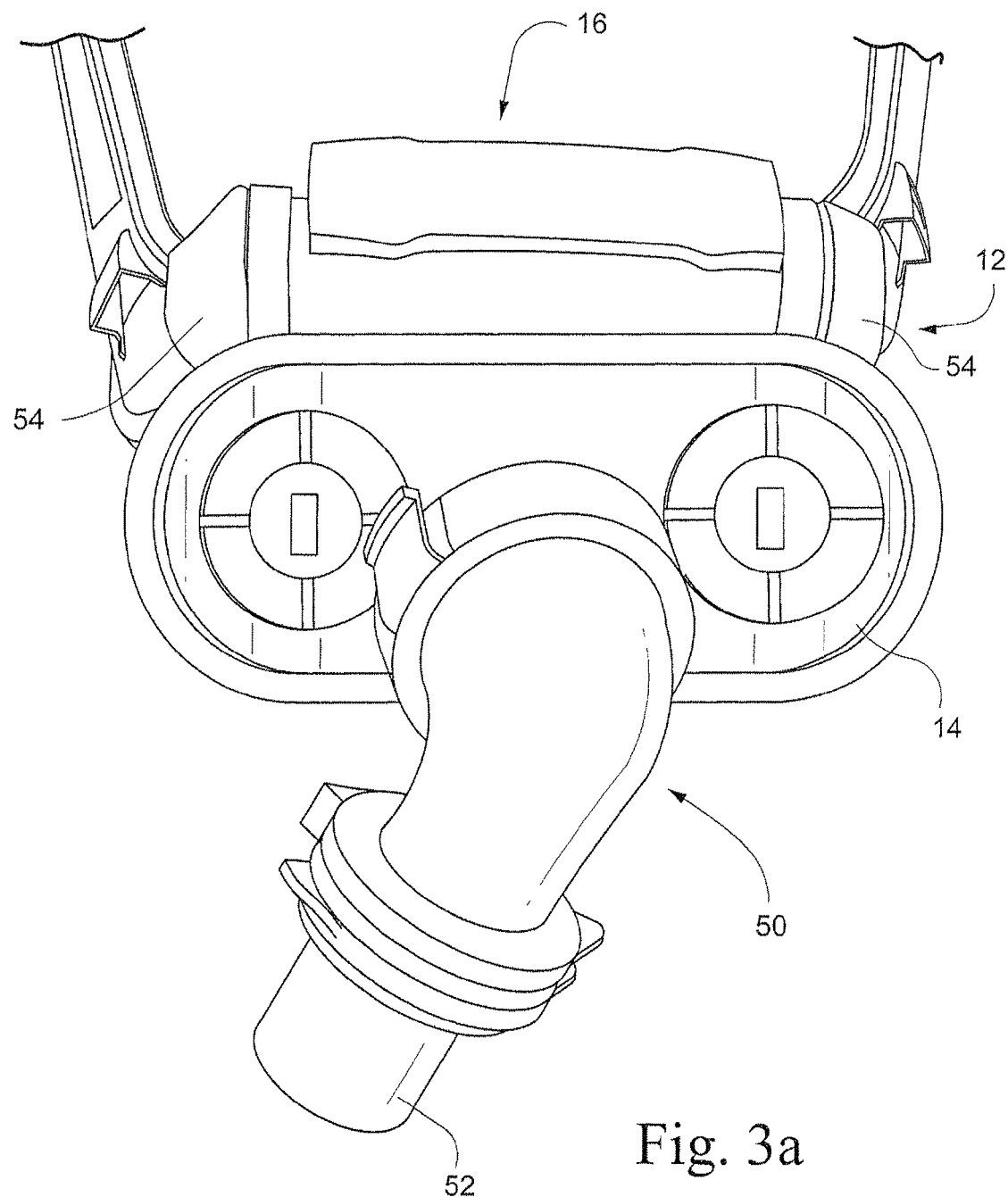
Figure 3C:
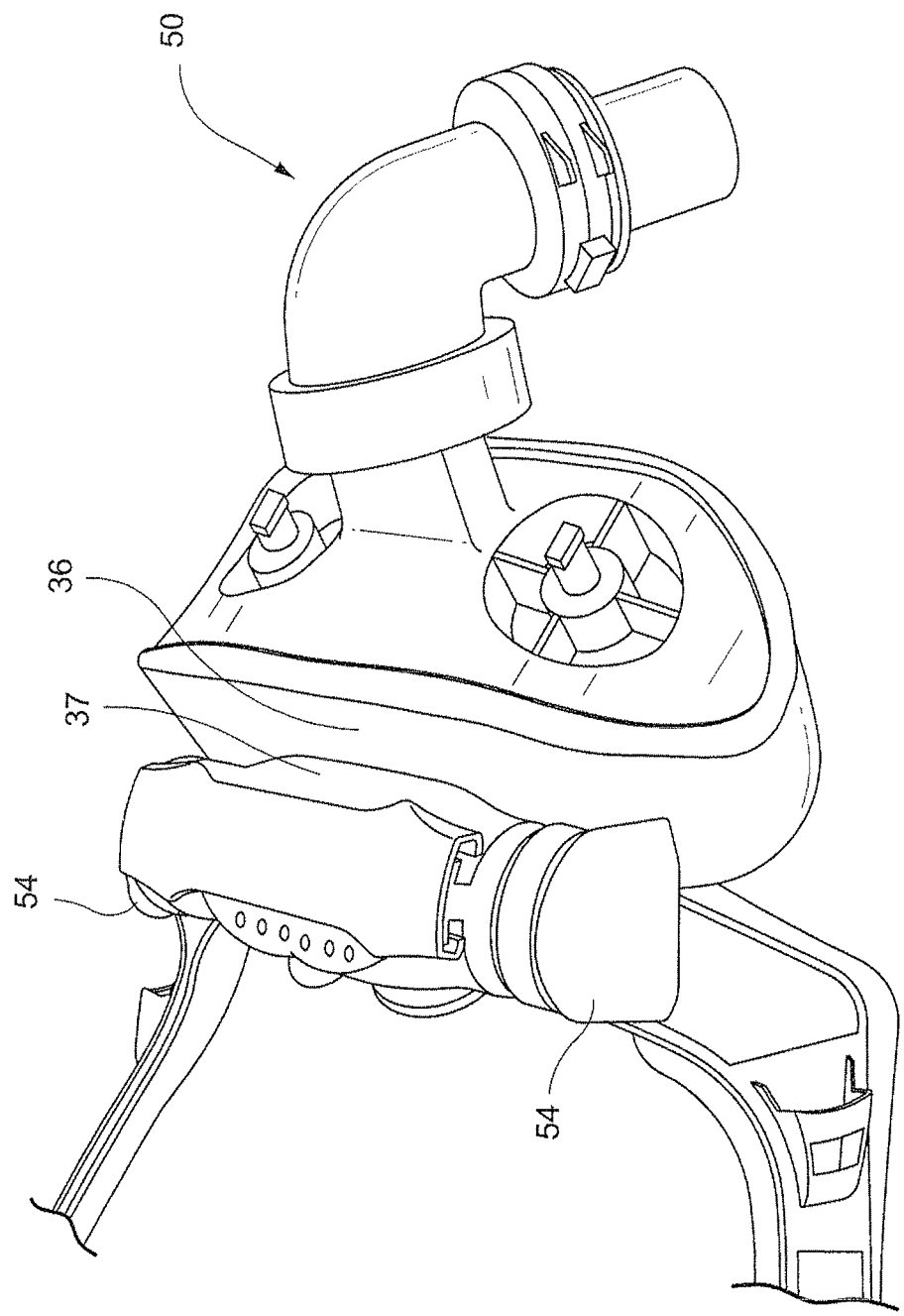

In a third embodiment of the invention, as shown in FIGS. 3a and 3b, inlet air is directed directly to the lower chamber 14 through a swivel assembly 50. The upper chamber 12 does not have any inlet conduits but instead the air is directed to the upper chamber 12 by traveling through a conduit extending from the first surface 36 to the second surface 37. The use of a swivel assembly 50 has the advantage that the inlet conduit (not shown, but connected to end 52 of swivel assembly 50) can be routed from any direction. Further, nozzle assembly 16 need not be provided with second connectors 34 and elbow connectors 26 as shown in FIG. 1a. Instead, a pair of plugs 54 may be placed into each end of the nozzle assembly 16, as described in U.S. Pat. No. 7,318,437 and entitled "Nasal Assembly", incorporated herein by reference in its entirety.

Figure 4A:
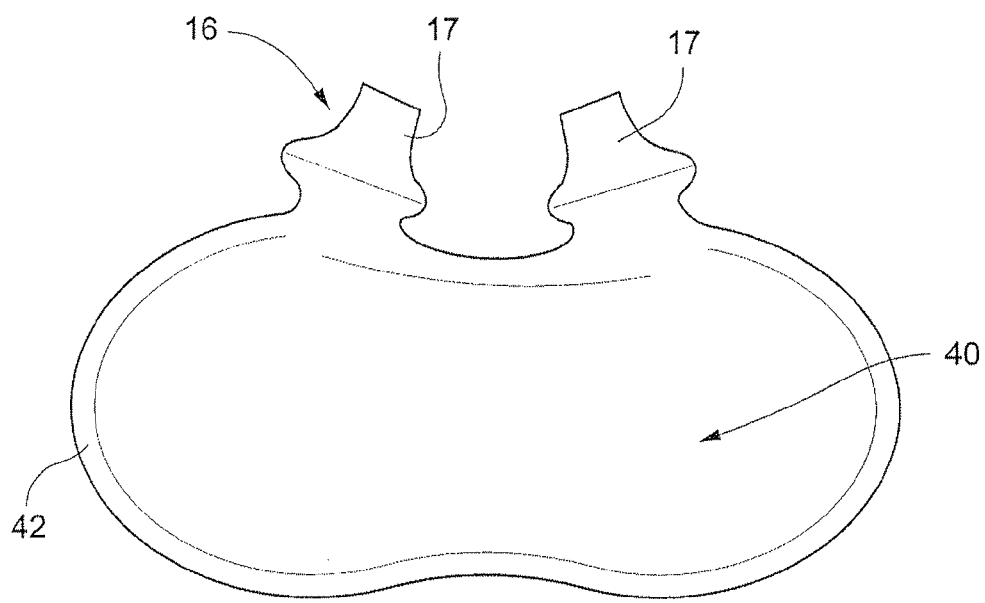
FIGS. 4a-c show a single chamber patient interface in accordance with a further embodiment of the invention.
Figures 4B, 4C:
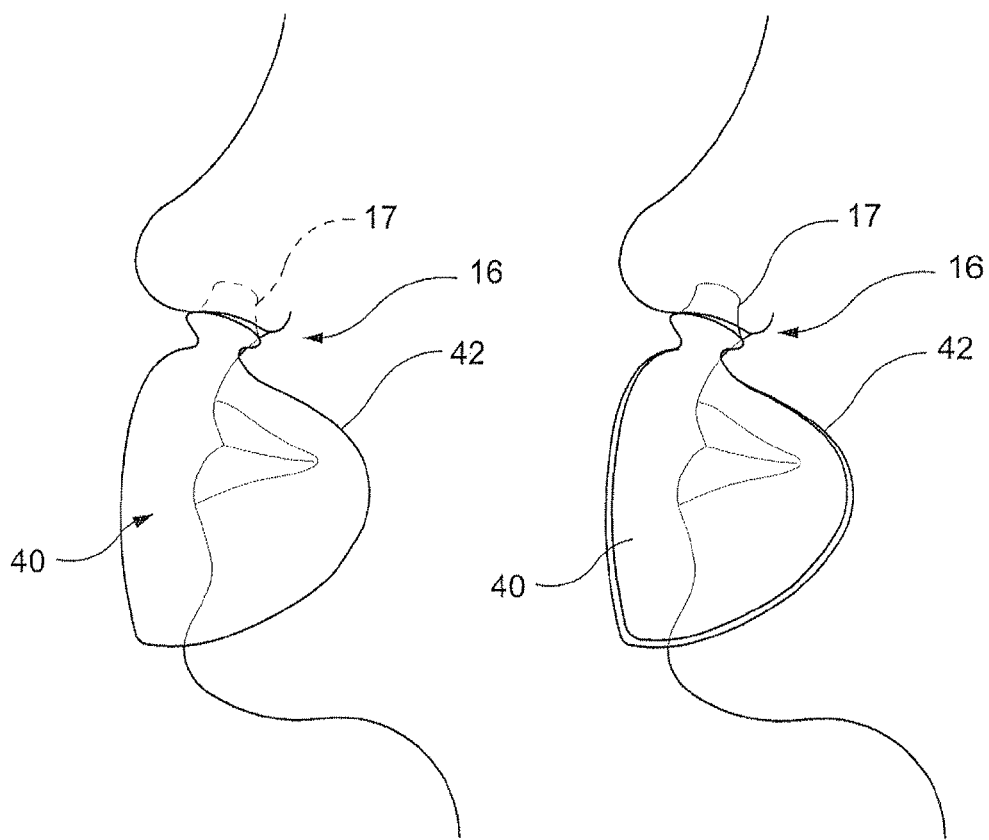

FIGS. 4a-c schematically show a fourth embodiment of the invention. In this embodiment, the mouth covering chamber 40 and the nozzle assembly 16 form one chamber with inherent flexibility of the soft silicone cushion 42 upon which the nozzles 17 are mounted providing for movement and changes in alignment between the two. This embodiment of the invention achieves the advantage of minimizing the volume of the patient interface which is positioned between the nares and the upper lip.

Figure 5A:
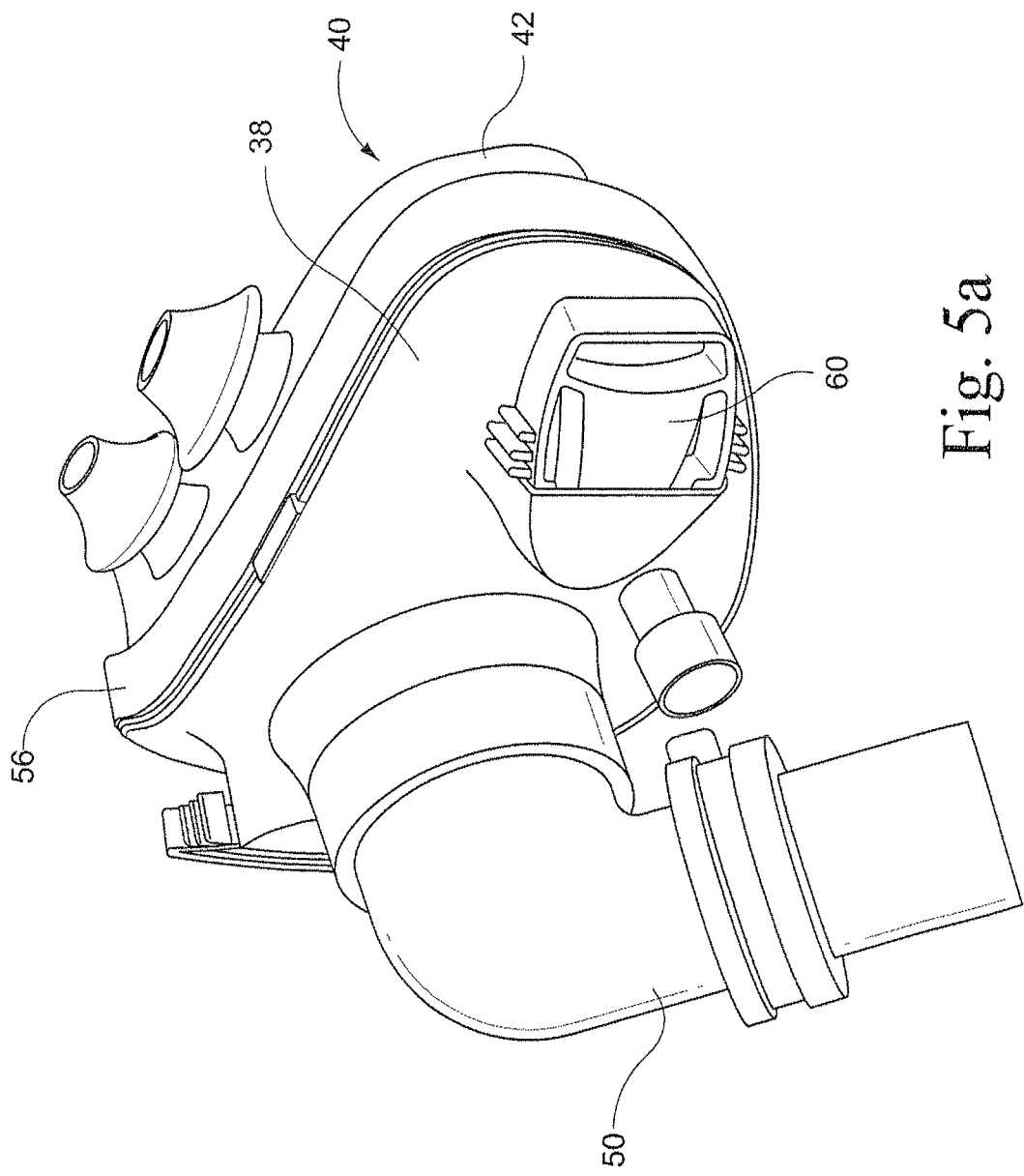
FIGS. 5a-d show front and rear views of a further embodiment of the invention.
Figure 5B:
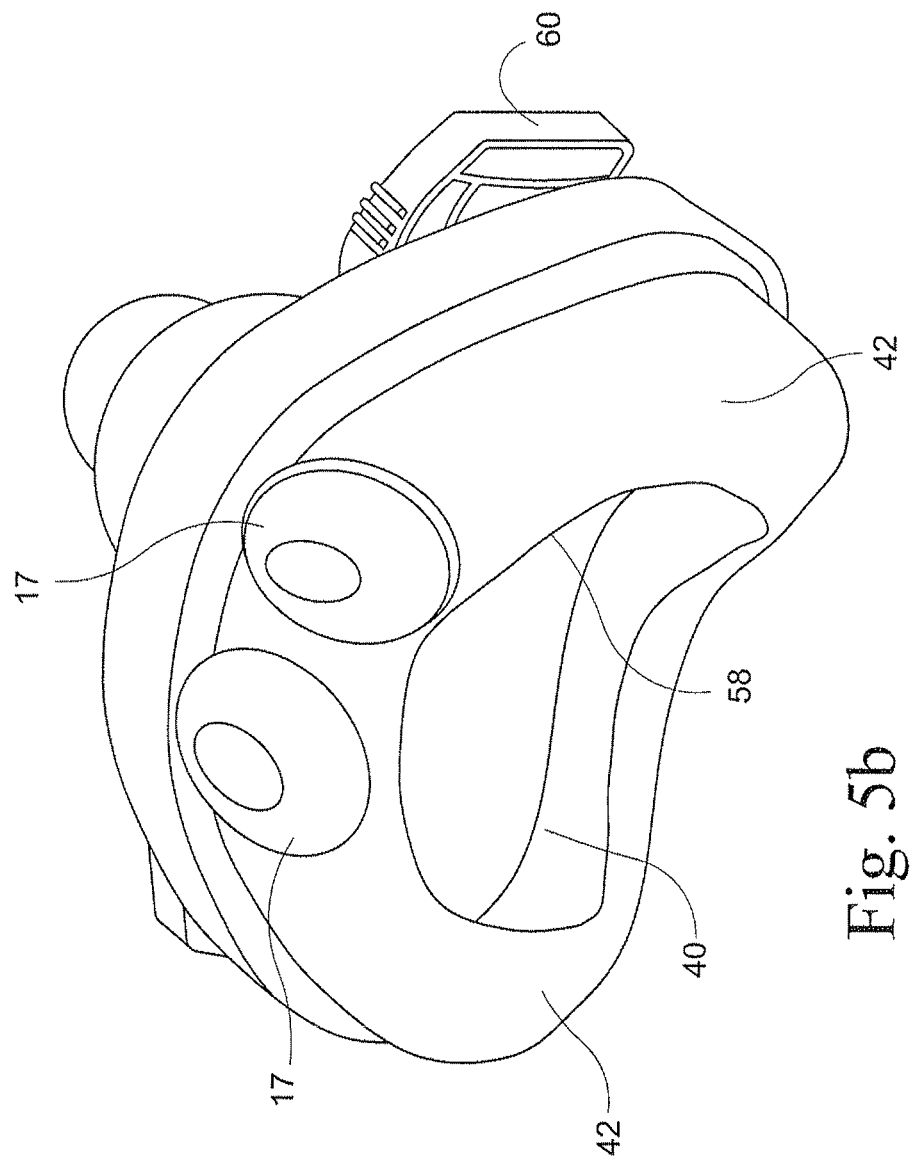
Figure 5C:
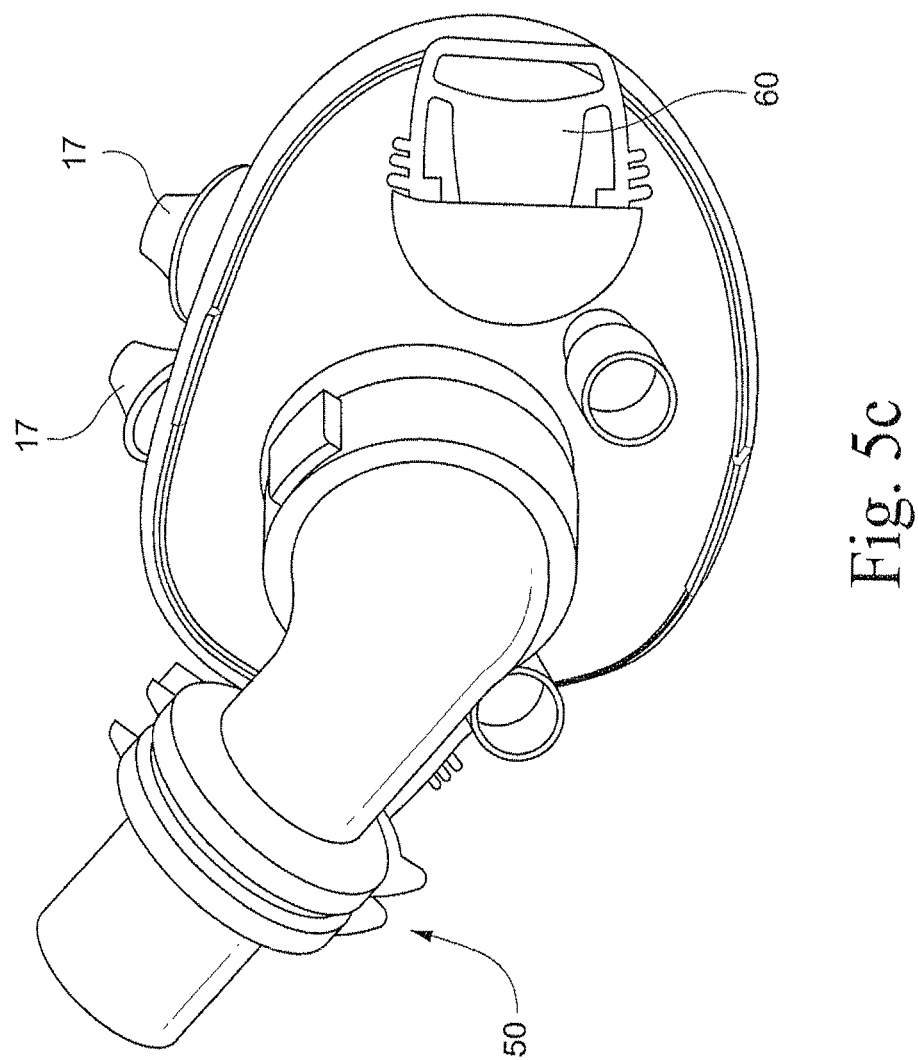
Figure 5D:
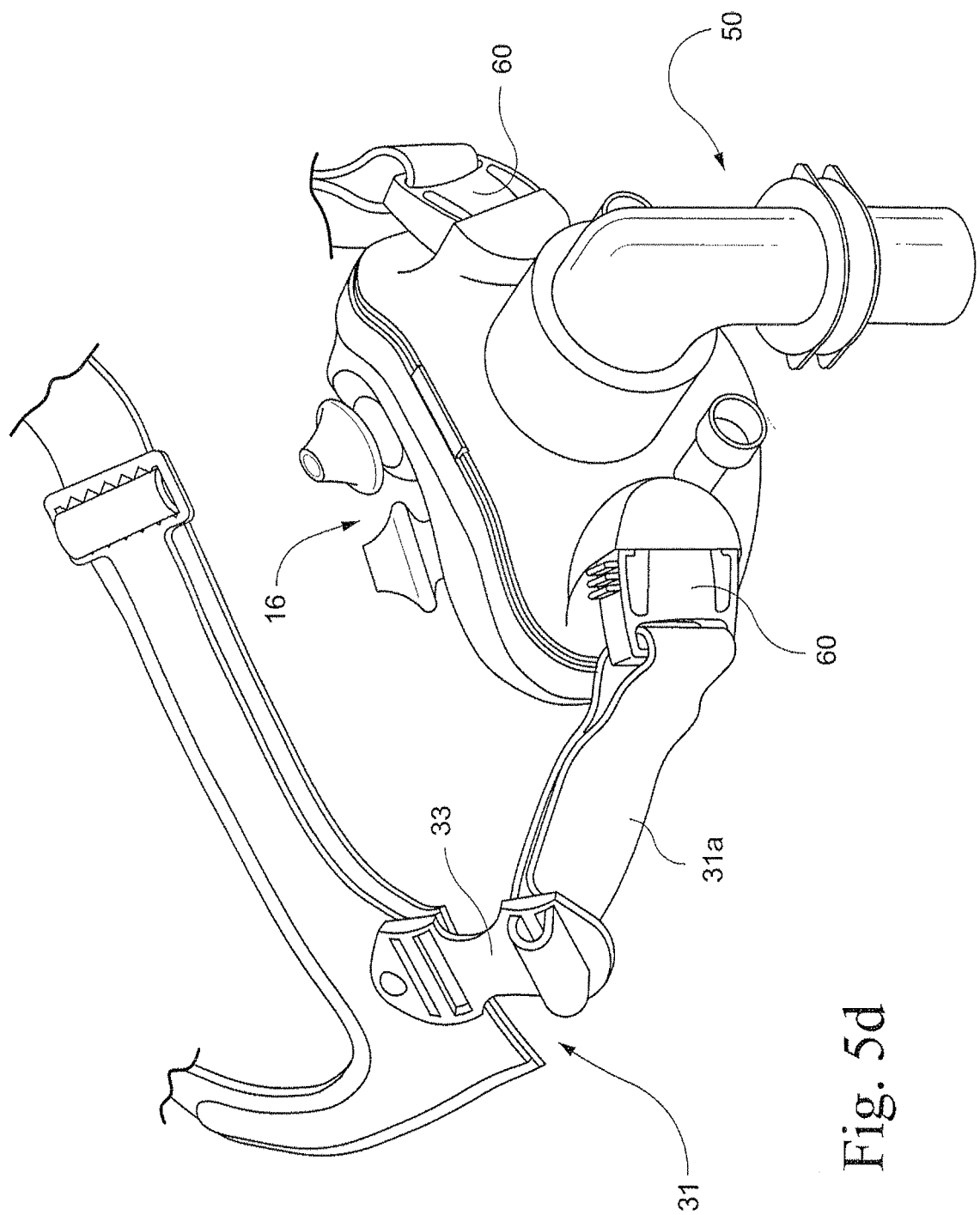

FIGS. 5a-5d illustrate yet another embodiment of the invention. As can be seen from FIG. 5a, a swivel assembly 50 provides air from an air delivery tube (not shown) and supplies it to the mouth covering chamber 40 (best shown in FIG. 5b). The cushion 42 is connected to the rigid frame 38 of the mouth covering chamber 40 via a cushion clip 56. As best shown in FIG. 5b, the nozzles 17 are connected or provided directly to the outer face contacting portion of the cushion 42 which takes the form of a thin silicone membrane 58. The membrane 58 performs the dual function of forming a seal around the lips of a patient and additionally supporting the nozzles 17. The inherent flexibility of the membrane 58 provides a range of adjustment to adapt to the different geometry of a wide range of patients and in addition allows for any movement of their jaw and head position during sleep. It should be noted that whilst this embodiment describes nozzles (which may be in the form of nasal pillows, nasal prongs, cannula, or nasal puffs) 17 of a similar form to those disclosed in U.S. Pat. No. 7,318,437, the contents of which are hereby incorporated by cross-reference, they may take the form of any nasal prongs insertable into each nare. As shown in FIG. 5d, the patient interface can easily be attached via clips 60 to a headgear assembly 31 in order to secure the patient interface to the patient. The headgear 31 includes an intermediate strap 31a extending between clip 60 and connector 33. The clip 60 and its connection to frame 30 resemble the clip/frame described in U.S. Patent Application Publication 2004/0112384 A1, incorporated herein by reference in its entirety.

Figure 6A:
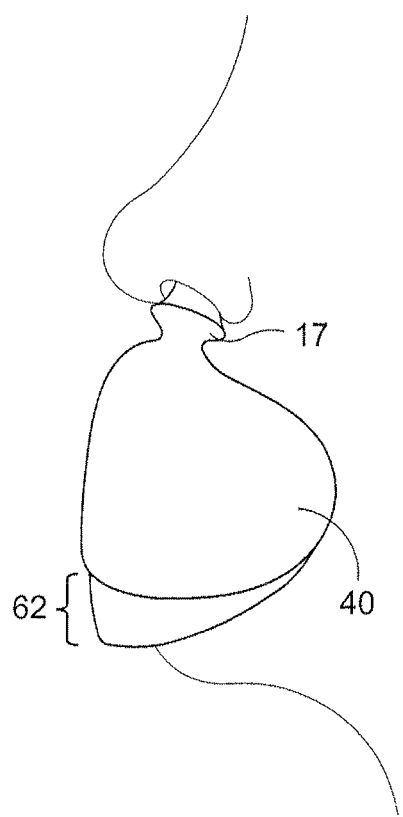
FIGS. 6a-b show a single chamber patient interface with mouth gusset portion in accordance with a further embodiment of the invention.
Figure 6B:
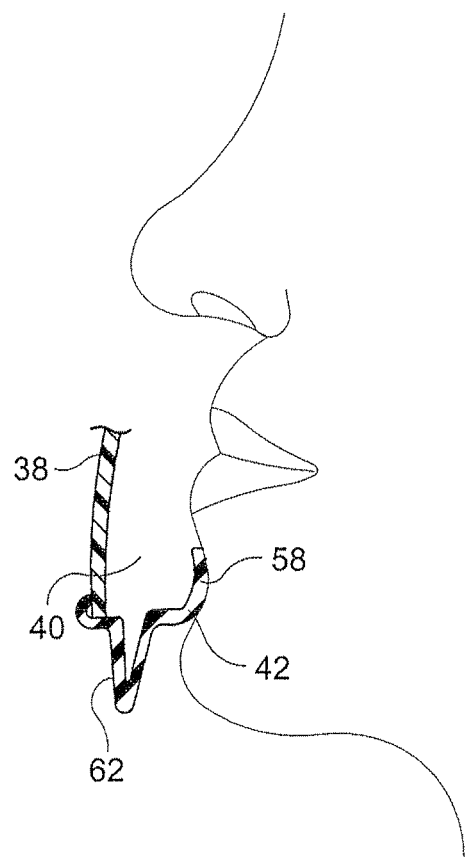

FIGS. 6a-b schematically illustrate a fifth embodiment of the invention. In this embodiment the patient interface includes a mouth covering chamber 40 incorporating a rigid frame 38, a gusset portion 62 and a soft cushion 42. The nozzles 17 are connected directly to the outer face contacting portion of the cushion 42 which takes the form of a thin silicone membrane 58. The gusset portion 62 includes a flexible membrane and has a first side attached to the frame 38 and a second side attached to the cushion 42, as shown in FIG. 6b. Pressure within the patient interface acts upon the increased surface area of the gusset portion 62 projected on the patient's face so as to provide a sealing force for the soft cushion 42 against the patient's face. In addition the gusset portion 62 acts to effectively isolate or decouple the rigid frame 38 from the soft cushion 42. In these respects, the gusset portion 62 acts in a similar manner to that described in International publication number WO 01/97893 A1 (Frater et al.), the content of which is hereby incorporated by cross-reference in its entirety.

Due to its location between the cushion 42 and the frame 38, the gusset portion 62 also acts to decouple the nozzles 17 mounted upon the soft cushion 42 from the rigid frame 38. This provides further flexibility within the patient interface which has the advantages previously described of allowing the interface to adjust to the geometry of different patients and allowing for any jaw or head movement during sleep. A further advantage of the gusset portion 62 is that it allows the face contacting portion, e.g., membrane 58, of the cushion 42 increased freedom to deform in accordance with the contours of the mouth region than does a direct connection between the cushion 42 and rigid frame 38. Thus the cushion 42 may "wrap around" the mouth region as required.

Figure 7A:
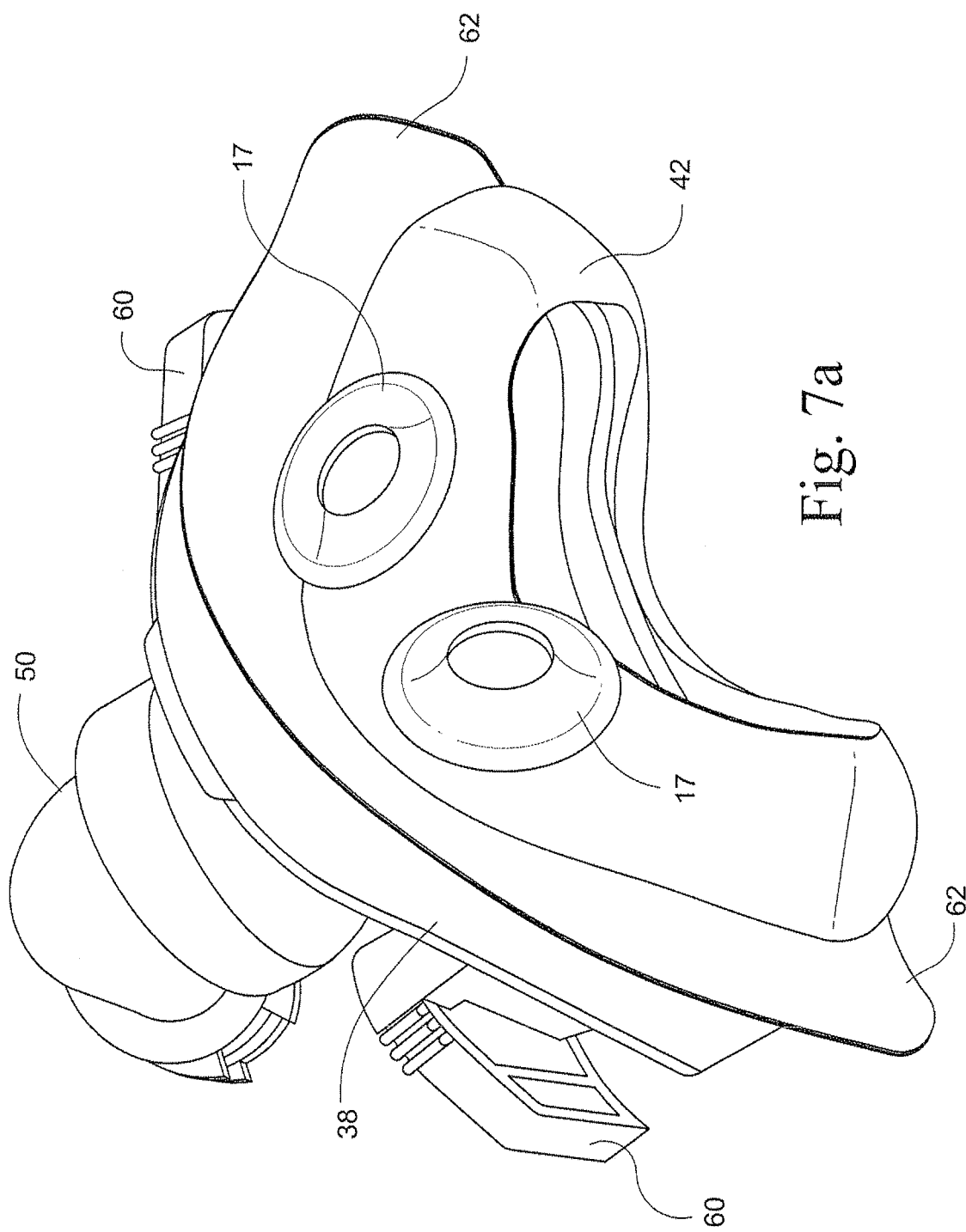
Figure 7C:
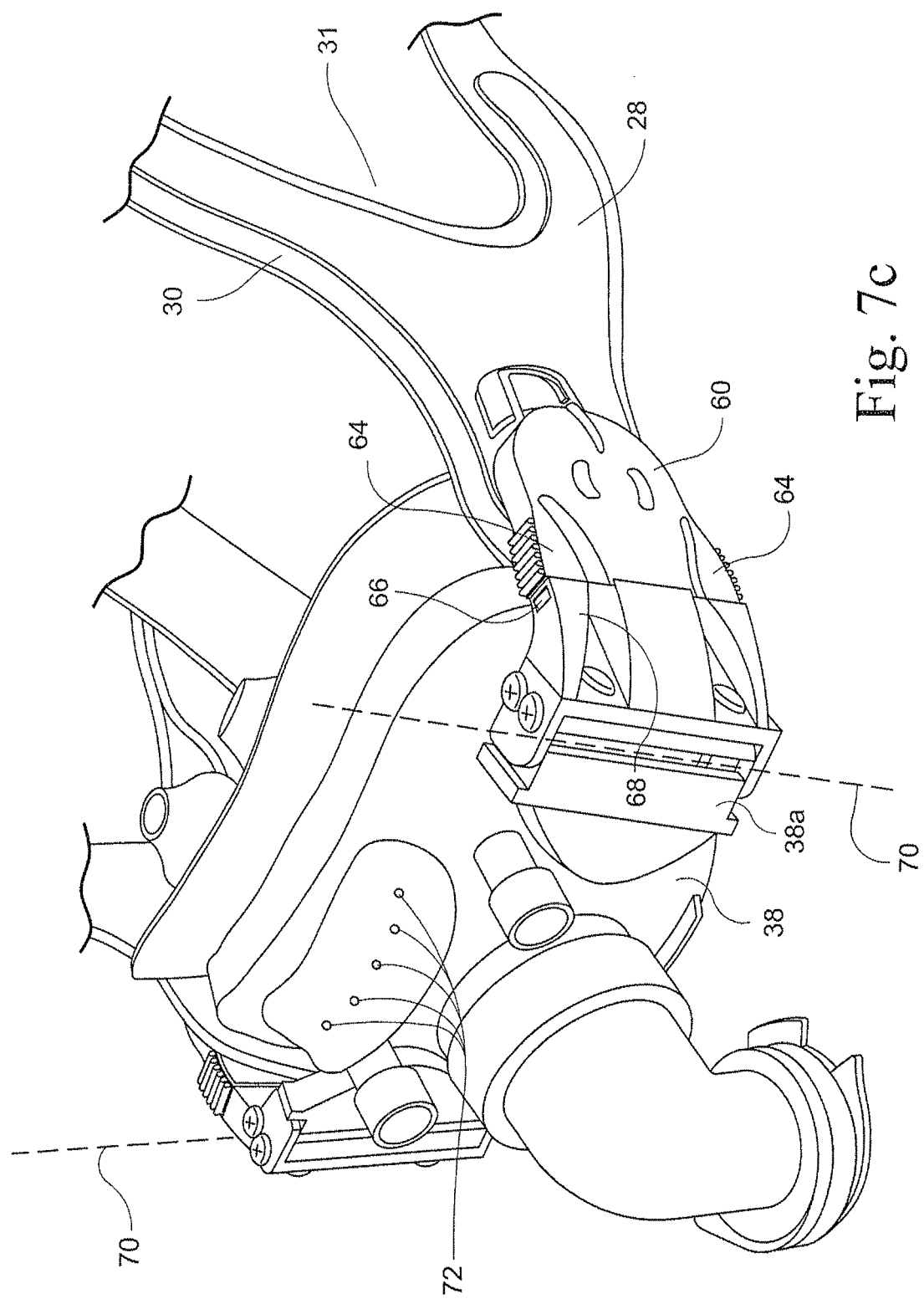
FIGS. 7c-f show views of an alternative embodiment of a single chamber patient interface in accordance with a further embodiment of the present invention.

The gusset portion 62 of the embodiment shown in FIGS. 6a and 6b is a partial gusset portion in that it is arranged at the chin portion of the mouth covering chamber 40. Alternatively the gusset portion 62 may fit around the entire circumference of the rigid frame 38. An embodiment of this is shown in FIGS. 7a-c. As can be seen from FIG. 7a, the embodiment includes an inlet swivel assembly 50, a frame 38, a gusset portion 62 and a soft cushion 42 with nozzles 17 mounted thereon.

FIG. 7b shows the components disassembled, although the swivel assembly 50 and frame 38 are shown in an assembled state that could be disassembled in an alternative embodiment. The headgear clips 60, cushion clip 56 and cushion 42 with gusset portion 62 can also be seen in FIG. 7b. The clip 56 may include one or more resilient tabs 57 that engage with corresponding recesses 59, one of which is shown on frame 38.

Two alternative cushions, 42A and 42B without gussets are displayed in FIG. 7b. It should be noted that each of the nozzles 17 on cushion 42B includes a simple mound rather than containing a single flexible pleat as do the nozzles on cushion 42 and cushion 42A. The nozzles 17 may also include a plurality of corrugations and in general the nozzles may take the form of a nasal puff as described in U.S. Pat. No. 4,782,832 (Trimble et al), or as in other known nasal cannulae, such as prongs that extend into the nares. Further nozzle alternatives are described in U.S. Pat. No. 7,318,437 and entitled "Nasal Assembly."

Figure 7D:
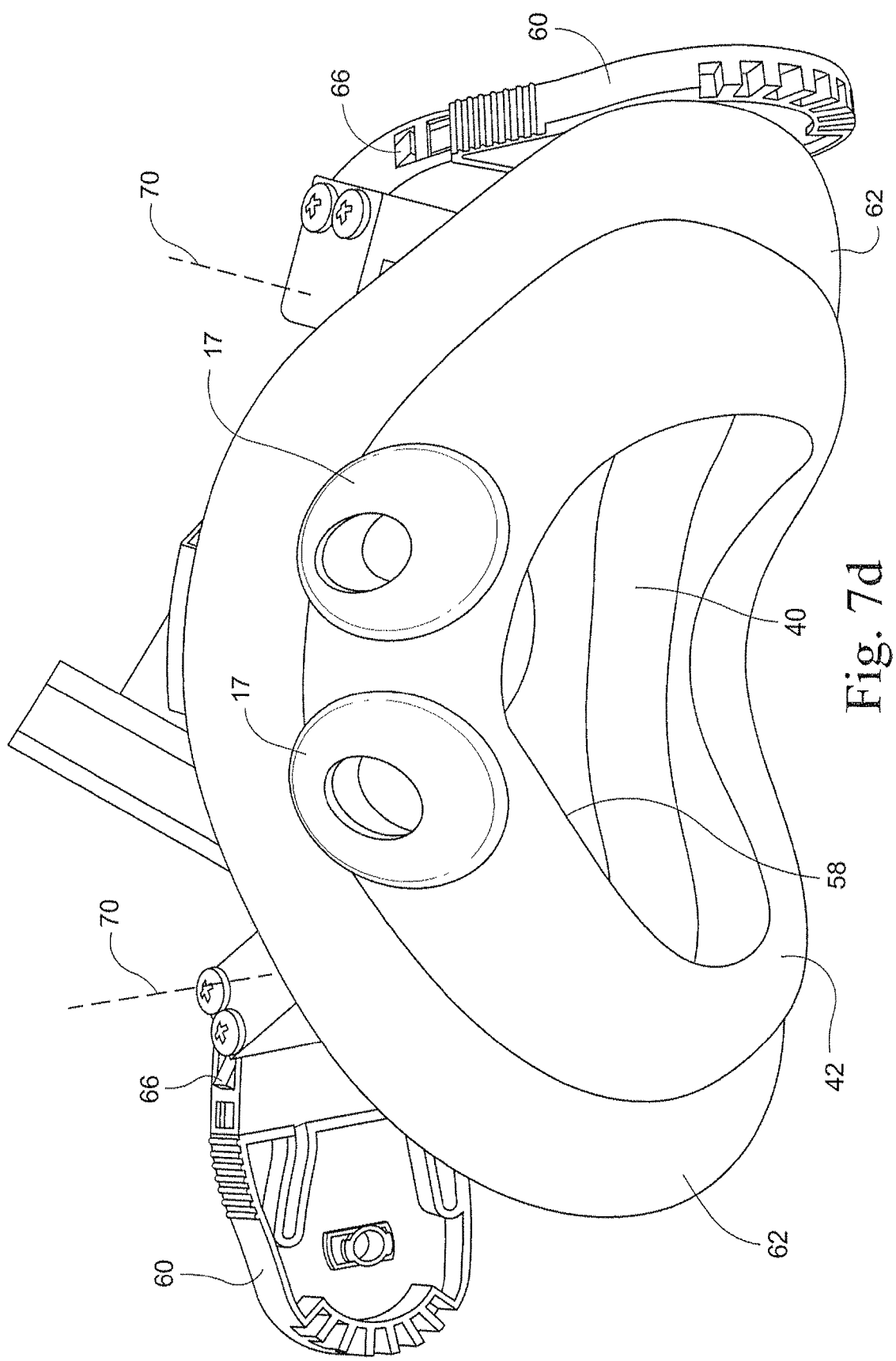

FIGS. 7c-7f show an alternative embodiment of a patient interface assembled to a headgear assembly 31 via clip 60 that is selectively adjustable in a rotational sense with respect to yoke 31 attached to strap 30, as described in U.S. patent application Ser. No. 10/391,440, filed Mar. 19, 2003, incorporated herein by reference in its entirety. Each clip 60 includes opposed arms 64 that may resiliently flex towards one another to allow engagement and disengagement of claws 66 formed on arms 64. The claws 66 may lockingly engage with corresponding structure or a receptacle 68 formed on or as part of frame 38. In this embodiment, the receptacle 68 may be moved, flexed or pivoted with respect to a portion 38a of the frame 38, e.g., along pivot axis 70. FIG. 7d shows the clips 60 in different angular positions.

Figure 7E:
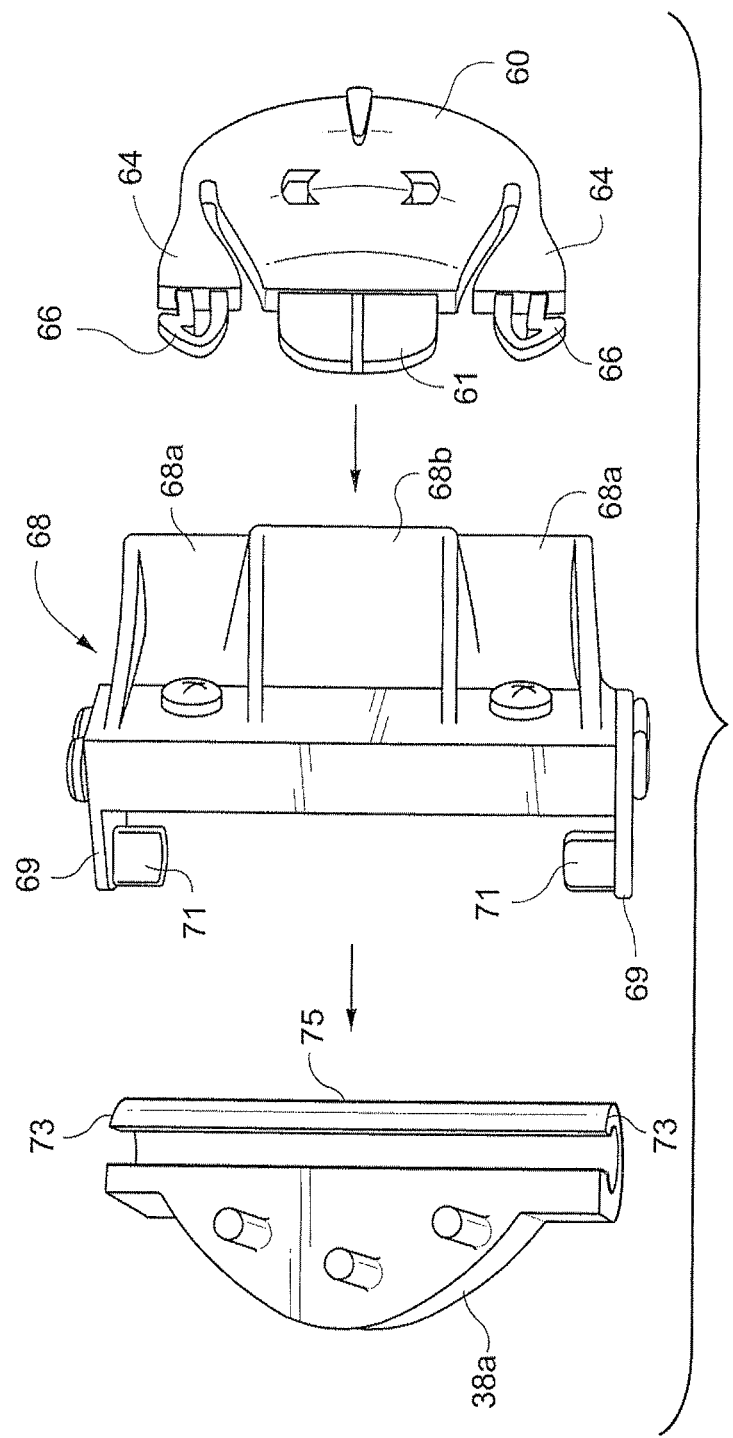

FIG. 7e is an exploded view of clip 60, receptacle 68 and portion 38a of frame 38. The portion 38a may be attached to (e.g., via glue) or formed as an integral part of the frame 38. The receptacle 68 includes side chambers 68a for receiving claws 66 and a central chamber 68b for receiving central tab 61 of clip 60. The receptacle 68 may be attached to portion 38a, e.g., via a pin and slot assembly. For example, the receptacle 68 may include opposed arms 69 each including a pin 71. Each pin 71 can be received within an end 73 of a C-shaped channel 75. At least one of the arms 69 or the C-shaped channel 75 may flex to allow assembly and disassembly. Of course, other arrangements for allowing relative movement are possible.

Figure 7F:
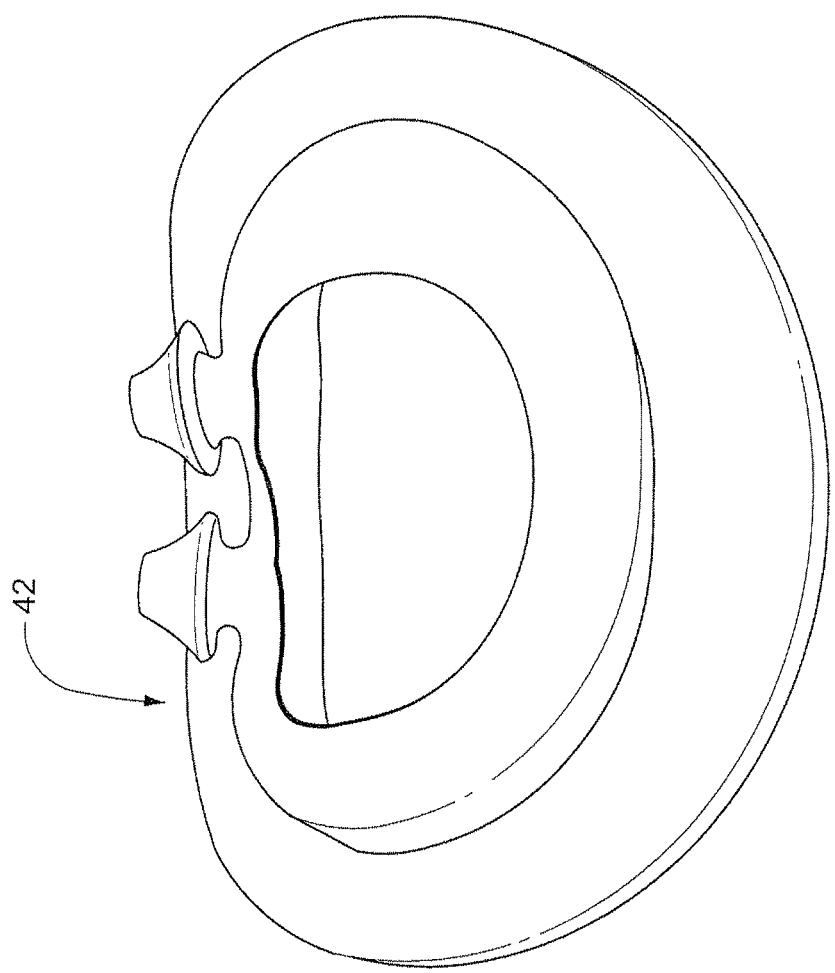

Alternative headgear may be used, i.e., this embodiment is not limited to the headgear assembly shown in FIG. 7c. Vents 72 for the removal of excess carbon dioxide are shown in FIG. 7c. The vents 72 may be formed on an elastic insert, as described in U.S. Pat. No. 6,561,190, incorporated herein by reference in its entirety. FIG. 7f shows an enlarged patient-side view of the cushion 42 in isolation.

Figure 8:
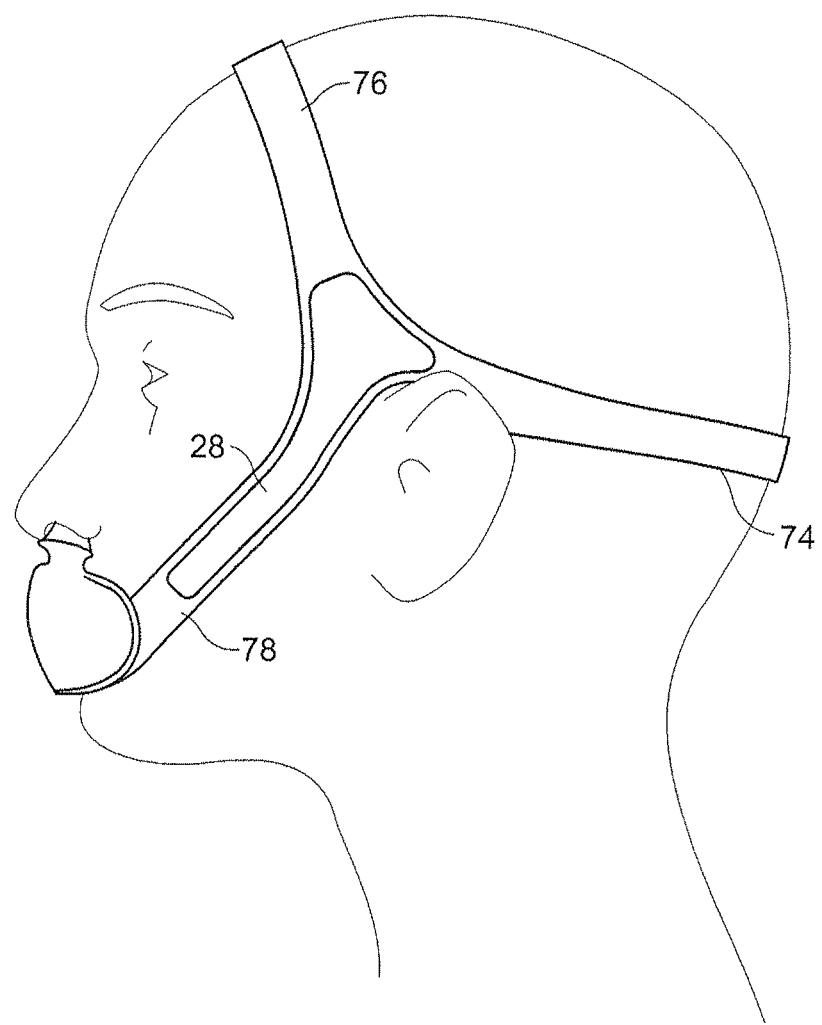
FIG. 8 shows a patient interface in accordance with an embodiment of the invention connected to a headgear routed around the top of the ears.

FIG. 8 shows an alternative form of headgear with an occipital strap 74, a coronal strap 76 and a depending strap 78 that is routed to the top of the ears. The headgear straps 74, 76, 78 may be rigid or may be constructed from a laminated foam material such as Breath-O-Prene™. In one form the headgear straps may be constructed from a combination of a soft comfortable material, such as Breath-O-Prene and a stiffening yoke 28 constructed from a polymer, such as nylon, as described in International Patent Application PCT/AU03/

00458. Angular adjustment between the rigid frame 38 and the headgear, such as that may be achieved via the arrangement shown in FIG. 7c.

Figure 9:
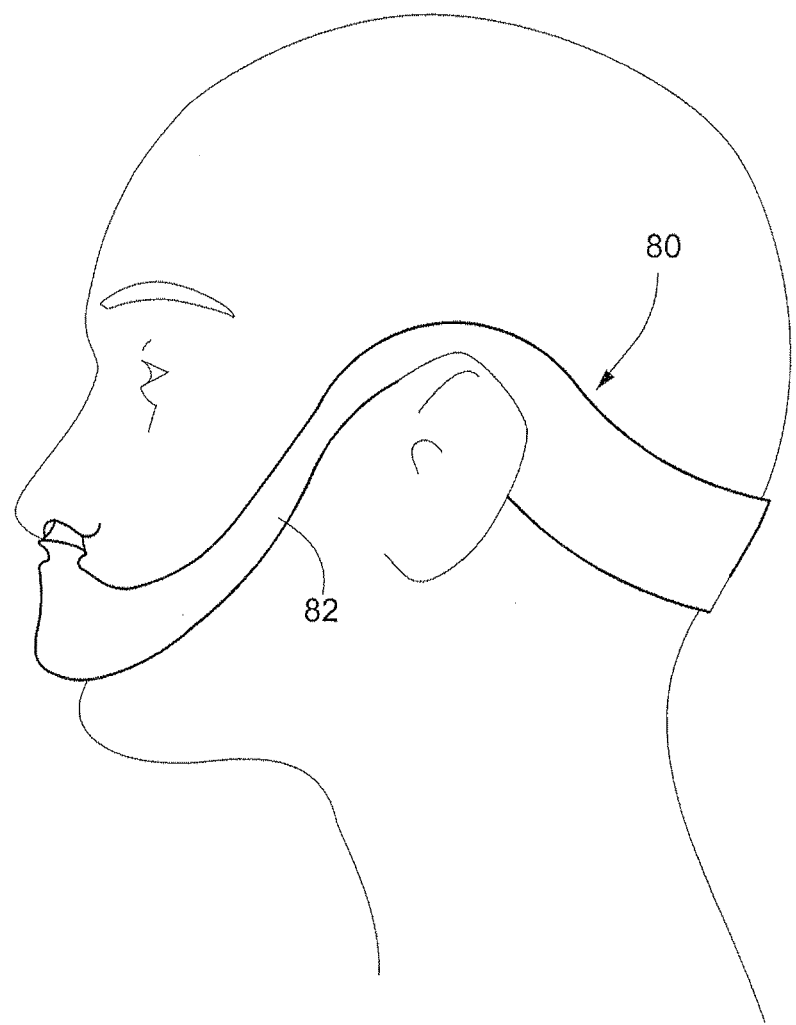
FIG. 9 shows a patient interface in accordance with an embodiment of the invention connected to different forms of headgear routed around the top of the ears.
Figure 10:
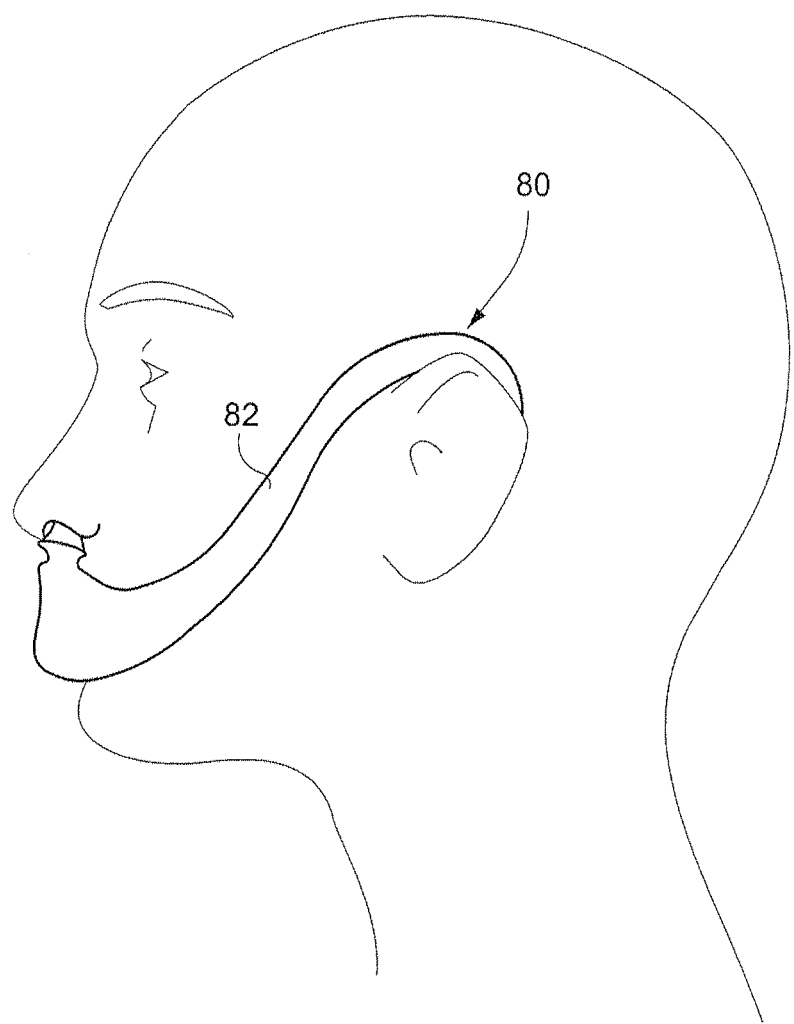
FIGS. 10-12 illustrate various headgear arrangements according to further embodiments of the invention.
Figure 11:
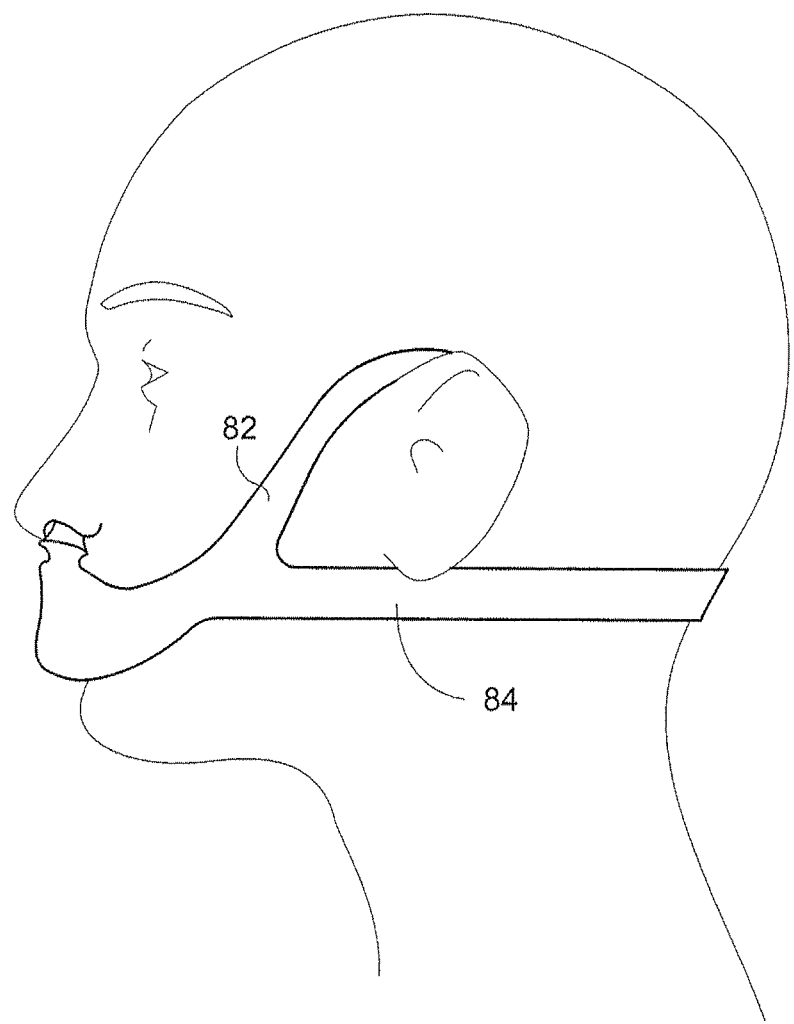
Figure 12:
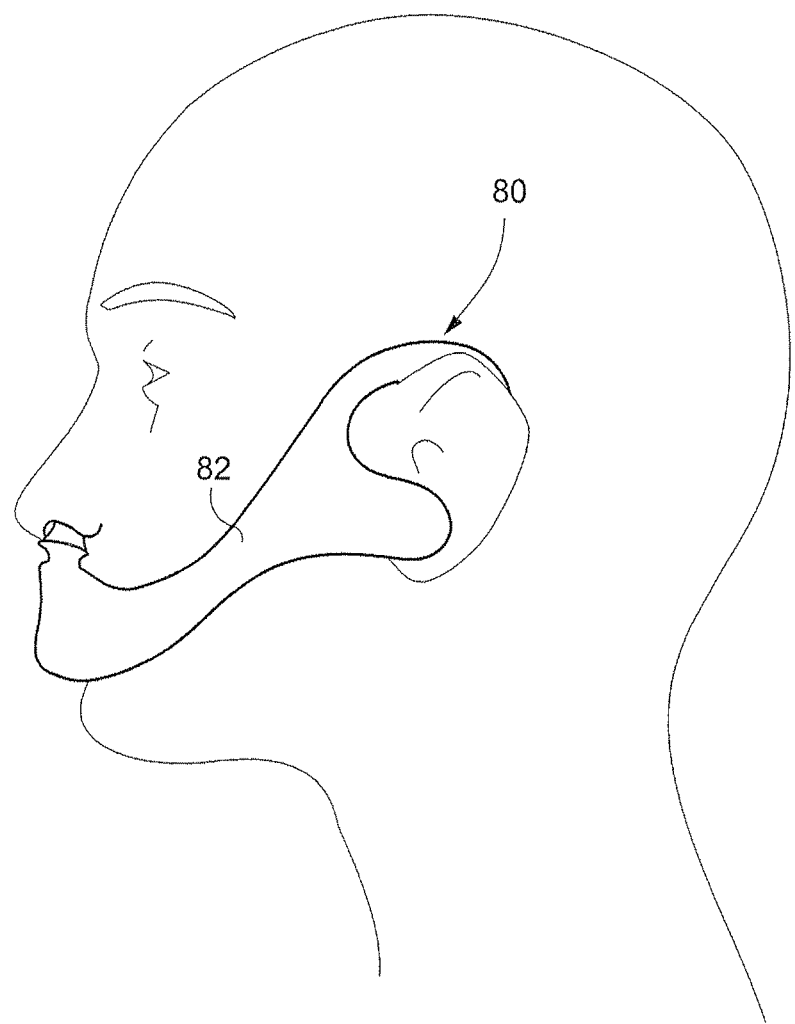
Figure 13:
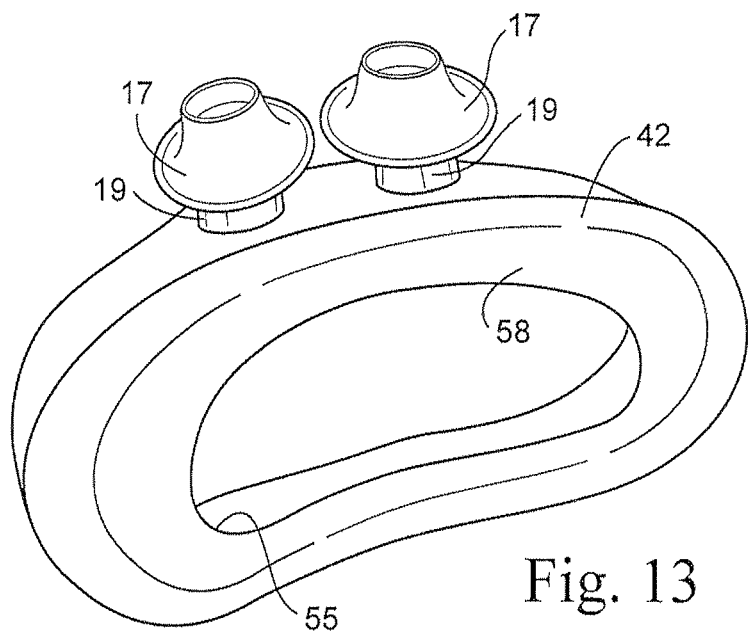

FIGS. 9-12 show the patient interface supported by spectacles-type headgear 80. One strap 82 is used as a hook mechanism behind the ear. The strap 82 may be extended to wrap around the head and apply a force inwards towards the head, as shown in FIG. 9, or the wrap around portion may be eliminated as shown in FIG. 10. FIG. 11 shows an additional stabilizing band 84 around the neck. The headgear straps may be formed of any suitable material such as textile, plastic or semi-rigid assemblies. The headgear assembly has the advantage that it covers the minimum head area and therefore is more comfortable than many traditional designs. In order to improve patient comfort, the headgear may also require adjustment to suit the head circumference and ear height. It may also be applied to alternative forms of patient interface such as nasal prongs or nose masks.

FIGS. 13-18d illustrate another embodiment of a patient interface. As illustrated, the patient interface includes a cushion 42 and a pair of nozzles 17 flexibly mounted to the cushion 42. The patient interface is formed as a one-piece structure such that the cushion 42 is integrally formed in one-piece along with the nozzles 17. For example, the cushion 42 and nozzles 17 may be formed in an injection molding process as is known in the art. Also, the cushion 42 and nozzles 17 form one chamber with flexibility between the cushion 42 and nozzles 17 to provide for movement and changes in alignment between the two.

The cushion 42 includes a non-face-contacting portion and a face-contacting portion. The non-face-contacting portion is structured to be removably and replacably attached to a rigid frame associated with the air delivery tube. The non-face-contacting portion may be removably and replacably attached to the frame in any suitable manner, e.g., cushion clip, friction or interference fit, and/or tongue-and-groove arrangement, as is known in the art. However, the non-face-contacting portion may be permanently attached to the frame, e.g., by glue and/or mechanical fastening means.

As best shown in FIGS. 15 and 18a-18d, the face-contacting portion of the cushion 42 includes a side wall 51, a pair of underlying support rims 53 extending away from the side wall 51, and a membrane 58 provided to substantially surround the rims 53 and provide a sealing structure for the face contacting portion. The side wall 51 and rims 53 provide a support structure for the face contacting portion. Also, as best shown in FIG. 16, the face-contacting portion is contoured to follow generally the curvature of the patient's face.

The membrane 58 is structured to form a seal around the lips of a patient. In the illustrated embodiment, the membrane 58 has a substantially flat profile. In use, the edge 61 of the flat-profiled membrane 58 is the first point of contact with the patient's face. As the membrane 58 comes more into contact with the patient's face, the membrane 58 conforms to the patient's face with good contact at the inner edge 61 thereof, which reduces the possibility of pressurized air coming between the skin and the edge 61, thereby improving the integrity of the seal. Also, the edge 61 of the membrane 58 contacts the face and fully extends or stretches the membrane 58, thereby eliminating any wrinkles. A more rounded membrane profile provides a tangential contact with the patient, potentially providing a leak path under the membrane when air pressure is applied. Further, the membrane 58 extends further than the edges of the rims 53 to prevent the rims 53 from being a source of irritation (e.g., see FIG. 18b).

Figure 14:
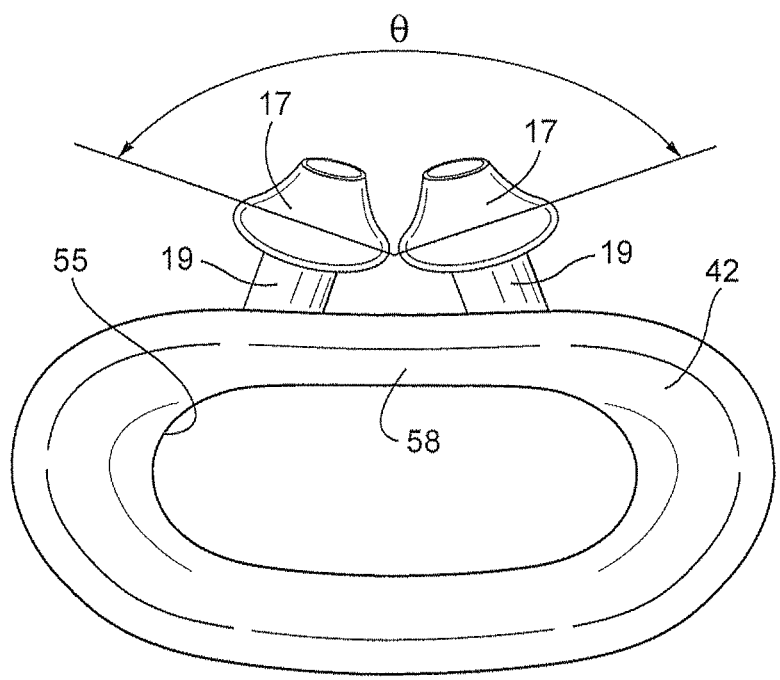

The inner edge of the membrane 58 defines an aperture 55 that receives the patient's lips. As best shown in FIG. 14, the aperture 55 has a generally oval shape. However, the aperture 55 may have any other suitable shape to accommodate variations in the shape of a patient's mouth.

Figure 20:
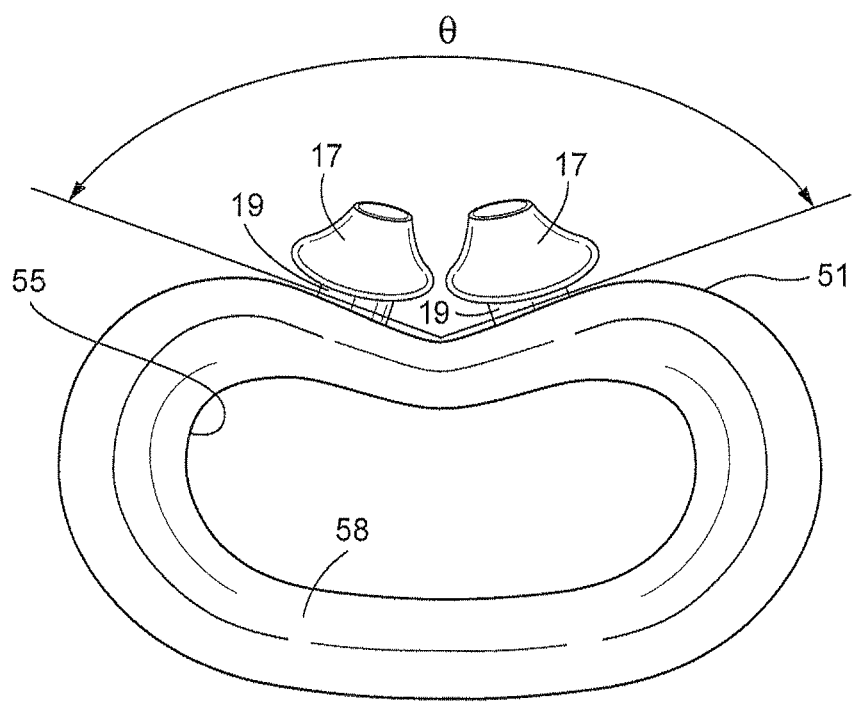
Figure 21:
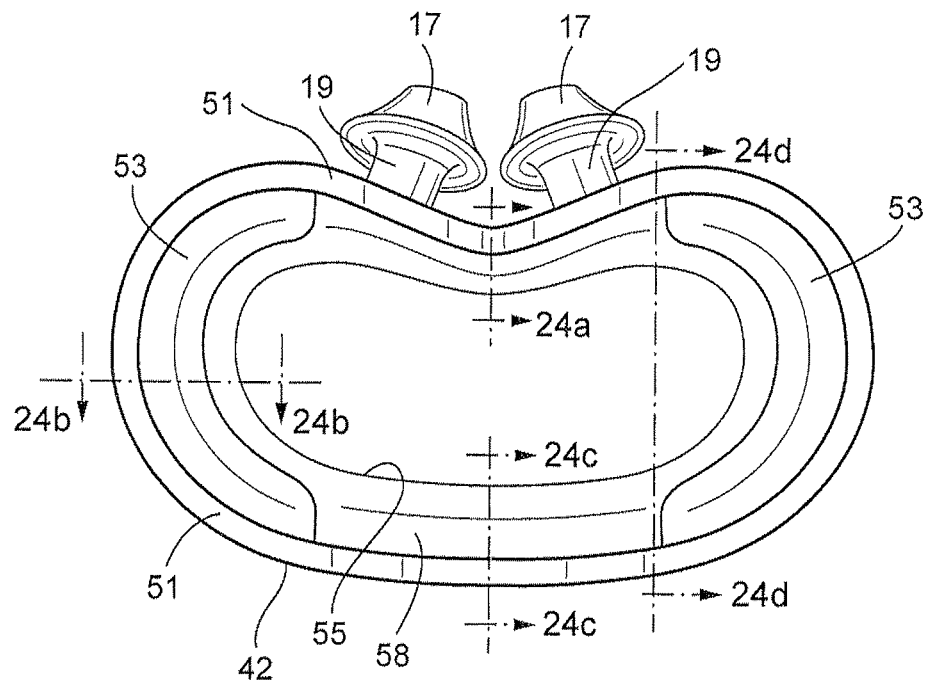

For example, FIGS. 19-24d illustrate another embodiment of a patient interface. Similar elements are indicated with similar reference numerals. As illustrated, the upper edge of the aperture 55 has an arcuate protruding portion. Also, as shown in FIGS. 20 and 21, the upper side of the side wall has an arcuate configuration that corresponds with the arcuate configuration of the upper edge of the aperture 55. Thus, the plan profile of the cushion 42 shown in FIGS. 20 and 21 is curved and has a shape similar to a smile. This configuration helps stability by more closely following the patient's facial geometry and prevents roll since the cushion 42 is higher at the sides. That is, the cushion shown in FIG. 20 has a greater height than the cushion shown in FIG. 14, which helps with stability. However, the shorter height of the cushion shown in FIG. 14 has a shorter profile and is therefore less obtrusive to the patient. For example, the cushion in FIG. 20 may have a height of about 60 mm and the cushion in FIG. 14 may have a height of about 50 mm. However, the cushion may have any other suitable height. The cushion 42 also has a membrane 58 with a substantially flat profile (e.g., see FIGS. 24a-24c), which provides an enhanced seal as described above.

Figure 15:
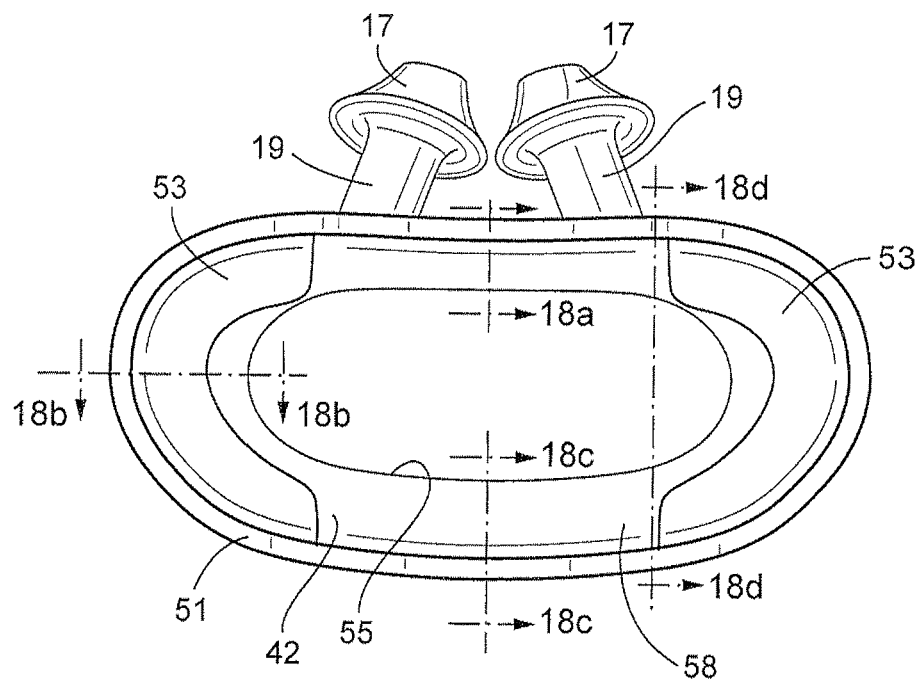
Figure 16:
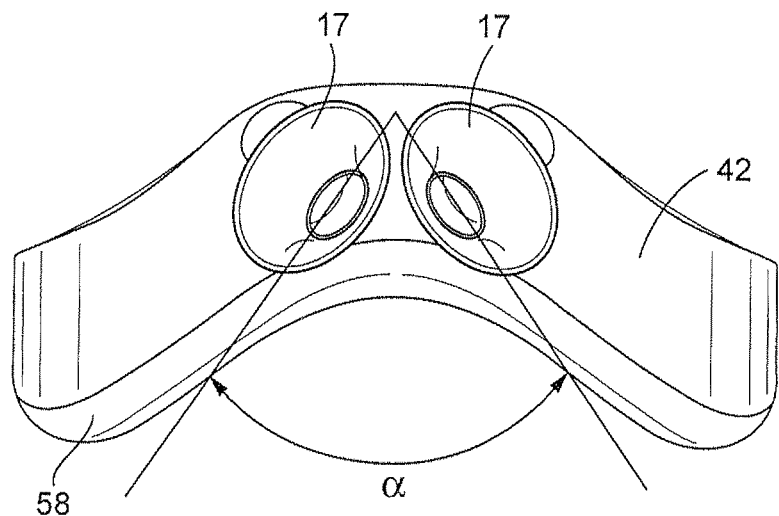
Figure 19:
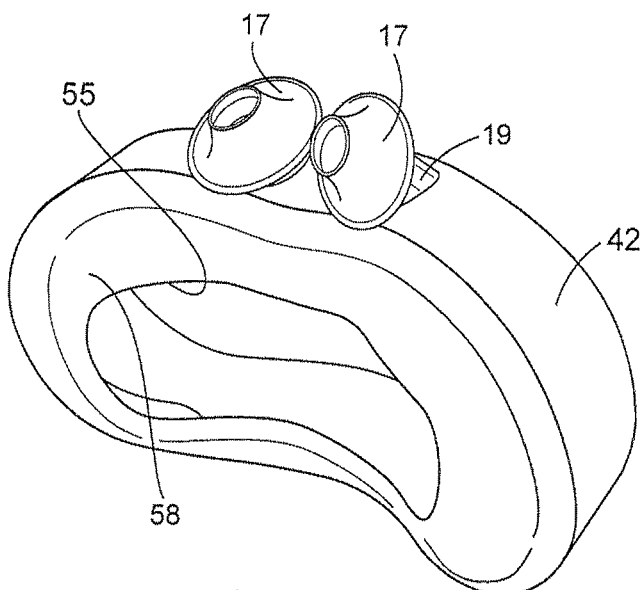
FIGS. 19-24d illustrate another embodiment of a single chamber patient interface.
Figure 24A:
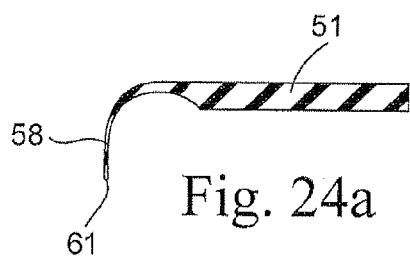
Figure 24B:
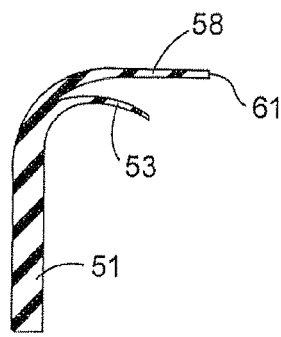
Figure 24D:
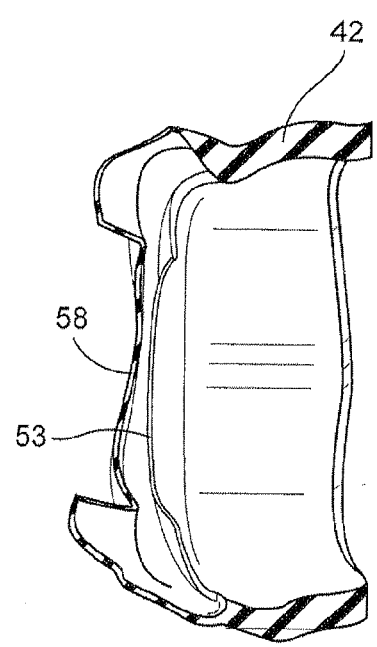
Figure 24C:
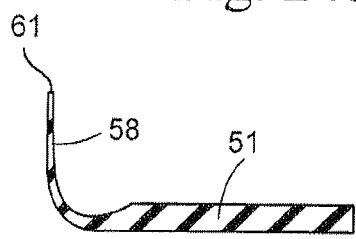

As best shown in FIG. 15, the rims 53 are preferably provided on lateral sides of the side wall only 51. The rims 53 add rigidity to the membrane 58 at the sides of the patient's mouth or cheeks. As illustrated, each rim 53 has a general C-shape and extends inwardly into the cavity of the cushion 42. While it is preferable that the membrane 58 be thinner than the rim 53, they could have the same thickness. For example, in FIGS. 18a, 18c, 24a, and 24c, the side wall thickness may be about 3.20 mm, which tapers to about 0.50 mm at the edges of the membrane. In FIGS. 18b and 24b, the side wall thickness may be about 3.20 mm, which tapers to about 0.50 mm at the edges of both the rim and the membrane. However, the side wall, rim, and membrane may have any other suitable thicknesses.

As shown in FIGS. 18b and 18d, the inside surface of the membrane 58 is spaced from the outside surfaces of the rims 53 so that the membrane 58 can accommodate small variations in the shape of the patient's mouth without undue force and can account for small movement of the patient interface relative to the patient during use, while maintaining an effective seal. The spacing between the rim 53 and the membrane 58 may have any suitable size. Moreover, the rim 53 may extend around the entire perimeter of the side wall, or may have any other suitable configuration to support the membrane 58.

Figure 25A:
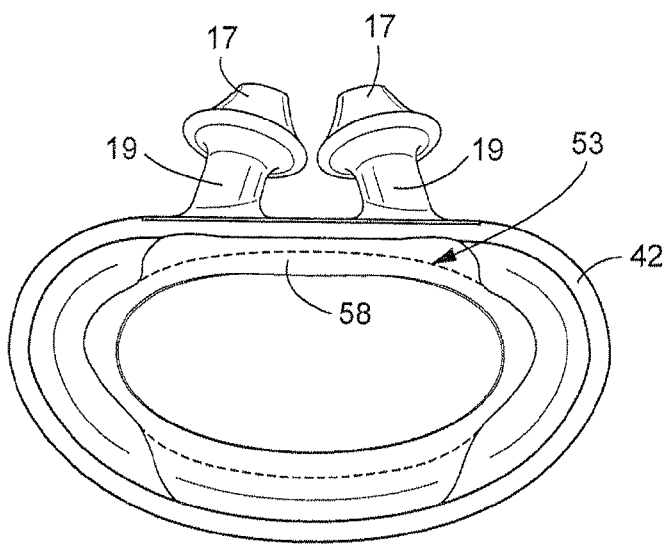
FIGS. 25a-25e illustrate other embodiments of a single chamber patient interface.
Figure 25B:
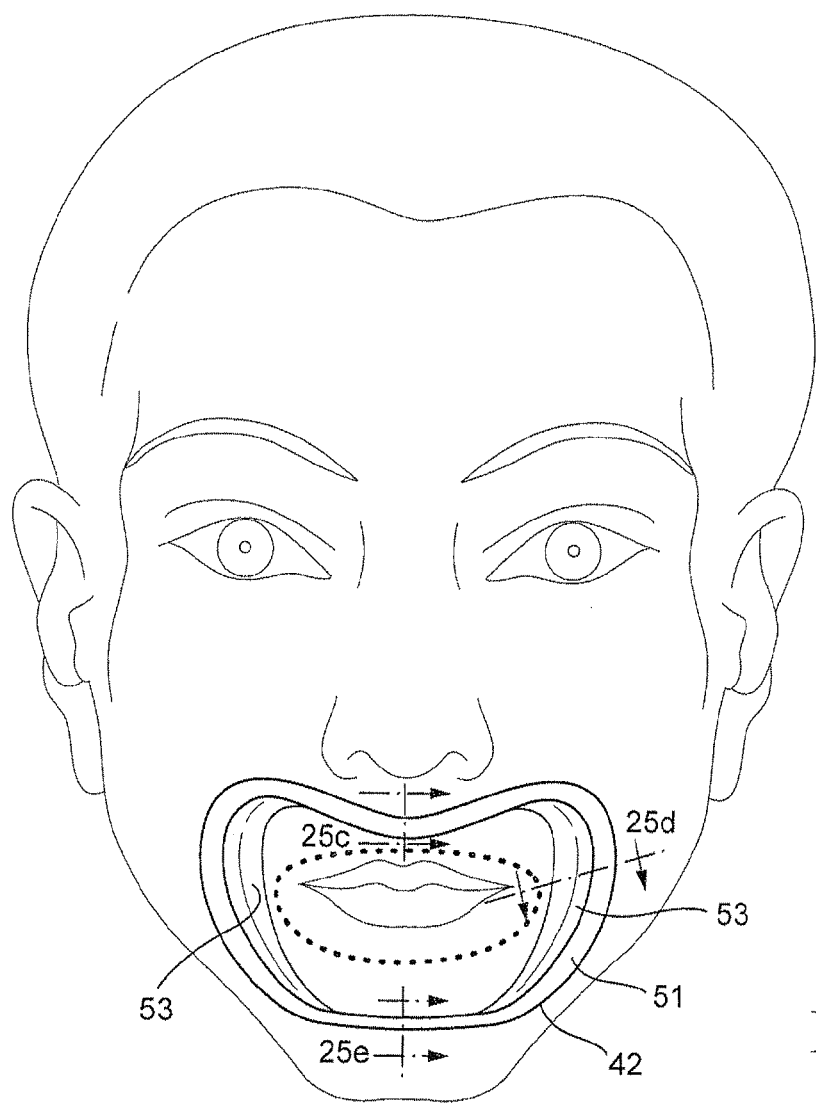
Figure 25C:
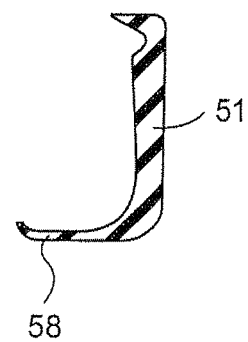
Figure 25D:
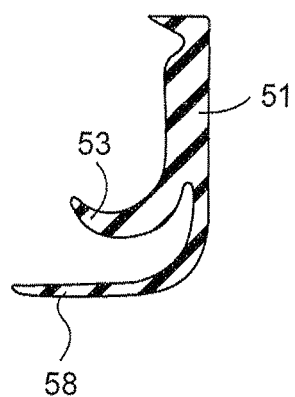
Figure 25E:
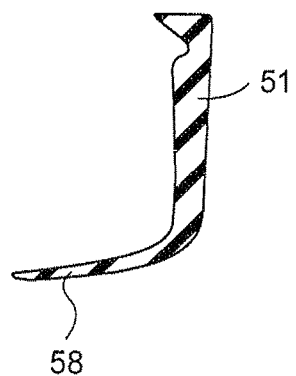

In the illustrated embodiment, the face-contacting portion of the cushion 42 has a double-walled construction, i.e., membrane and rim, in the region of the cheeks and a single-walled construction, i.e., membrane, under the nozzles 17 and in the region of the chin and/or lower lip. The single wall construction at the top and bottom of the cushion 42 helps to accommodate high landmarks, e.g., pointed chin, by allowing the center of the cushion 42 to flex. This flexibility accommodates more patients with the same cushion 42. Also, the single wall construction under the nozzles 17 alleviates space constraints and potential occlusion of the nasal air path by a rim. However, the cushion 42 may have any other suitable construction, e.g., single walled, triple walled or more walled construction, in any suitable region of the cushion 42, e.g., cheek, chin, under nozzles. For example, FIG. 25a illustrates an embodiment of a patient interface substantially similar to the patient interface shown in FIGS. 13-18d. In contrast, the patient interface includes a rim 53 that extends around the entire perimeter of the cushion 42 as indicated by the dashed line. Also, the rim 53 could be completely removed. FIGS. 25b-25e illustrates an embodiment of a patient interface substantially similar to the patient interface shown in FIGS. 13-18d (nozzles omitted for clarity purposes). In contrast, the side wall 51 of the cushion 42 has a slightly different perimeter geometry. The cushion 42 also has a membrane 58 with a substantially flat profile (e.g., see FIGS. 25c-25e), which provides an enhanced seal as described above.

The side wall of the cushion 42 supports the pair of nozzles 17. Similar to the above embodiments, the nozzles 17 may have a similar form to those disclosed in U.S. Pat. No. 7,318,437, the contents of which are hereby incorporated by cross-reference, however they may take the form of any nasal prongs insertable into each nare.

Figure 22:
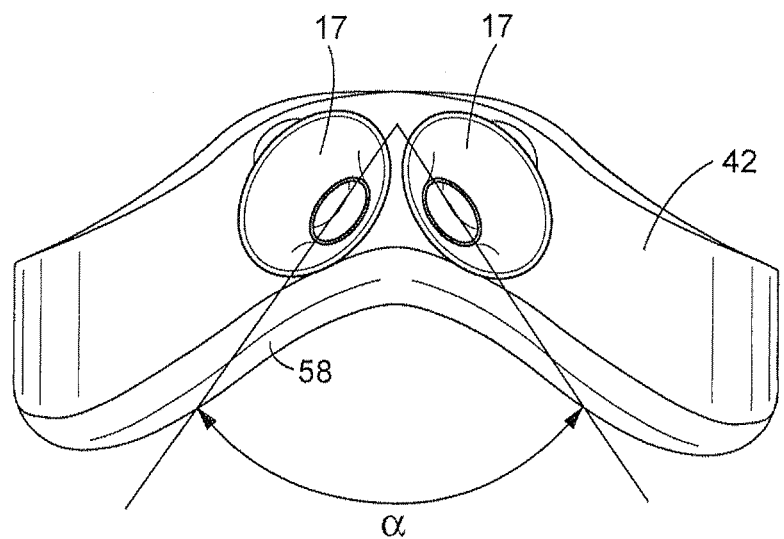
Figure 23:
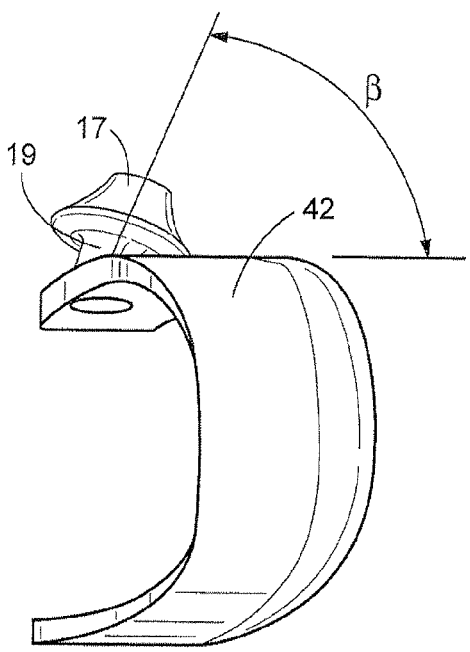

As illustrated, each nozzle 17 includes a conduit 19 that interconnects each nozzle 17 with the cushion 42 and allows breathable gas to pass from the chamber defined by the cushion 42 to the nozzles 17. As shown in FIGS. 14, 16 and 17, the conduits 19 and nozzles 17 attached thereto are angled with respect to the side wall to properly position the nozzles 17 with the nasal passages of the patient. For example, the angle $\theta$ in FIGS. 14 and 20 is referred to as the alar angle, the angle $\alpha$ in FIGS. 16 and 22 is referred to as the nostril angle, and the angle $\beta$ in FIGS. 17 and 23 is referred to as the naso-labial angle. As illustrated, the angle $\theta$ is substantially the same in FIGS. 14 and 20, the difference being that the angle $\theta$ in FIG. 14 is defined by the nozzles 17 whereas the angle $\theta$ in FIG. 20 is defined by the side wall 51. The angles $\theta$, $\alpha$, and $\beta$ may have any suitable value and may be determined from anthropometric data. For example, the angle $\theta$ may be between 60°-180°, the angle $\alpha$ may be between 0°-120°, and the angle $\beta$ may be between 40°-140°. These angles are merely exemplary and should not be limiting. Also, the nozzles 17, conduits 19, and side wall 51 may have any suitable configuration to properly position the nozzles 17 with respect to the nasal passages of the patient.

Also, the conduits 19 may have different lengths to accommodate different patients. For example, the conduits 19 illustrated in FIGS. 13-17 are longer than the conduits 19 illustrated in FIGS. 19-23. The longer conduits of FIGS. 13-17 provide more nozzle flexibility, whereas the shorter conduits of FIGS. 19-23 allow more direct transfer of forces from the side wall support to the nozzles. The conduits 19 may have any suitable length and may be suitably varied to accommodate various patients, e.g., with varying length between the patient's nose and upper lip. For example, in an embodiment, the nozzles 17 are about 8 mm long, which allows good flexibility and articulation while still allowing the nozzles 17 to be loaded adequately to effect seal.

Figure 26:
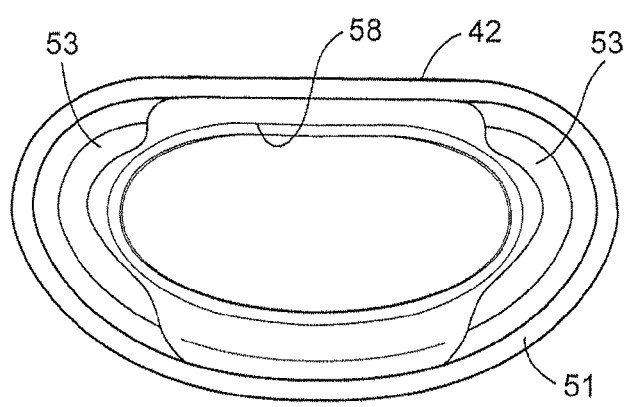
FIGS. 26-28 illustrate another embodiment of a single chamber patient interface with no nozzles.
Figure 27:
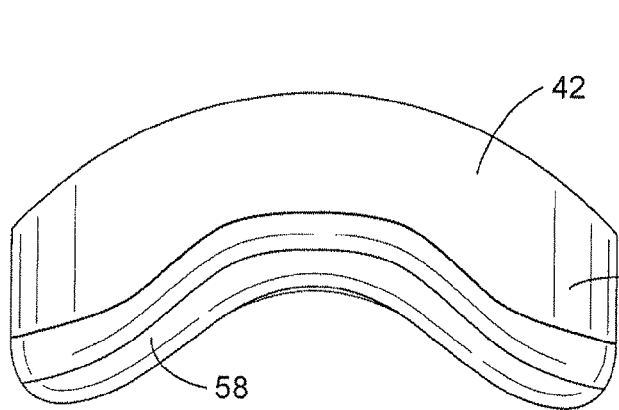
Figure 28:
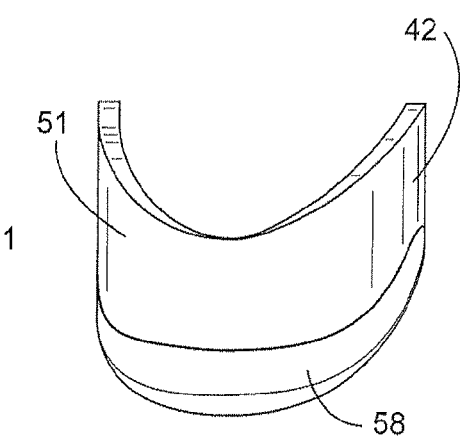

FIGS. 26-28 illustrate an embodiment of a patient interface wherein the nozzles have been removed so that the patient interface includes a cushion 42 only. The cushion 42 may have a structure similar to the cushions described above, e.g., side wall 51, a pair of rims 53 extending away from the side wall 51 in the cheek regions, and a membrane 58. However, the cushion 42 may have any other suitable structure to seal around a patient's mouth.

Figure 29:
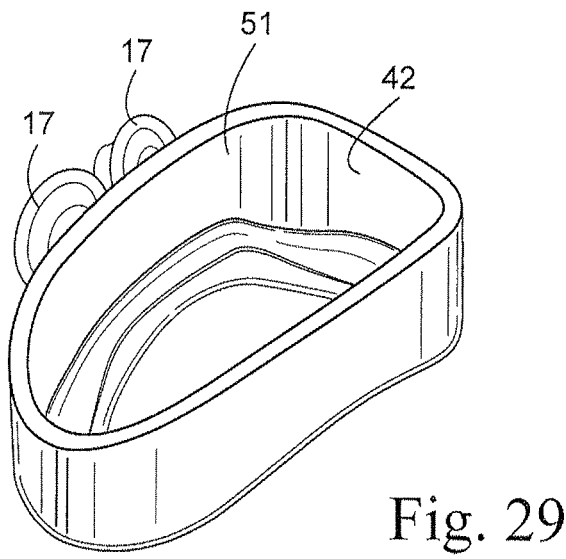
FIGS. 29 and 30 illustrate embodiments of a single chamber patient interface with blocked nozzles.
Figure 30:
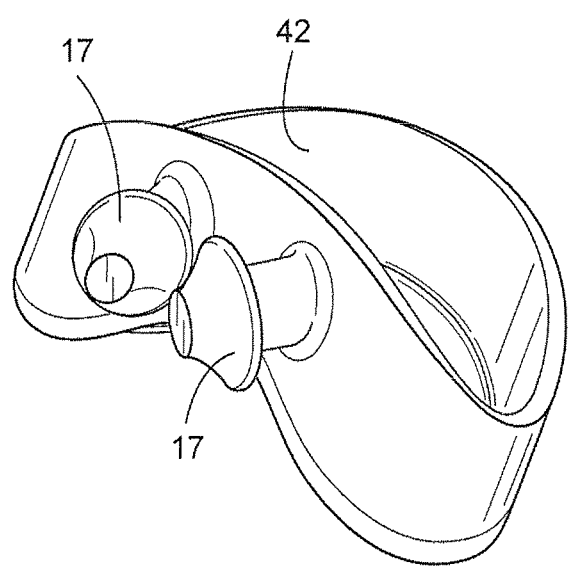

FIGS. 29 and 30 illustrate embodiments of a patient interface that include a cushion 42 and a pair of nozzles 17 that are blocked from fluid communication with the chamber defined by the cushion 42. In FIG. 29, the nozzles 17 are blocked at entrance to the cushion 42. That is, the upper portion of the side wall 51 is not provided with any openings that communicate with the nozzles 17. In FIG. 30, the nozzles 17 are blocked at the nozzle tips. That is, the nasal opening of the nozzle 17 is blocked so that gas cannot pass through the nozzles 17. The pressure within the nozzles 17 aids the seal within the nasal passages of the patient. In another embodiment, a set of plugs may be inserted into the nozzles 17, e.g., at the top or bottom of the nozzles, to block nasal flow. In these embodiments, the nozzles 17 simply seal the patient's nasal passages, and gas is delivered to the patient's mouth only. The blocked nozzles may also serve to stabilize the cushion and help with alignment.

FIGS. 31-33c illustrate an embodiment of a patient interface that includes a cushion 42 and a pair of nozzles flexibly mounted to the cushion 42 (nozzles omitted for clarity purposes). As illustrated, the cushion 42 includes a side wall 51 incorporating a gusset portion 62, a pair of rims 53 extending away from the side wall 51, and a membrane 58 to substantially surround the rims 53 and provide a sealing structure for engagement with the patient's face.

Figure 33A:
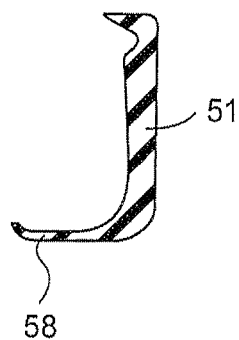
Figure 33B:
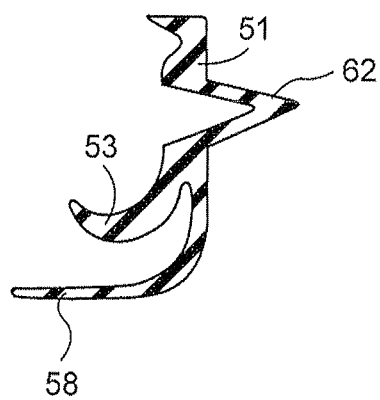

Similar to the embodiments in FIGS. 13-24d, the rims 53 are provided on the lateral sides of the side wall 51 only (e.g., see FIGS. 31 and 33b). However, a rim may be provided around the entire perimeter of the side wall, or at any other suitable portion of the side wall, e.g., chin portion of the cushion. Also, similar to the embodiments in FIGS. 13-24d, the side wall thickness may be about 3.20 mm, which tapers to about 0.50 mm at the edges of both the rim and the membrane. The thickened side wall helps to support the nozzles in proper position.

Figure 33C:
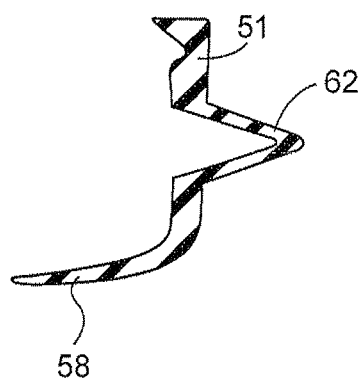

As best shown in FIGS. 32, 33b, and 33c, the gusset portion 62 is provided on the lateral sides of the side wall 51 and the lower wall of the side wall 51 (adjacent the patient's chin). However, the gusset portion 62 may be provided around the entire perimeter of the side wall. Similar to the gusset portion described above in FIGS. 6a and 6b, for example, the gusset portion 62 provides further flexibility within the patient interface to allow the interface to adjust to the geometry of different patients, allow for any jaw or head movement during sleep, and allow the membrane 58 of the cushion 42 increased freedom to deform in accordance with the contours of the mouth region without disturbing nozzle seal. Also, the gusset portion 62 could be replaced by a flexible spring, or any other suitable structure that would add flexibility.

FIGS. 34-38 illustrate embodiments of a patient interface that include a cushion 42 and a pair of nozzles 17 that are selectively mounted to the cushion 42. Specifically, the nozzles 17 are formed separately from the cushion 42, and then secured to the cushion 42 to construct a patient interface with both cushion 42 and nozzles 17. This arrangement provides a greater scope of patient fitting by being able to select cushion size and nozzle size independently. Also, the nozzles 17 may be independently aligned with respect to the cushion 42 for optimal fit.

In each of the embodiments, each nozzle 17 includes a nozzle portion 21 that seals within a respective patient nasal passage and a base portion 23 that is mountable to the cushion 42. The side wall of the cushion 42 includes nozzle mounting portions 25 structured to mount a respective nozzle 17.

The nozzles 17 may be mounted to the cushion 42 in any suitable manner. For example, FIG. 34 illustrates an arrangement wherein the nozzle mounting portions 25 are in the form of inclined platforms 104 structured to support a respective nozzle 17 thereon. The base portion 23 of the nozzles 17 may be secured to respective platforms 104 in any suitable manner, e.g., adhesive, male/female connection, etc.

FIG. 35 illustrates an arrangement wherein the nozzle mounting portions 25 provide substantially flat mounting surfaces structured to support a respective nozzle 17 thereon. The base portion 23 of the nozzles 17 are secured to respective surfaces via a male/female connection mechanism. For example, each base portion 23 may include a protrusion that is secured within a respective opening provided in the respective nozzle mounting portion 25 of the cushion 42. However, the nozzles 17 may be secured to the cushion 42 in any other suitable manner.

FIG. 36 illustrates an arrangement wherein the nozzle mounting portions 25 are in the form of cylindrical protrusions structured to engage within openings provided in the base portion 23 of respective nozzles 17. However, the nozzles 17 may be secured to the cushion 42 in any other suitable manner.

Figure 38:
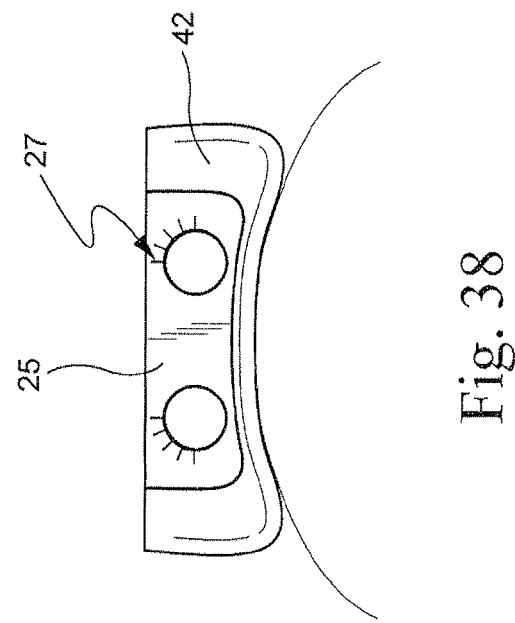

As shown in FIGS. 35 and 36, the nozzles 17 are mounted to the cushion 42 such that the nozzles 17 can rotate independently to align each nozzle 17 with a respective one of the patient's nares. As shown in FIG. 36b, a ball-jointed insert 106 may be incorporated into the nozzles 17 to allow greater rotational and angular freedom and allow alignment in all directions. As shown in FIG. 38, the cushion 42 may include angular alignment marks 27 to align the nozzles 17 with respect to the cushion 42, which assists the patient in consistent set-up. The marks 27 may have any suitable configuration, e.g., detented.

Figure 37:
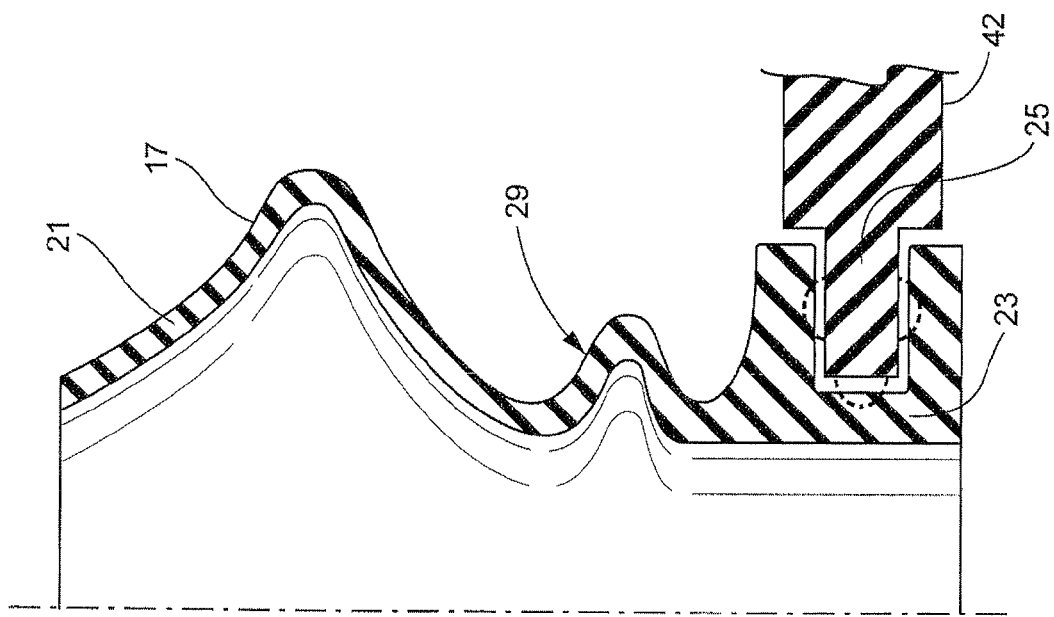

FIG. 37 illustrates an arrangement wherein each nozzle mounting portion 25 provides an opening defined by edges having a stepped configuration. The base portion 23 of each nozzle 17 has an annular recess that receives the stepped edge of the opening therein, so as to secure each nozzle 17 within the respective opening. The stepped edge may include one or more resilient protrusions (in dashed lines) to improve the seal between the cushion 42 and nozzles 17. Also, the stepped edge may have multiple steps to allow for selective height adjustment. However, the nozzles 17 may be secured to the cushion 42 in any other suitable manner. Also, the nozzle 17 illustrated in FIG. 37 includes a gusset portion 29 that adds flexibility and articulation of the nozzle 17 with respect to the cushion 42. It should be understood that one or more gusset portions 29 may be provided on each nozzle 17, and the gusset portion 29 may have any suitable configuration to improve nozzle flexibility.

The embodiments of FIGS. 34-37 allow nozzles 17 to be interchanged for different size patient nares, which improves seal and patient comfort. Also, it should be understood that the nozzles 17 could be interchanged individually, or a single insert could be provided that contains both nozzles 17.

Figure 40:
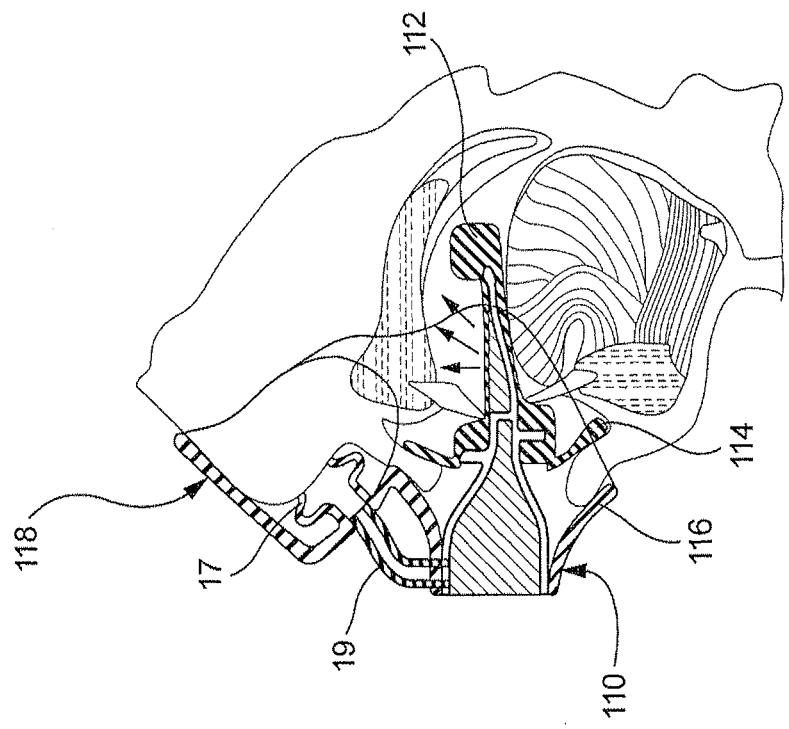
FIGS. 39-40 illustrate embodiments of a patient interface with a mouth appliance.
Figure 39:
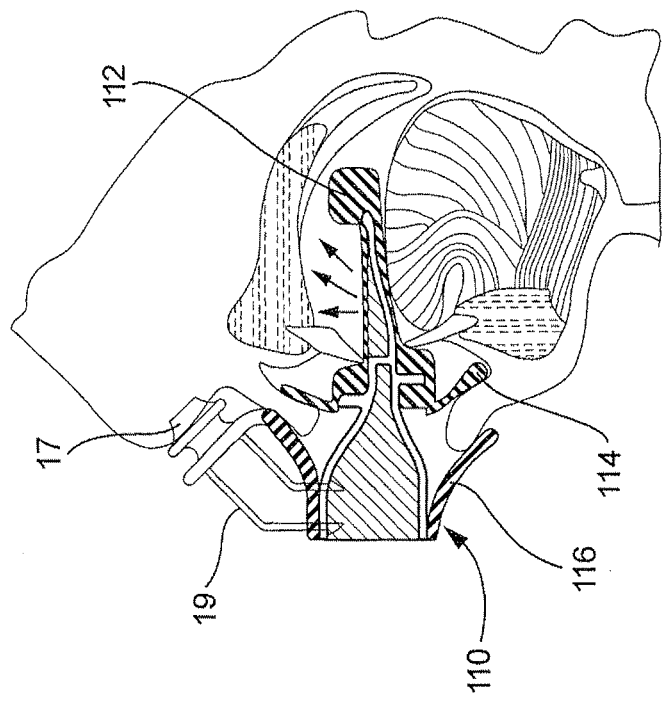

FIGS. 39-40 illustrate embodiments of a patient interface that include a pair of nozzles 17 that are mounted to a mouth appliance 110, e.g., an appliance that sits within a patient's mouth. In the illustrated embodiment, the mouth appliance 110 provides a mouth seal by sandwiching the inside and outside of the patient's mouth. Specifically, the mouth appliance 110 includes a tongue depressor 112, a soft seal 114 that abuts against the inner surface of the patient's mouth, and a snap flap 116 that abuts against the outer surface of the patient's mouth to provide an endstop against the appliance being swallowed. An example of such mouth appliance is disclosed in WO200195965, the contents of which are hereby incorporated by cross-reference. The nozzles 17 are mounted to the mouth appliance 110 by a conduit 19 that allows gas to pass between the mouth appliance 110 and nozzles 17. The conduit 19 may have a flexible or rigid construction. As shown in the embodiment of FIG. 40, a mask system 118, e.g., similar to a diving mask, may be incorporated into the patient interface to improve seal and to help locate the nozzles 17 with respect to the patient's nasal passages. Also, the tongue depressor 112 is optional and may be removed.

Figure 42:
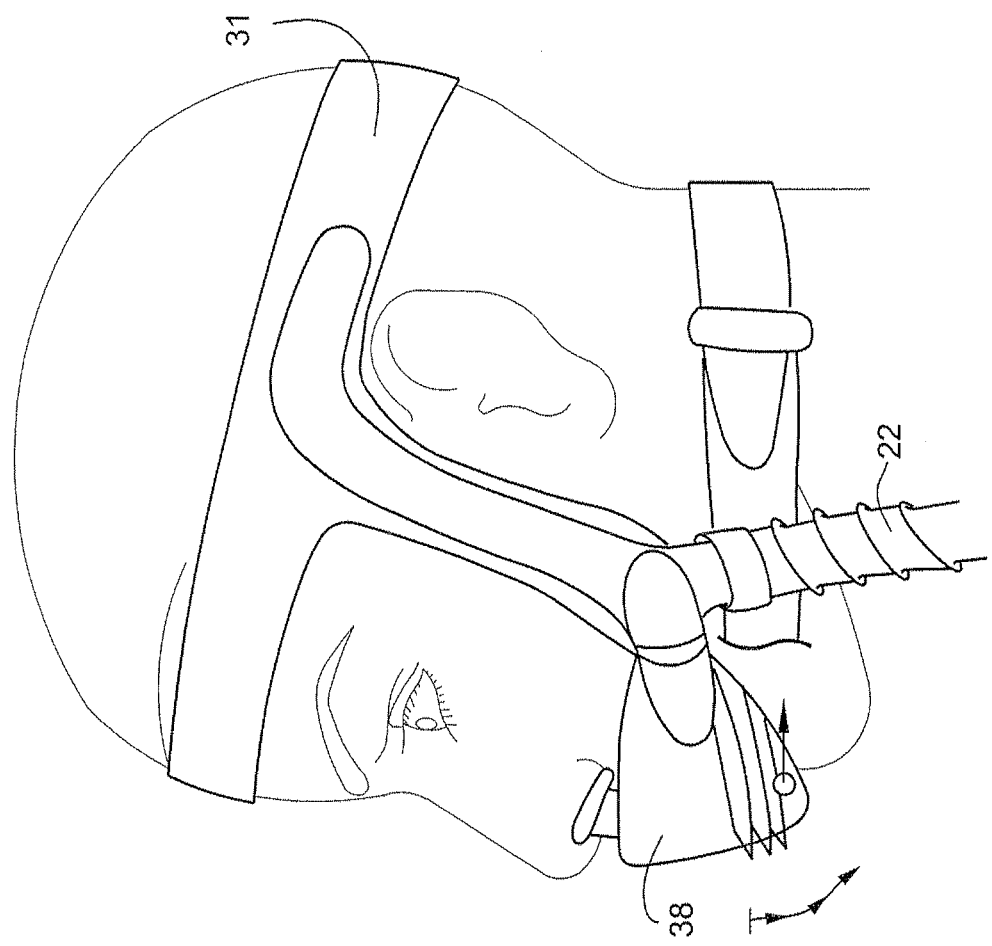
FIGS. 41-42 illustrate an embodiment of a patient interface with a corrugated frame.
Figure 41:
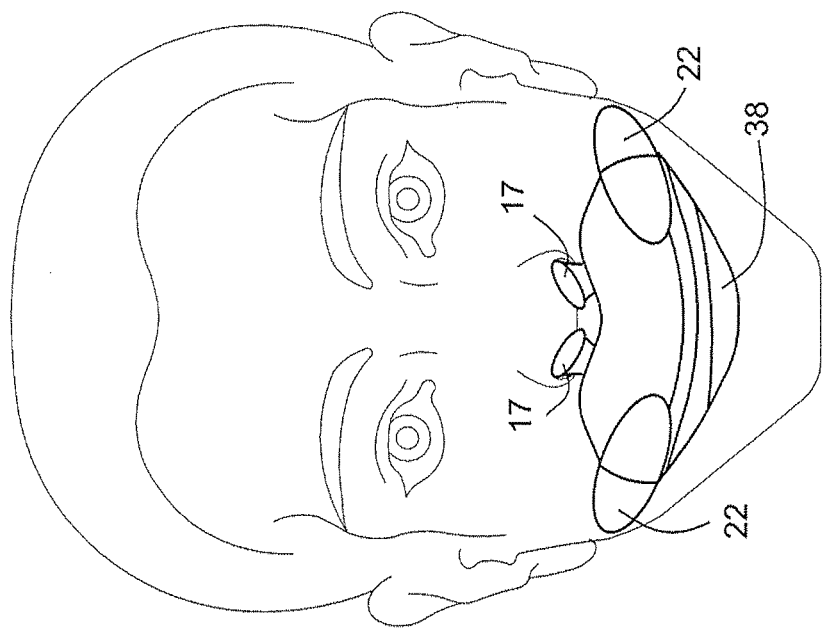

FIGS. 41 and 42 illustrate an embodiment of a patient interface having a corrugated frame 38 and a cushion (not visible) with nozzles 17 mounted to the frame 38, or to the cushion. The corrugations in the frame 38 add flexibility to the frame 38 to allow the frame 38 to adjust to the facial geometry of different patients and to allow for any jaw or head movement during sleep. For example, the frame 38 may move downwardly for jaw dropping during sleep, and may move rearwardly for receding jaw (see arrows in FIG. 42). As illustrated, the corrugations are provided along a lower portion of the frame 38. However, the corrugations may extend across the entire frame 38. The movement may be accomplished via pivoting and/or sliding action of the corrugated frame about the sides of the frame. In this arrangement, the seal in the lower lip region is thus not compromised even if the jaw moves. Also, frame flexibility may be provided by other suitable structures, e.g., gusset portion provided in the frame. The frame 38 may be adjusted, e.g., by adjusting the tension in the lower straps of a headgear assembly 31. Further, the corrugated configuration may be incorporated into a full-face mask.

Also, the frame 38 is structured such that inlet conduits 22 are coupled to the sides of the frame 38 for delivering breathable gas into the patient interface. However, one or more inlet conduits 22 may be coupled to the frame 38 in any other suitable manner, e.g., to the front of the frame.

FIGS. 43-46 illustrate embodiments of patient interfaces including a cushion 42 and a pair of nozzles 17 mounted to the cushion 42. The nozzles 17 are mounted to the cushion 42 to add flexibility to the nozzles 17 with respect to the cushion 42. For example, FIG. 43 illustrates nozzles 17 mounted within respective rounded recesses 120 or scalloped reliefs provided in the side wall of the cushion 42. The depth of the recess 120 may be suitably modified to provide desired variations of flexibility. For example, the recesses 120 may be relatively deep for greater flexibility as shown in FIG. 44, or the recesses 120 may be relatively shallow for moderate flexibility as shown in FIG. 45. FIG. 46 illustrates an embodiment wherein a radial notch 22 is provided in the conduit 19 that interconnects each nozzle 17 with the cushion 42. The notch 22 adds flexibility to the conduit 19 which facilitates movement of the nozzle 17 with respect to the cushion 42.

FIGS. 47-51 illustrate embodiments of nozzles 17 having a nozzle portion 21 and a conduit 19 that interconnects the nozzle portion 21 with the side wall of the cushion 42. As illustrated, the cross-sectional configuration of the conduit 19 may be varied to vary the flexibility of the nozzle 17. For example, FIGS. 47 and 48 illustrate an embodiment wherein the conduit 19 has a substantially constant cylindrical cross-sectional configuration along its length. FIGS. 49-51 illustrate an embodiment wherein the cross-sectional configuration of the conduit 19 varies along its length. As illustrated, the conduit 19 has an elliptical cross-sectional configuration near the nozzle portion 21 which continuously varies to a cylindrical cross-sectional configuration near the side wall of the cushion 42. Thus, the conduit has a "swept" cross-sectional configuration. In other embodiments, the nozzles 17 may include anatomically-shaped nozzle portions, and the nozzle portions may include openings that are off-center from the conduit opening. Preferably, the cross-sectional shape of the conduit and the nozzle opening are similar or the same, although dissimilar shapes are also possible. Also, the nozzles 17 may be structured to dilate the patient's nose similar to the structure shown in FIG. 18 of U.S. Pat. No. 4,782,832, which is incorporated herein by reference.

Figure 53:
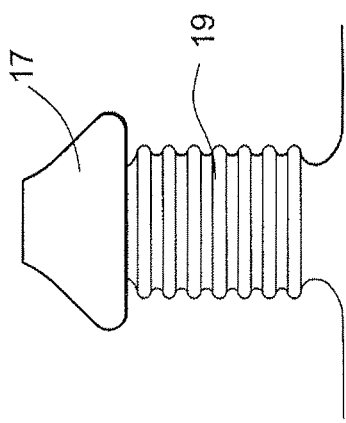
Figure 54:
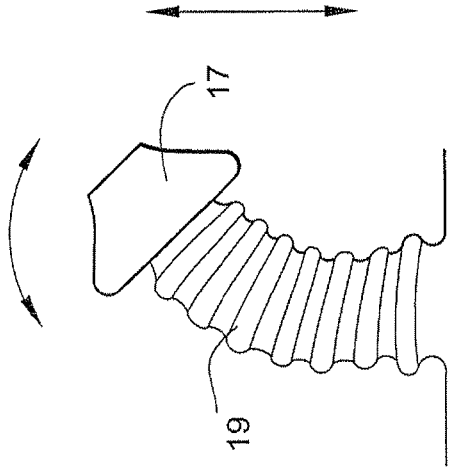
Figure 52:
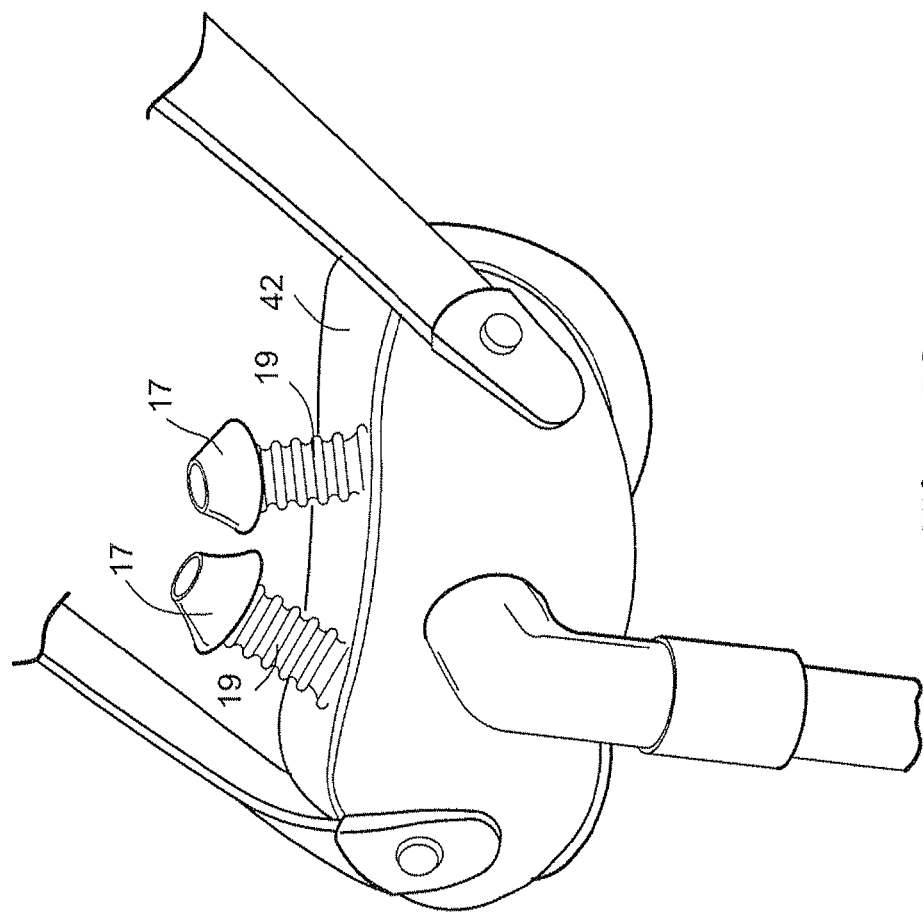

FIGS. 52-54 illustrate an embodiment of a patient interfaces including a cushion 42 and a pair of nozzles 17 mounted to the cushion 42. As illustrated, the nozzle conduits 19 have a concertina configuration, e.g., accordion-like, which adds flexibility to the nozzles 17 with respect to the cushion 42. Specifically, the concertina configuration allows both rotational and vertical adjustment of the nozzles 17 with respect to the cushion 42. For example, FIG. 53 shows a nozzle 17 in a neutral position, and FIG. 54 shows a nozzle 17 stretched and rotated with respect to the cushion 42. The concertina configured conduit 19 may be constructed from a soft silicone material or a stiffer material, e.g., drinking straw material, to allow articulation and extension. This configuration allows the conduits to be adjustably positioned in a number of different positions, and maintained in position during use. Also, the nozzles 17 may be integrally formed in one-piece along with the cushion 42, or the nozzles 17 may be formed separately from the cushion 42 and mounted thereto.

Figure 55A:
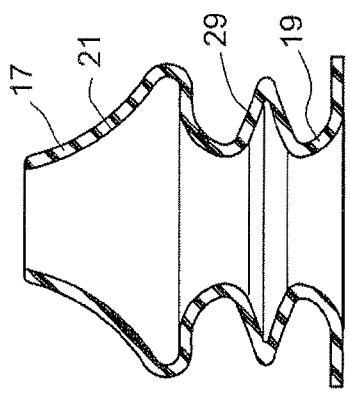
Figure 55B:
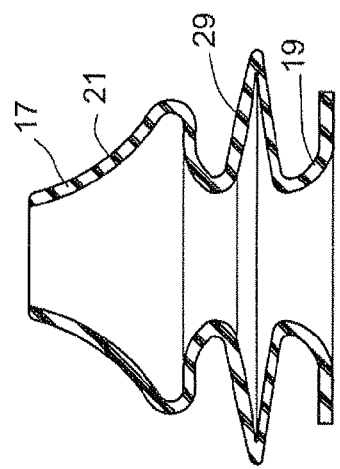

FIGS. 55a-56b illustrate embodiments of nozzles 17 for use in a patient interface. As shown in FIGS. 55a and 55b, each nozzle 17 may include a gusset portion 29 in the conduit 19 that interconnects the nozzle portion 21 with a cushion. The gusset portion may have any suitable width. For example, FIG. 55a illustrates a narrower gusset portion 29, whereas FIG. 55b illustrates a wider gusset portion 29. The gusset portion 29 would allow articulation of the nozzle 17 as well as provide upward pressure of the nozzle 17 into the patient's nasal passage. That is, the gusset portion 29 allows the change in sealing force to be in accordance with the change in treatment pressure.

Figure 56A:
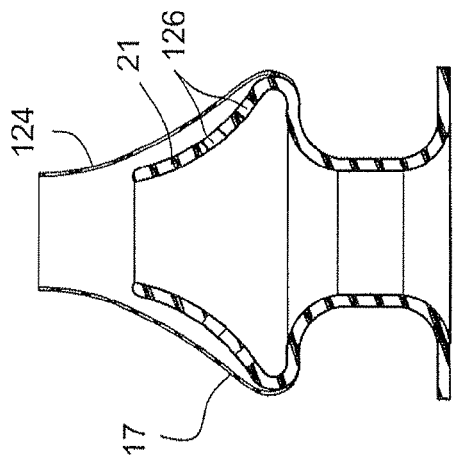
Figure 56B:
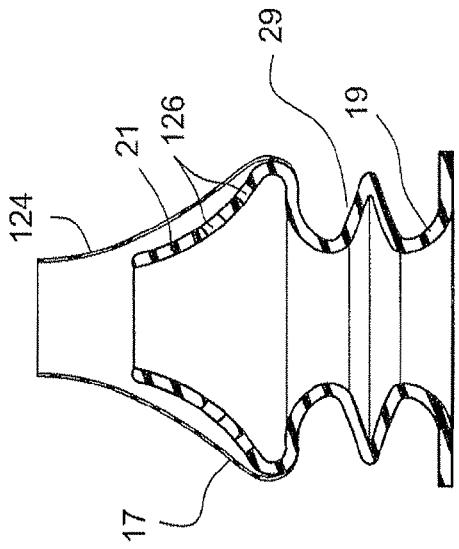

As shown in FIGS. 56a and 56b, each nozzle 17 may include a dual wall construction. Specifically, the nozzle 17 includes a thin membrane 124 that surrounds the upper nozzle portion 21 to enhance the seal of the nozzle 17 with the patient's nasal passage. As illustrated, the upper nozzle portion 21 may include one or more openings 126 for air communication to improve inflation of the membrane 124. The openings 126 may have any suitable shape, e.g., ring-like, and may have any suitable size. Also, as shown in FIG. 56b, each nozzle 17 may include a gusset portion 29 in the conduit 19 that interconnects the nozzle portion 21 with a cushion. Further, both embodiments may include more than one membrane 124, thereby providing a nozzle having a three or more wall construction.

FIGS. 57-62 illustrate embodiments of support members for supporting nozzles 17 of a patient interface and properly aligning them with the patient's nasal passages. For example, FIGS. 57 and 58 illustrate a support member in the form of a C-shaped spring 130 having openings 132 for receiving nozzle conduits therein. The spring 130 is positioned between the side wall 51 of the cushion 42 and the nozzle portions 21 of the nozzles 17, and provides a biasing force to extend the nozzles 17 and maintain a substantially rigid configuration to facilitate proper alignment and seal with the patient's nasal passages. The spring 130 may be constructed of any suitable material, e.g., metal or polymer. Also, additional adjustment may be added to the spring, e.g., additional bending axis 131 that allows lateral adjustment of the nozzles.

FIGS. 59 and 60 illustrate a support member in the form of an adjustable slider mechanism 134 having a mounting portion 135 and a support portion 136 with openings 137 for receiving nozzle conduits therein. The mounting portion 135 is secured to the frame 38 of the patient interface, e.g., by a fastener, and the support portion 136 is engaged with the nozzle portions 21 to extend the nozzles 17 and maintain a substantially rigid configuration to facilitate proper alignment and seal with the patient's nasal passages. As illustrated, the opening 138 in the mounting portion 135 for receiving the fastener is elongated, which allows adjustment of the mechanism 134 with respect to the nozzles 17. Also, additional adjustment may be added to the mechanism, e.g., additional bending axis 131 that allows lateral adjustment of the nozzles and bending axis 133 to change the angle of contact between the nozzles and patient.

FIGS. 61 and 62 illustrate a support member in the form of a wedge 140 having openings 142 for receiving nozzle conduits therein. The wedge 140 is positioned between the side wall 51 of the cushion 42 and the nozzle portions 21 of the nozzles 17, and extends the nozzles 17 and maintains a substantially rigid configuration to facilitate proper alignment and seal with the patient's nasal passages. The wedge 140 may have various angles and thicknesses to achieve the optimal alignment and seal of the nozzles 17. Also, additional adjustment may be added to the wedge, e.g., additional bending axis 131 that allows lateral adjustment of the nozzles. Further, the wedge 140 may be constructed of any suitable material, e.g., foam, rigid plastic, elastomeric material such as silicone.

Figure 64:
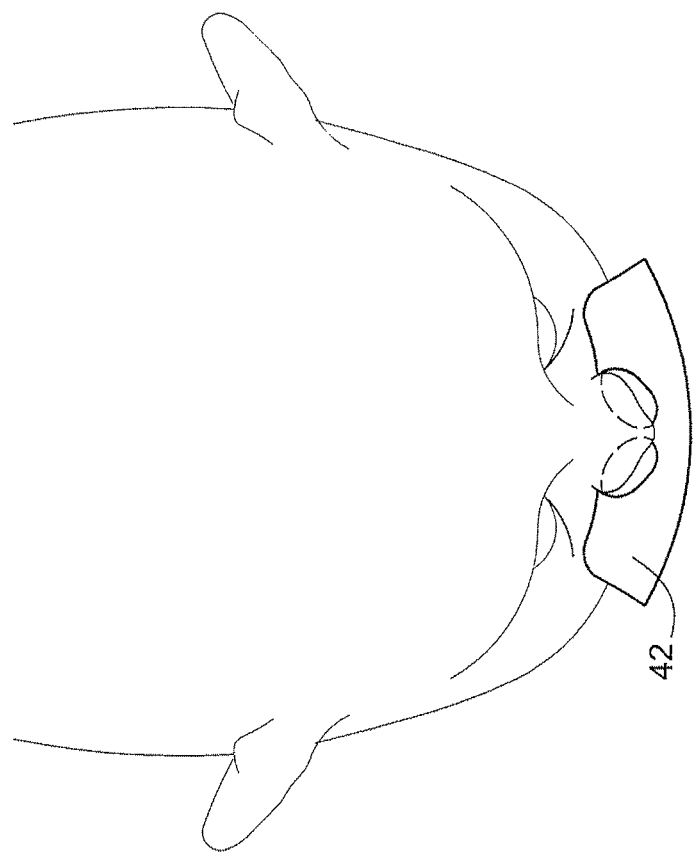
FIGS. 63-64 illustrate an embodiment of a patient interface with a boomerang-shaped cushion.
Figure 63:
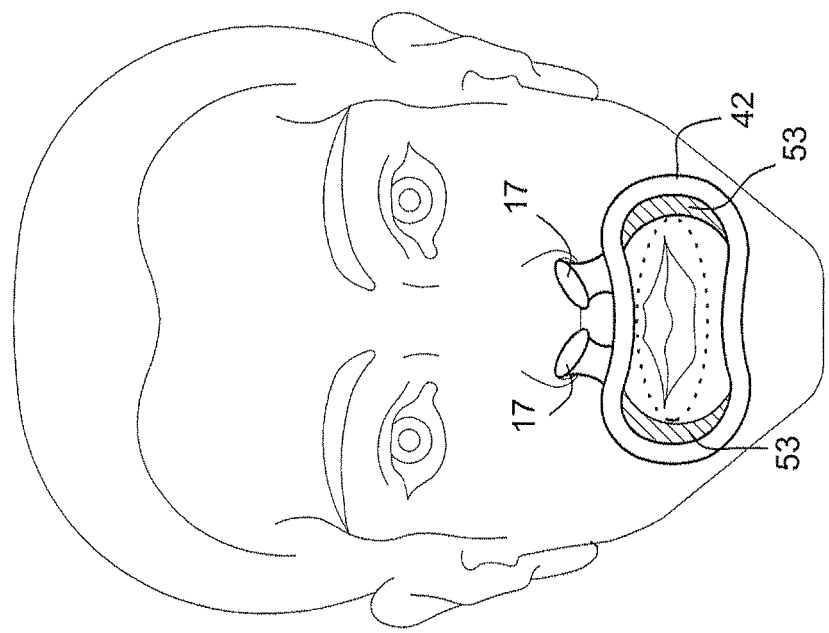

FIGS. 63 and 64 illustrate an embodiment of a patient interface having a cushion 42 and a pair of nozzles 17 mounted to the cushion 42. As illustrated, the cushion 42 is shaped as a boomerang, and may include rims 53 extending from the side wall of the cushion 42.

Figure 65C:
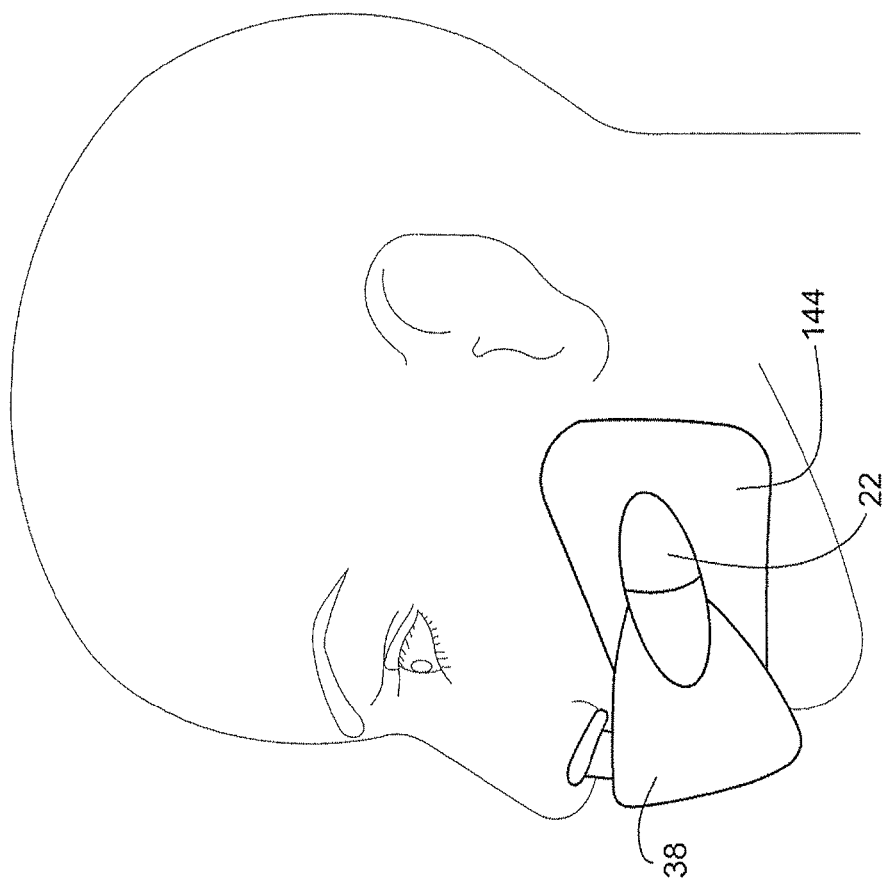
Figure 65B:
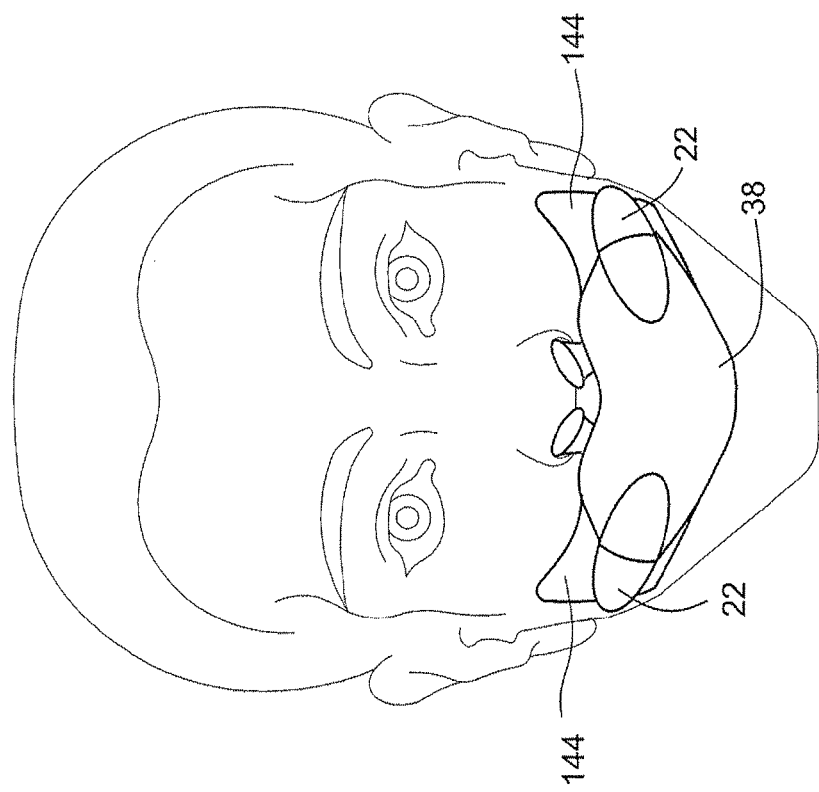

FIGS. 65a-65c illustrate an embodiment of a patient interface wherein the frame 38 includes extended portions 144 to cover the cheek regions of the patient's face. This arrangement is structured to prevent or at least control cheek blowout. Also, as illustrated, the frame 38 is structured such that inlet conduits 22 are coupled to opposing sides of the frame 38 for delivering breathable gas into the patient interface. However, one or more inlet conduits 22 may be coupled to the frame 38 in any other suitable manner, e.g., to the front of the frame.

Figure 67:
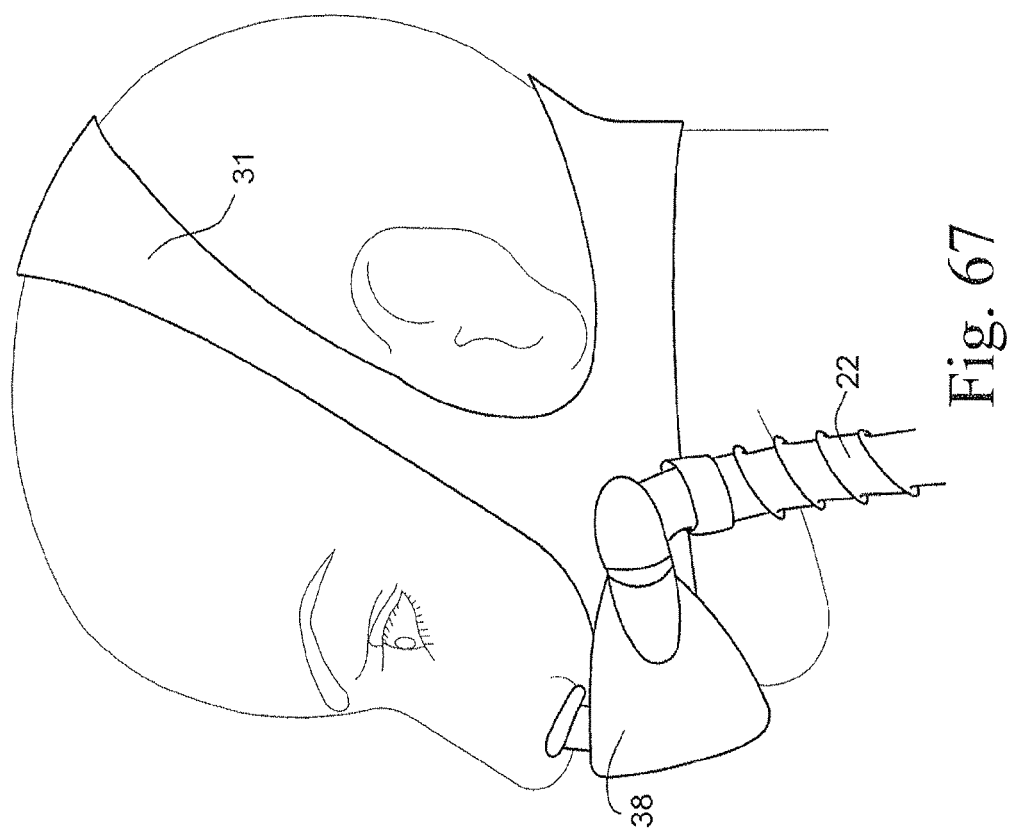
Figure 66A:
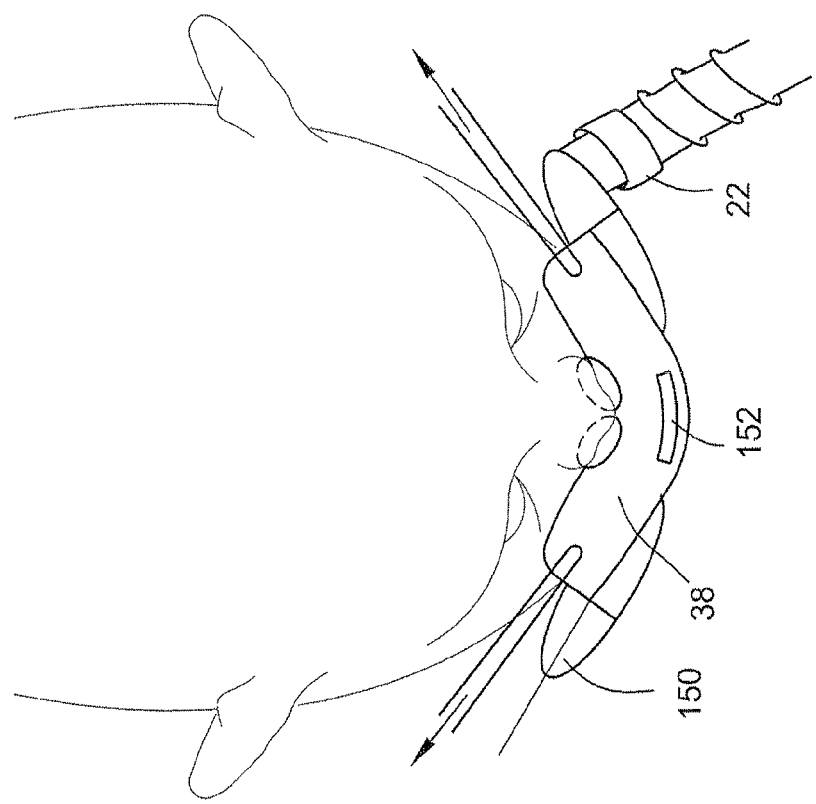

FIGS. 66a-67 illustrate an embodiment of a patient interface wherein the frame 38 includes an inlet conduit 22 coupled to one side thereof and an anti-asphyxia valve module 150 coupled to the opposite side thereof. It should be understood that the inlet conduit 22 and module 150 can be interchanged.

As shown in FIG. 66b, the anti-asphyxia module 150 includes an anti-asphyxia valve 154 that is housed within an anti-asphyxia cap 156 secured to the frame 38. As illustrated, the anti-asphyxia cap 156 includes a plurality of openings 157, and the anti-asphyxia valve 154 includes a flexible membrane 155 that is movable between operative and inoperative positions. In the inoperative position (shown in solid line in FIGS. 66c and 66d), the membrane 155 is spaced from the cap 156 so that atmospheric air can pass through the openings 157. The membrane 155 is moved into the operative position (shown in dotted lines in FIGS. 66c and 66d) by mask pressure and closes the openings 157 so that atmospheric air cannot pass through the openings 157. Embodiments of such anti-asphyxia valve and anti-asphyxia cap are disclosed in WO200038772, the contents of which are hereby incorporated by cross-reference.

The anti-asphyxia valve module 150 has the advantage of being in close proximity to the patient's mouth. The close proximity to the mouth improves $CO_2$ washout, is good for the stability of the system (i.e., there is not a heavy weight located at a distance from the patient interface), and is fail safe if the anti-asphyxia valve module 150 is not attached to the device. As illustrated, the frame and/or cushion may include an exhaust vent 152. Also, headgear 31 is attached to frame 38 in any suitable manner to maintain the cushion and nozzles in a desired adjusted position on the patient's face. In the illustrated embodiment, the headgear 31 includes a strap that extends below the ears and around the upper portion of the patient's neck, and a strap that extends in front of the ears and over the top of the patient's head. However, the headgear 31 may include any other suitable strap arrangement.

Figure 69:
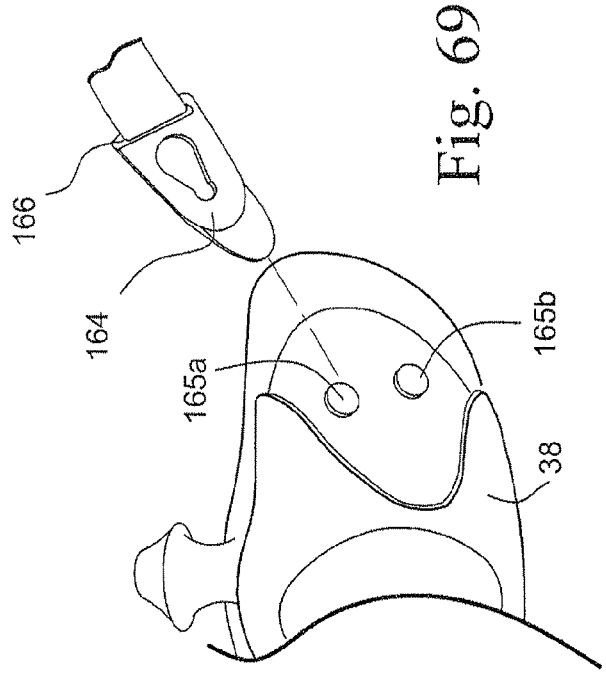
Figure 70:
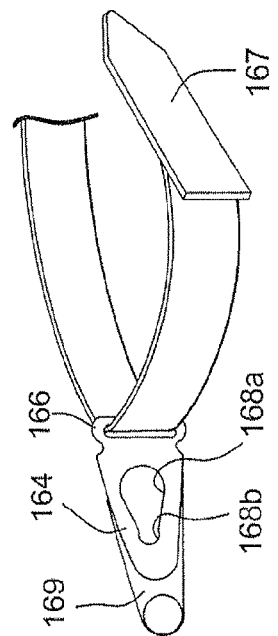
Figure 68:
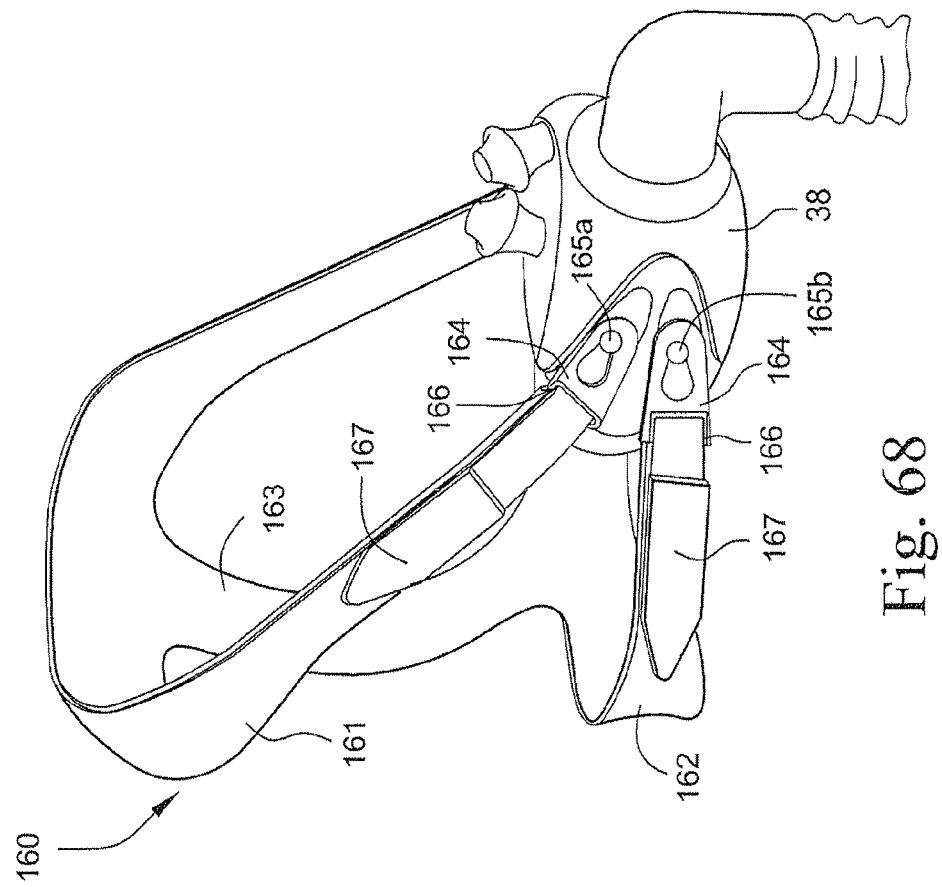

FIGS. 68-70 illustrate an embodiment of a headgear assembly 160 removably coupled to the frame 38 of a patient interface so as to maintain the cushion and nozzles in a desired adjusted position on the patient's face. As illustrated, the headgear assembly 160 includes two straps each having an independent attachment to the frame 38. Specifically, the headgear assembly 160 includes an upper strap 161, a lower strap 162, and a connecting strap 163 that interconnects the upper and lower straps 161, 162. Each end of the upper and lower straps 161, 162 includes an attachment member 164 adjustably secured thereto. Each attachment member 164 is interlockable with a respective anchor 165a, 165b provided on the frame 38 as discussed in greater detail below.

As best shown in FIGS. 68 and 70, each attachment member 164 includes a crossbar 166 that enables respective end portions of the straps to be wrapped around, in a known manner. The free ends of the straps include a strip of hook material 167 attached thereto by stitching, for example, that engages the loop material of the remainder of the strap to secure the attachment member in place. The hook/loop arrangement, e.g., Velcro®, allows adjustment of the straps with respect to the attachment member 164. Each attachment member 164 is in the form of a female connector that includes a relatively large lead-in opening 168a that leads into a relatively smaller attachment opening 168b.

The frame includes a main body and side frame member provided on each lateral side of the main body. The main body includes an aperture that is coupled to an inlet conduit (22) for delivering breathable gas. Upper and lower anchors 165a, 165b on each side thereof. As best shown in FIG. 69, each anchor is in the form of a male connector, e.g., protruding knob. In use, each attachment member 164 is interlocked with a respective anchor 165a, 165b by first moving the attachment member 164 adjacent the respective anchor 165a, 165b such that the respective anchor 165a, 165b extends through the larger opening 168a, and then the attachment member 164 is moved to interlock the respective anchor 165a, 165b with the smaller opening 168b. As shown in FIG. 68, the attachment members 164 on the ends of the lower strap 162 are adapted to releasably interlock with respective lower anchors 165b on the frame 38, and the attachment members 164 on the ends of the upper strap 161 are adapted to releasably interlock with respective upper anchors 165a on the frame 38. As shown in FIG. 70, a soft flexible finger tab 169 is provided on the end of each attachment member 164 to facilitate engagement and disengagement of the attachment member 164 to the frame 38. As illustrated, the free end of the finger tab 169 may include a ball-like shape.

When mounted, each attachment member 164 is substantially flush with the frame 38. As a result, this arrangement provides no protrusions that can lead to inadvertent disengagement of the straps. Also, there are no obstructions to the patient, e.g., when sleeping on his/her side.

Also, the arrangement enables intuitive and dexterous attachment movement, permits quick release of the patient interface, and the attachment member 164 may be freely rotated with respect to the anchor 165a, 165b to allow the patient interface to self-align on the patient's face.

When mounted on a patient, the upper and lower straps 161, 162 follow two vectors to effect mask stability. Specifically, the lower strap 162 extends below the ears and around the upper portion of the patient's neck and the upper strap 161 extends over the ears and around a top portion of the patient's head. The connecting strap 163 extends along the rear portion of the patient's head, which holds the lower strap 162 in place during head rotation. One or more of the straps may be flared, e.g., at the rear, in order to better conform with the contours of the patient's head which helps reduce head pressure from strap tension.

The above arrangement enables the patient interface to be balanced, e.g., by tuning the patient interface so that sufficient pressure is applied to regions of the cushion and nozzles so an adequate seal is attained. Also, the above arrangement positions the straps away from patient's face.

FIGS. 71-73 illustrate another embodiment of a headgear assembly 170 removably coupled to the frame 38 of a patient interface. As illustrated, the headgear assembly 170 includes two straps each having an independent attachment to the frame 38. Specifically, the headgear assembly 170 includes an upper strap 171 and a lower strap 172. Each end of the upper strap 171 includes an upper locking clip 173a secured thereto and each end of the lower strap includes a lower locking clip 173b secured thereto. Each locking clip 173a, 173b is interlockable with a respective clip receiver 174a, 174b provided on the frame 38 as discussed in greater detail below.

As illustrated, each upper clip 173a includes a crossbar 175 that enables respective end portions of the upper straps 171 to be wrapped around, in a known manner. In the illustrated embodiment, each free end of the upper strap 171 is secured to the remainder of the strap, e.g., by stitching, to secure the clip in place. Also, an intermediate portion of the upper strap 171 includes an adjustable ladder lock arrangement 176 for adjustment purposes. Each lower clip 173b includes an adjustable ladder lock arrangement 177 that enables respective end portions of the lower strap 172 to be engaged, in a known manner. Each free end of the lower strap 172 is held in place to the remainder of the strap by a watch strap style retainer 178. However, the straps may be secured to the clips 173a, 173b in any other suitable manner, e.g., Velcro®. Further, each clip 173a, 173b includes a side wall having a longitudinally extending slot 180 that leads into a transversely extending slot 181.

The frame 38 includes upper and lower clip receivers 174a, 174b on each side thereof. As best shown in FIG. 73, each clip receiver 174a, 174b includes a resiliently flexible tab 182 having a ramped surface leading to a locking shoulder 183 and a release projection 184. In use, each clip 173a, 173b is interlocked with a respective clip receiver 174a, 174b by first moving the clip receiver 174a, 174b into the respective clip 173a, 173b such that the release projection 184 extends through the longitudinally extending slot 180 until the locking shoulder 183 interlocks with the transversely extending slot 181 with a snap fit. The clip 173a, 173b may be released from the respective clip receiver 174a, 174b by depressing the release projection 184 until the locking shoulder 183 releases from the transversely extending slot 181. As shown in FIG. 71, the lower clips 173b on the ends of the lower strap 172 are adapted to releasably interlock with respective lower clip receivers 174b on the frame 38, and the upper clips 173a on the ends of the upper strap 171 are adapted to releasably interlock with respective upper clip receivers 174a on the frame 38. The clip arrangement may provide audible feedback when the clip 173a, 173b is attached to the respective clip receiver 174a, 174b.

Also, as shown in FIG. 73, each clip 173a, 173b may be rotatably engaged with the respective strap such that the clip 173l, 173b may be freely rotated with respect to the strap to allow the patient interface to self-align on the patient's face.

Similar to the above-described headgear arrangement, the lower strap 172 extends below the ears and around the upper portion of the patient's neck and the upper strap 171 extends over the ears and around a top portion of the patient's head.

FIGS. 74-76 illustrate another embodiment of a headgear assembly 190 removably coupled to the frame 38 of a patient interface. As illustrated, the headgear assembly 190 includes two straps with a single point of attachment to the frame 38. Specifically, the headgear assembly 190 includes an upper strap 191 and a lower strap 192. One end of the upper and lower straps 191, 192 is adjustably secured to one attachment member 193, and the other end of the upper and lower straps 191, 192 is adjustably secured to another attachment member 193. Each attachment member 193 is interlockable with a respective anchor 194 provided on the frame 38 as discussed in greater detail below.

As best shown in FIG. 76, each attachment member 193 is generally V-shaped and includes a upper and lower crossbars 195a, 195b that enable respective end portions of the straps 191, 192 to be wrapped around, in a known manner. The free ends of the straps 191, 192 include a strip of hook material attached thereto by stitching, for example, that engages the loop material of the remainder of the strap to secure the attachment member in place. The hook/loop arrangement, e.g., Velcro®, allows adjustment of the straps 191, 192 with respect to the attachment member 193. However, the straps 191, 192 may be secured to the attachment member 193 in any other suitable manner, e.g., adjustable ladder-lock arrangement. Each attachment member 193 includes a relatively large lead-in into a relatively smaller attachment opening 196.

The frame includes an anchor 194 on each side thereof. As best shown in FIG. 75, each anchor 194 is in the form of a protruding knob. Moreover, each anchor 194 is mounted on a sliding adjustment mechanism that allows sliding adjustment of the anchor 194 between upper and lower portions of the frame 38. Specifically, the anchor 194 is mounted on a slide 197 that is movable by a button 198 by sliding the button 198 within a slot to adjust the anchor height. The adjustment mechanism may be held in position by, e.g., frictional engagement, detents that would allow for discrete steps of movement.

In use, each attachment member 193 is interlocked with a respective anchor 194 by first moving the attachment member 193 adjacent the respective anchor 194 such that the anchor 194 extends through the lead-in, and then the attachment member 193 is moved to interlock the anchor 194 with the smaller attachment opening 196. As shown in FIG. 76, a spring mechanism 199 may be incorporated into the opening 196 so that the connection does not wear. As shown in FIG. 74, each end of the frame 38 interlocks with a respective attachment member 193, and each attachment member 193 secures ends of the respective upper and lower straps 191, 192. As illustrated, a soft flexible finger tab 200 is provided on the end of each attachment member 193 to facilitate engagement and disengagement of the attachment member 193 to the frame 38. As illustrated, the free end of the finger tab 200 may include one or more protrusions for finger grip. Also, the headgear straps 191, 192 are preferably elastic to help with fitting.

The arrangement enables intuitive and dexterous attachment movement, permits quick release of the patient interface, and the attachment member 193 may be freely rotated with respect to the anchor 194 to allow the patient interface to self-align on the patient's face.

Similar to the above-described headgear arrangements, the lower strap 192 extends below the ears and around the upper portion of the patient's neck and the upper strap 191 extends over the ears and around a top portion of the patient's head.

FIGS. 77 and 78 illustrate another embodiment of a headgear assembly 210 removably coupled to the frame 38 of a patient interface. As illustrated, the headgear assembly 210 includes two straps with a single point of attachment to the frame 38. Specifically, the headgear assembly 210 includes an upper strap 211 and a lower chin strap 212. One end of the upper and lower straps 211, 212 is adjustably secured to one attachment member 213, and the other end of the upper and lower straps 211, 212 is adjustably secured to another attachment member 213. Each attachment member 213 is interlockable with a respective anchor 214 provided on the frame 38 as discussed in greater detail below.

As best shown in FIG. 78, each attachment member 213 includes an upper clip receiver 215 and a lower crossbar 216 As illustrated, end portions of the upper strap 211 are secured to respective locking clips 217 (e.g., strap wrapped around clip cross-bar and free end of the strap is secured to the remainder of the strap by Velcro® arrangement), which are releasably interlocked with a respective upper clip receiver 215. The interlocking engagement may be similar to the snap-fit clip arrangement disclosed in FIGS. 71-73. Respective end portions of the lower strap 212 are wrapped around a respective lower cross-bar 216, in a known manner. The free ends of the lower straps 212 may engage the remainder of the strap via a Velcro® arrangement. Each attachment member 213 also includes a relatively large lead-in into a relatively smaller attachment opening 218.

The frame 38 includes an anchor 214, e.g., in the form of a protruding knob, on each side thereof. The anchors 214 may be mounted on a sliding adjustment mechanism similar to that shown in FIGS. 74 and 75. In use, each attachment member 213 is interlocked with a respective anchor 214 by first moving the attachment member 213 adjacent the respective anchor 214 such that the anchor 214 extends through the lead-in, and then the attachment member 213 is moved to interlock the anchor 214 with the smaller attachment opening 218. As shown in FIG. 78, a spring mechanism 219 may be incorporated into the opening 218 so that the connection does not wear. As shown in FIG. 77, each end of the frame 38 interlocks with a respective attachment member 213, and each attachment member 213 secures ends of the respective upper and lower straps 211, 212. As illustrated, a soft flexible finger loop 220 is provided on the side of each attachment member 213 to provide a means for quick disengagement of the attachment member 213 from the frame 38. Also, the headgear straps 211, 212 are preferably elastic to help with fitting.

The arrangement enables intuitive and dexterous attachment movement, permits quick release of the patient interface, and the attachment member 213 may be freely rotated with respect to the anchor 214 to allow the patient interface to self-align on the patient's face.

When mounted on a patient, the lower strap 212 extends downwardly and around the patient's chin and the upper strap 211 extends over the ears and around a top portion of the patient's head.

Figure 80:
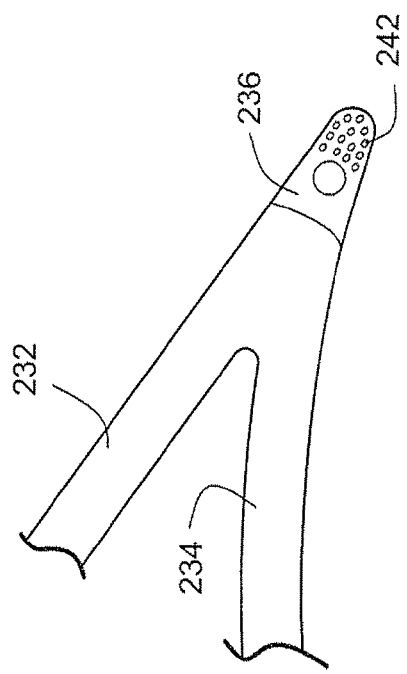
Figure 79:
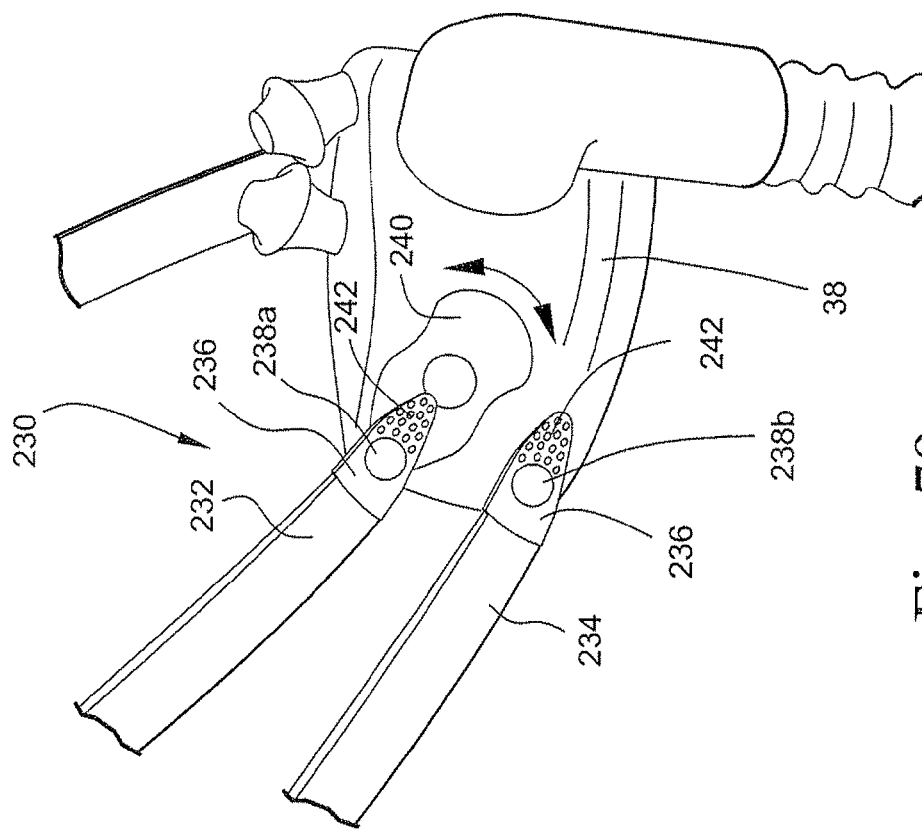

FIGS. 79-80 illustrate another embodiment of a headgear assembly 230 removably coupled to the frame 38 of a patient interface. As shown in FIG. 79, the headgear assembly 230 includes an upper strap 232 and a lower strap 234. However, the lower strap 234 is optional. Also, the strap may have two-strap configuration wherein upper and lower straps 232, 234 are incorporated into a single structure as shown in FIG. 80. Each end of the straps includes an attachment member 236 adjustably secured thereto. Each attachment member 236 is interlockable with a respective anchor 238a, 238b provided on the frame 38 as discussed in greater detail below.

Each attachment member 236 may be secured to a respective end of the strap in any suitable manner, e.g., stitching, Velcro®. Also, each attachment member 236 includes an attachment opening.

The frame 38 includes upper and lower anchors 238a, 238b on each side thereof. Each anchor 238a, 238b is in the form of a protruding knob. In use, each attachment member 236 is interlocked with a respective anchor 238a, 238b by moving the attachment member 236 adjacent the respective anchor 238a, 238b such that the respective anchor 238a, 238b extends through the attachment opening.

As shown in FIG. 79, the upper anchor 238a is mounted on a rotatable plate 240 that allows the position of the upper anchor 238a to be rotatably adjusted. This arrangement allows the angle of the patient interface with respect to the patient's face to be adjusted. Moreover, the arrangement allows the headgear assembly 230 to remain in the same position relative to the patient's head even as the angle of the patient interface changes. Rotation may be discrete with specific indexed positions, or rotation may be continuous with the desired position being maintained by friction.

A soft flexible finger tab 242 is provided on the end of each attachment member 236 to facilitate engagement and disengagement of the attachment member 236 to the frame 38. As illustrated, the free end of the finger tab 242 may include one or more gripping protrusions.

Also, all the headgear assemblies described above may incorporate rigidizing elements (via insertion of rigid panels, stitiching, lamination, or other means) to add rigidity to the headgear assemblies to aid in mask stability.

It should be understood that the cushion 42 and nozzles 17 described above may be formed from any suitable material. For example, the cushion 42 and nozzles 17 may be formed from a gel-like material, or they may be formed from a foam-like material. Also, the cushion 42 and nozzles 17 may be formed separately from one another, or may be integrally formed as a one-piece structure.

Further, although the above embodiments are described in relation to nozzles, nasal prongs (which are inserted into the nose) and/or nasal dilators are also contemplated.

Advantages of illustrated preferred embodiments may include:

reducing significantly the bulk required to form an effective nasal and oral seal. This has the advantage of creating a less intrusive patient interface that significantly reduces the problems of patient claustrophobia. The removal of the requirement to seal around the nasal bridge provides the opportunity for the patient to wear spectacles. In addition this removes the danger of leaks affecting the sensitive eye region, thereby reducing the possibility of creating conjunctivitis style problems.

reducing the force (headgear tension) required to maintain the seal as compared to current full face masks in the prior art. The force is reduced due to the reduction in the effective area of the cushion on to the face. As a result, there is less area over which the pressure inside the patient interface acts and the resultant headgear tension is reduced.

improving seal as it avoids the nose bridge region where leak commonly occurs, thus the force required to deform the cushion and effect a seal is also reduced. The reduction in the headgear tension and cushion to face force would substantially reduce the discomfort to a patient.

The reduction in the area of the face across which a seal must be formed allows a single size or shape to fit a wider range of patient geometry. This is particularly advantageous for a clinician since the patient interface is both easier to fit to a new patient and potentially more forgiving of fitting errors.

The independent nature of the chambers due to the flexible connection, also allows for some movement of the face during the night without loss of seal. This leads to far more stability than conventional single chamber full face masks.

The provision of flexibility allows the seal to remain throughout jaw and head position movement as well as providing adjustment for the different geometry of a wide range of patients. The task of fitting varying patient geometry is made easier by the removal of the need to seal around the complex form of the nasal bridge which is found in most of the prior art masks that seal both the nasal and oral passages. The lack of seal around the nasal bridge also allows the patient to wear spectacles.

Although the invention has been described with reference to the illustrated embodiments, it is to be understood that the illustrated embodiments are merely illustrative of the application of the principles of the invention. Numerous modifications may be made therein and other arrangements may be devised without departing from the spirit and scope of the invention.

What is claimed is:

1. A breathing arrangement for use between a patient and a structure to deliver a flow of pressurized breathable gas to the patient for treatment of sleep disordered breathing, the breathing arrangement comprising:
   a ventilation interface defining a gas entry port to be fluidically connected to the structure to deliver the flow of pressurized breathable gas;
   an oral interface provided to said ventilation interface, the oral interface configured to seal only along an exterior of the patient's mouth when applied to the patient's face;
   a nasal interface configured to fluidically couple the gas entry port with nares of the patient when the nasal interface is applied to the patient's nose without forming a seal on a nasal bridge region of the patient's face; and
   headgear connected to at least one of the ventilation interface and the nasal interface so as to maintain the oral interface and the nasal interface in a desired position on the patient's face and maintain a substantially gas-tight seal between the patient's face and the oral interface and the nasal interface,
   wherein the oral interface includes an elastomeric side wall, and the nasal interface is flexibly connected to and supported along the elastomeric side wall to provide flexibility between the nasal interface and the oral interface and provide for movement and changes in alignment between the nasal interface and the oral interface.

2. The breathing arrangement according to claim 1, further comprising a flexible element to flexibly connect the nasal interface and the oral interface.

3. The breathing arrangement according to claim 2, wherein the flexible element is structured to allow gas to pass between the oral interface and the nasal interface so that pressurized breathable gas is delivered to both the patient's nose and the patient's mouth in use.

4. A breathing arrangement for use between a patient and a structure to deliver a flow of pressurized breathable gas to the patient for treatment of sleep disordered breathing, the breathing arrangement comprising:
   a ventilation interface defining a gas entry port to be fluidically connected to the structure to deliver the flow of pressurized breathable gas;
   an oral interface provided to said ventilation interface, the oral interface configured to seal only along an exterior of the patient's mouth when applied to the patient's face;
   a nasal interface configured to fluidically couple the gas entry port with nares of the patient when the nasal interface is applied to the patient's nose without forming a seal on a nasal bridge region of the patient's face; and
a bellows to flexibly connect the nasal interface and the oral interface,
wherein the nasal interface is flexibly connected to the oral interface to provide flexibility between the nasal interface and the oral interface and provide for movement and changes in alignment between the nasal interface and the oral interface.

5. The breathing arrangement according to claim 1, wherein the ventilation interface comprises a frame.

6. The breathing arrangement according to claim 1, wherein the ventilation interface comprises at least one vent.

7. The breathing arrangement according to claim 1, wherein the ventilation interface is relatively rigid and the oral interface is relatively flexible.

8. The breathing arrangement according to claim 1, wherein the ventilation interface and the oral interface are constructed of different materials.

9. The breathing arrangement according to claim 1, wherein the ventilation interface comprises a polycarbonate material.

10. The breathing arrangement according to claim 1, wherein the oral interface comprises a silicone material.

11. The breathing arrangement according to claim 1, wherein the oral interface is integral with the ventilation interface.

12. The breathing arrangement according to claim 1, wherein the oral interface is removably and substantially gas-tightly connected to the ventilation interface.

13. The breathing arrangement according to claim 12, wherein the oral interface is connected to the ventilation interface via a clip.

14. A breathing arrangement for use between a patient and a structure to deliver a flow of pressurized breathable gas to the patient for treatment of sleep disordered breathing, the breathing arrangement comprising:
a ventilation interface defining a gas entry port to be fluidically connected to the structure to deliver the flow of pressurized breathable gas;
an oral interface provided to said ventilation interface, the oral interface including a face-contacting portion configured to seal only along an exterior of the patient's mouth when applied to the patient's face, and the face-contacting, portion defining an aperture adapted to be in direct fluid communication with the patient's mouth for delivery of the flow of pressurized breathable gas to the patient's mouth; and
a nasal interface configured to fluidically couple the gas entry port with nares of the patient when the nasal interface is applied to the patient's nose without forming a seal on a nasal bridge region of the patient's face,
wherein the oral interface and the nasal interface are integrally formed as a one-piece structure, and
wherein the nasal interface is flexibly connected to the oral interface to provide flexibility between the nasal interface and the oral interface and provide for movement and changes in alignment between the nasal interface and the oral interface.

15. The breathing arrangement according to claim 1, wherein the oral interface, the nasal interface, and the ventilation interface are integral to form a one-piece oral and nasal mask.

16. The breathing arrangement according to claim 1, wherein the oral interface includes a cushion comprising an aperture adapted to receive the patient's mouth.

17. The breathing arrangement according to claim 16, wherein the cushion includes a non-face-contacting portion and a face-contacting portion, the non-face-contacting portion being provided to the ventilation interface and the face-contacting portion having a resilient membrane structured to provide a seal.

18. The breathing arrangement according to claim 17, wherein the cushion includes the side wall, and the cushion further includes a rim extending away from the side wall, and the membrane is spaced from and substantially surrounds the rim.

19. The breathing arrangement according to claim 1, wherein the oral interface includes a gusset portion.

20. The breathing arrangement according to claim 1, wherein the gas entry port is disposed on a front surface of the ventilation interface.

21. The breathing arrangement according to claim 1, wherein the nasal interface includes two separate openings to deliver the flow of pressurized breathable gas to the patient's nares when the nasal interface is applied to the patient's nose.

22. The breathing arrangement according to claim 1, wherein the nasal interface comprises two separate nasal pillows adapted to deliver the flow of pressurized breathable gas to the patient's nares.

23. The breathing arrangement according to claim 1, wherein the ventilation interface includes a swiveling elbow connector to attach the ventilation interface to the structure to deliver the flow of pressurized breathable gas.

24. The breathing arrangement according to claim 23, wherein the elbow connector includes an anti-asphyxia valve.

25. The breathing arrangement according to claim 1, wherein the oral interface and the ventilation interface define a first interior breathing chamber fluidically connected to the gas entry port for receiving the gas therein, and the nasal interface defines a second interior breathing chamber fluidically connected to first interior breathing chamber for supplying the gas to the patient's nose.

26. The breathing arrangement according to claim 1, wherein the oral interface and the nasal interface form one chamber.

27. The breathing arrangement according to claim 1, wherein the headgear is adjustable.

28. The breathing arrangement according to claim 1, wherein the ventilation interface includes lower headgear connector portions on each side thereof.

29. The breathing arrangement according to claim 28, further comprising clips structured to attach the headgear to respective lower headgear connector portions.

30. The breathing arrangement according to claim 29, wherein the clips are rotatable with respect to respective lower headgear connector portions.

31. The breathing arrangement according to claim 1, wherein at least one of the nasal interface and the ventilation interface includes headgear connectors to connect the headgear.

32. The breathing arrangement according to claim 31, wherein both the nasal interface and the ventilation interface include headgear connectors to connect the headgear.

33. The breathing arrangement according to claim 31, wherein only the ventilation interface includes headgear connectors to connect the headgear.

34. The breathing arrangement according to claim 1, wherein the headgear includes upper side straps adapted to extend over the patient's ears and lower side straps adapted to extend below the patient's ears.

35. The breathing arrangement according to claim 1, wherein the headgear provides force vectors that allow for effective sealing of the oral interface at the patient's mouth and the nasal interface at the patient's nose, respectively.

36. The breathing arrangement according to claim 35, wherein the headgear assembly includes upper side straps adapted to be routed over the patient's ears and lower side straps adapted to be routed under the patient's ears.

37. The breathing arrangement according to claim 36, wherein the upper and lower side straps are adapted to provide respective force vectors that allow for the effective sealing.

38. The breathing arrangement according to claim 36, wherein the upper side straps are arranged to provide a force vector that is angled upwardly with respect to a horizontal plane of the breathing arrangement.

39. The breathing arrangement according to claim 36, wherein the lower side straps are arranged to provide a force vector that is generally aligned with a horizontal plane of the breathing arrangement.

40. The breathing arrangement according to claim 2, wherein the flexible element is structured to support the nasal interface in its entirety along the side wall to provide flexibility between the nasal interface and the oral interface and provide for independent movement between the entire nasal interface and the oral interface.

41. The breathing arrangement according to claim 10, wherein the flexible element allows the entire nasal interface to be independently aligned with respect to the oral interface.

\* \* \* \* \*

UNITED STATES PATENT AND TRADEMARK OFFICE
CERTIFICATE OF CORRECTION

| | | |
|---|---|---|
| PATENT NO. | : 9,067,033 B2 | Page 1 of 1 |
| APPLICATION NO. | : 13/103491 | |
| DATED | : June 30, 2015 | |
| INVENTOR(S) | : Davidson et al. | |

It is certified that error appears in the above-identified patent and that said Letters Patent is hereby corrected as shown below:

In the Claims:

In claim 36, at column 25, line 4, "wherein the headgear assembly includes upper side straps" should be corrected to ---wherein the headgear includes upper side straps---.

In Claim 41, at column 25, line 25, "The breathing arrangement according to claim 10," should be corrected to ---The breathing arrangement according to claim 40,---.

Signed and Sealed this
Fifteenth Day of December, 2015

Michelle K. Lee
*Director of the United States Patent and Trademark Office*